(12) United States Patent
Majeti et al.

(10) Patent No.: US 11,760,800 B2
(45) Date of Patent: *Sep. 19, 2023

(54) MARKERS OF ACUTE MYELOID LEUKEMIA STEM CELLS

(71) Applicant: The Board of Trustees of the Leland Stanford Junior University, Stanford, CA (US)

(72) Inventors: Ravindra Majeti, Palo Alto, CA (US); Irving L. Weissman, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 288 days.

This patent is subject to a terminal disclaimer.

(21) Appl. No.: 17/000,063

(22) Filed: Aug. 21, 2020

(65) Prior Publication Data

US 2021/0040207 A1 Feb. 11, 2021

Related U.S. Application Data

(63) Continuation of application No. 15/704,790, filed on Sep. 14, 2017, now Pat. No. 10,662,242, which is a continuation of application No. 14/927,349, filed on Oct. 29, 2015, now Pat. No. 9,796,781, which is a continuation of application No. 14/164,009, filed on Jan. 24, 2014, now Pat. No. 9,193,955, which is a continuation of application No. 13/739,788, filed on Jan. 11, 2013, now Pat. No. 8,709,429, which is a continuation of application No. 12/836,152, filed on Jul. 14, 2010, now Pat. No. 8,361,736, which is a continuation-in-part of application No. PCT/US2009/000224, filed on Jan. 13, 2009.

(60) Provisional application No. 61/011,324, filed on Jan. 15, 2008.

(51) Int. Cl.

| C07K 16/28 | (2006.01) |
| C07K 16/30 | (2006.01) |
| A61P 35/02 | (2006.01) |
| C12Q 1/6886 | (2018.01) |
| G01N 33/50 | (2006.01) |
| G01N 33/574 | (2006.01) |
| C12N 5/00 | (2006.01) |
| C12N 5/09 | (2010.01) |
| A61K 39/00 | (2006.01) |

(52) U.S. Cl.
CPC .......... *C07K 16/2803* (2013.01); *A61P 35/02* (2018.01); *C07K 16/28* (2013.01); *C07K 16/2896* (2013.01); *C07K 16/30* (2013.01); *C12N 5/0093* (2013.01); *C12N 5/0694* (2013.01); *C12Q 1/6886* (2013.01); *G01N 33/5011* (2013.01); *G01N 33/57426* (2013.01); *A61K 2039/505* (2013.01); *A61K 2039/507* (2013.01); *C07K 2317/24* (2013.01); *C07K 2317/73* (2013.01); *C07K 2317/75* (2013.01); *C07K 2317/76* (2013.01); *C12Q 2600/112* (2013.01); *C12Q 2600/136* (2013.01); *G01N 2500/04* (2013.01)

(58) Field of Classification Search
CPC ............... C07K 16/2803; C07K 16/28; C07K 16/2896; C07K 16/30; C07K 2317/24; C07K 2317/73; C07K 2317/75; C07K 2317/76; A61P 35/02; A61K 2039/505; A61K 2039/507
USPC ...................................................... 424/133.1
See application file for complete search history.

(56) References Cited

U.S. PATENT DOCUMENTS

| 4,867,973 A | 9/1989 | Goers et al. |
| 6,465,247 B1 | 10/2002 | Weissman et al. |
| 6,491,917 B1 | 12/2002 | Thomas et al. |
| 6,733,743 B2 | 5/2004 | Jordan |
| 7,514,229 B2 | 4/2009 | Jamieson et al. |
| 8,361,736 B2 | 1/2013 | Majeti et al. |
| 8,562,997 B2 | 10/2013 | Jaiswal et al. |
| 8,709,429 B2 * | 4/2014 | Majeti .................. C12N 5/0093 435/7.1 |
| 8,758,750 B2 | 6/2014 | Weissman et al. |
| 9,399,682 B2 | 7/2016 | Jaiswal et al. |
| 9,493,575 B2 | 11/2016 | Jaiswal et al. |
| 9,796,781 B2 | 10/2017 | Majeti et al. |
| 10,662,242 B2 | 5/2020 | Majeti et al. |
| 10,781,256 B2 | 9/2020 | Weiskopf |
| 11,072,655 B2 | 7/2021 | Majeti et al. |
| 11,136,391 B2 | 10/2021 | Willingham et al. |

(Continued)

FOREIGN PATENT DOCUMENTS

| EP | 1693385 A1 | 8/2006 |
| EP | 2111869 A1 | 10/2009 |

(Continued)

OTHER PUBLICATIONS

Shi et al. (2020) "The identification of a CD47-blocking "hotspot" and design of a CD47/PD-L1 dual-specific antibody with limited hemagglutination" Signal Transduction and Targeted Therapy 5:16 1-3.

(Continued)

*Primary Examiner* — Yan Xiao
(74) *Attorney, Agent, or Firm* — Pamela J. Sherwood; Bozicevic, Field & Francis LLP

(57) ABSTRACT

Markers of acute myeloid leukemia stem cells (AMLSC) are identified. The markers are differentially expressed in comparison with normal counterpart cells, and are useful as diagnostic and therapeutic targets.

16 Claims, 24 Drawing Sheets

Specification includes a Sequence Listing.

(56) References Cited

U.S. PATENT DOCUMENTS

| | | | |
|---|---|---|---|
| 11,141,480 | B2 | 10/2021 | Majeti et al. |
| 11,377,495 | B2 * | 7/2022 | Majeti ................ G01N 33/5011 |
| 2004/0213792 | A1 | 10/2004 | Clemmons et al. |
| 2005/0118164 | A1 | 6/2005 | Herman |
| 2005/0142539 | A1 | 6/2005 | Herman |
| 2006/0239910 | A1 | 10/2006 | Nicolaides et al. |
| 2007/0111238 | A1 | 5/2007 | Jamieson et al. |
| 2007/0113297 | A1 | 5/2007 | Yang et al. |
| 2007/0287163 | A1 | 12/2007 | Geuijen et al. |
| 2008/0107654 | A1 | 5/2008 | Kikuchi |
| 2008/0131431 | A1 | 6/2008 | Smith et al. |
| 2008/0187950 | A1 | 8/2008 | Weissman et al. |
| 2009/0191202 | A1 | 7/2009 | Jamieson et al. |
| 2010/0255575 | A1 | 10/2010 | Weissman et al. |

FOREIGN PATENT DOCUMENTS

| | | | |
|---|---|---|---|
| JP | 20010503253 | A | 3/2001 |
| JP | 2003518514 | A | 6/2003 |
| JP | 20040504408 | A | 2/2004 |
| JP | 20050333993 | A | 12/2005 |
| JP | 6280161 | B2 | 2/2018 |
| WO | 1999/10478 | A1 | 3/1999 |
| WO | 1999/040940 | A1 | 8/1999 |
| WO | 2003/074567 | A2 | 9/2003 |
| WO | 2005/044857 | A1 | 5/2005 |
| WO | 2007/0121465 | A2 | 10/2007 |
| WO | 2007/133811 | A2 | 11/2007 |
| WO | 2009/046541 | A1 | 4/2009 |
| WO | 2009/091547 | A1 | 7/2009 |
| WO | 2009/091601 | A1 | 7/2009 |
| WO | 2006/089133 | A2 | 8/2009 |
| WO | 2009/131453 | A1 | 10/2009 |
| WO | 2010/017332 | A2 | 2/2010 |
| WO | 2011/0034969 | A1 | 3/2011 |
| WO | WO 2011/143624 | | 11/2011 |

OTHER PUBLICATIONS

Agerstam et al. (2015) "Antibodies targeting human II1RAP (IL1R3) show therapeutic effects in xenograft models of acute myeloid leukemia" Proceedings of the National Academy of Sciences 112:34 10786-10791.

Clarke et al. (2006) "Cancer stem cells—perspectives on current status and future directions: AACR Workshop on cancer stem cells" Cancer Research 66:19 9339-9344.

Coiffier (2005) "State-of-the-Art Therapeutics: Diffuse Large B-Cell Lymphoma" Journal of Clinical Oncology 23:26 6387-6393.

Gleason et al. (2012) "Tim-3 is an inducible human natural killer cell receptor that enhances interferon gamma production in response to galectin-9" Blood 1-42.

Akashi et al., "A clonogenic common myeloid progenitor that gives rise to all myeloid lineages", Nature,Mar. 9, 2000, p. 193-197, 404(6774), Macmillan Publishing, Basingstoke, United Kingdom.

Baxter et al., "Acquired mutation of the tyrosine kinase JAK2 in human myeloproliferative disorders", Lancet, Mar. 19-25, 2005, pp. 1054-1061, vol. 365, Issue 9464, Elsevier, Amsterdam, Netherlands.

Brooke et al., "Human Lymphocytes Interact Directly with CD47 Through a Novel Member of the Signal Regulatory Protein (SIRP) Family", J Immunol., Aug. 15, 2004, pp. 2562-2570, vol. 173, Issue 4, American Association of Immunologists, Rockville, MD.

Chan et al., "Identification, molecular characterization, clinical prognosis, and therapeutic targeting of human bladder tumor-initiating cells", PNAS, Aug. 18, 2009, pp. 14016-14021, vol. 106 No. 33, National Academy of Sciences, Washington, D.C.

Conrad et al., "Inflammatory cytokines predominate in cases of tumor regression after hematopoietic stem cell transplantation for solid cancer", Biol Blood Marrow Transplant, Mar. 2006, pp. 346-354, vol. 12, Issue 3, Elsevier, Amsterdam, Netherlands.

Demeure et al., "CD47 Engagement inhibits cytokine production and maturation of human dendritic cells", J Immunol Feb. 15, 2000, pp. 2193-2199, vol. 164, Issue 4, American Association of Immunologists, Rockville, MD.

Durando et al., "High-dose BCNU followed by autologous hematopoietic stem cell transplantation in supratentorial high-grade malignant gliomas: a retrospective analysis of 114 patients", Bone Marrow Transplant, Apr. 2003, pp. 559-564, 31(7), Nature Publishing Group, London, United Kingdom.

Eichler et al., "CD97 isoform expression in leukocytes", J Leukoc Biol., Oct. 2000, pp. 561-567, vol. 68 No. 4, Society for Leukocyte Biology, Bethesda, MD.

Fey, "ESMO Minimum Clinical Recommendations for diagnosis, treatment and follow-up of acute myeloblastic leukaemia (AML) in adult patients", Annals of Oncology, Aug. 1, 2003, pp. 1161-1162, vol. 14, Issue 8, Oxford University Press, Oxford, United Kingdom.

Fuchs et al., "Cutting Edge: CD96 (Tactile) Promotes NK Cell-Target Cell Adhesion by Interacting with the Poliovirus Receptor (CD155)", J Immunol., Apr. 1, 2004,pp. 3394-3398, vol. 172, Issue 7, American Association of Immunologists, Rockville, MD.

Gleason et al., "Tim-3 is an inducible human natural killer cell receptor that enhances interferon gamma production in response to galectin-9", Blood, Feb. 2012, pp. 3064-3072, vol. 119, Issue 13,The American Society of Hematology, Washington, D.C.

Hebeis et al., "Vav proteins are required for B-lymphocyte responses to LPS", Blood, Jul. 2005, pp. 635-640, vol. 106, Issue 2, The American Society of Hematology, Washington, D.C.

Hosen et al., "CD96 is a leukemic stem cell-specific marker in human acute myeloid leukemia", PNAS, Jun. 26, 2007, pp. 11008-11013, vol. 104 No. 26, National Academy of Sciences, Washington, D.C.

Imbert et al., "CD99 expressed on human mobilized peripheral blood CD34+ cells is involved in transendothelial migration", Blood (Oct. 2006), pp. 2578-2586, vol. 108, Issue 8, The American Society of Hematology, Washington, D.C.

Imayoshi et al., "Expression of CD180, a toll-like receptor homologue, is up-regulated in children with Kawasaki disease", J Mol Med., Feb. 2006, pp. 168-174, vol. 84, Issue 2, Springer Publishing, New York, NY.

James et al., "A unique clonal JAK2 mutation leading to constitutive signaling causes polycythaemia vera", Nature, Apr. 28, 2005, pp. 1144-1148, 434(7037), Nature Publishing Group, London, United Kingdom.

Jamieson et al., "Chronic versus acute myelogenous leukemia: A question of self-renewal", Cancer Cell, Dec. 2004, pp. 531-533, vol. 6, Issue 6, Elsevier, Amsterdam, Netherlands.

Jamieson et al., "Granulocyte-macrophage progenitors as candidate leukemic stem cells in blast-crisis CML", N Engl J Med, Aug. 12, 2004, pp. 657-667, 351(7), Massachusetts Medical Society, Waltham, MA.

Jamieson et al., "Increased expression of CD47 is a constant marker in mouse and human myeloid leukemias", Blood (ASH Annual Meeting abstracts), Jan. 2005, Abstract p. 3260, vol. 106, Issue 11, The American Society of Hematology, Washington, D.C.

Jan et al., "Prospective separation of normal and leukemic stem cells based on differential expression of TIM3, a human acute myeloid leukemia stem cell marker", PNAS, Mar. 22, 2011, pp. 5009-5014, vol. 108 No. 12, National Academy of Sciences, Washington, D.C.

Jin et al., "Targeting of CD44 eradicates human acute myeloid leukemic stem cells", Nat Med., Oct. 2006, pp. 1167-1174, 12(10), Macmillan Publishing, Basingstoke, United Kingdom.

Kikushige et al., "TIM-3 Is a Promising Target to Selectively Kill Acute Myeloid Leukemia Stem Cells", Cell Stem Cell, Dec. 3, 2010, pp. 708-717, vol. 7, Issue 6, Elsevier, Amsterdam, Netherlands.

Kralovics et al., "A gain-of-function mutation of JAK2 in myeloproliferative disorders", N Engl J Med., Apr. 28, 2005, pp. 1779-1790, 352(17), Massachusetts Medical Society, Waltham, MA.

Levine et al., "Activating mutation in the tyrosine kinase JAK2 in polycythemia vera, essential thrombocythemia, and myeloid metaplasia with myelofibrosis", Cancer Cell, Apr. 2005, pp. 387-397, vol. 7, Issue 4, Elsevier, Amsterdam, Netherlands.

Liu et al., "Signal Regulatory Protein (SIRPalpha), a Cellular Ligand for CD47, Regulates Neutrophil Transmigration", J Biol

(56) References Cited

OTHER PUBLICATIONS

Chem., Mar. 22, 2002, pp. 10028-10036, 227(12), American Society for Biochemistry and Molecular Biology, Rockville, MD.
Majeti et al., "CD47 is an adverse prognostic factor and therapeutic antibody target on human acute myeloid leukemia stem cells", Cell, Jul. 23, 2009, pp. 286-299, vol. 138, Issue 2, Elsevier, Amsterdam, Netherlands.
Majeti et al., "CD47 Is An Independent Prognostic Factor and Therapeutic Antibody Target on Human Acute Myeloid Leukemia Stem Cells", Blood, 2008, Abstract p. 766,112, The American Society of Hematology, Washington, D.C.
Manna et al., "CD47 mediates killing of breast tumor cells via Gi-dependent inhibition of protein kinase A", Cancer Res., Feb. 2004, pp. 1026-1036, vol. 64, Issue 3, American Association for Cancer Research, Philadelphia, PA.
McDonald et al., "Cholesterol-independent interactions with CD47 enhance alphavbeta3 avidity", J Biol Chem., Apr. 23, 2004, pp. 17301-17311, 279(17), American Society for Biochemistry and Molecular Biology, Rockville, MD.
Passegue et al., "JunB deficiency leads to a myeloproliferative disorder arising from hematopoietic stem cells", Cell, Oct. 29, 2004, pp. 431-443, vol. 119, Issue 3, Elsevier, Amsterdam, Netherlands.
Pettersen et al., "CD47 signals T cell death", J Immunol., Jun. 15, 1999, pp. 7031-7040, vol. 162, Issue 12, American Association of Immunologists, Rockville, MD.
Subramanian et al., "Species- and cell type-specific interactions between CD47 and human SIRPalpha", Blood, Mar. 2006, pp. 2548-2556, vol. 107, Issue 6, The American Society of Hematology, Washington, D.C.
Sutherland et al., "Characterization of a hierarchy in human acute myeloid leukemia progenitor cells", Blood, Jun. 1996, pp. 4754-4761, vol. 87, Issue 11, The American Society of Hematology, Washington, D.C.
Willingham et al., "The CD47-signal regulatory alpha (SIRPa) interaction is a therapeutic target for human solid tumors", PNAS, Apr. 24, 2012, pp. 6662-6667, vol. 109 No. 17, National Academy of Sciences, Washington, D.C.
Chao et al., "Therapeutic antibody targeting of CD47 eliminates human acute lymphoblastic leukemia", Cancer Res., Feb. 2011, pp. 1374-1384, vol. 71, Issue 4, American Association for Cancer Research, Philadelphia, PA.
Jaiswal et al., "Macrophages as mediators of tumor immunosurveillance", Trends Immunol., Jun. 2010, pp. 212-219, vol. 31, Issue 6, Elsevier, Amsterdam, Netherlands.
Manna et al., "The mechanism of CD47-dependent killing of T cells: heterotrimeric Gi-dependent inhibition of protein kinase A", J Immunol., Apr. 1, 2003 (2003), pp. 3544-3553, vol. 170, Issue 7, American Association of Immunologists, Rockville, MD.
Zhao et al., "CD47-signal regulatory protein-a (SIRPa) interactions form a barrier for antibody-mediated tumor cell destruction", Proc Natl Acad Sci U S A, Nov. 8, 2011, pp. 18342-18347, vol. 108 No. 45, National Academy of Sciences, Washington, D.C.
Zhao et al., "Is targeting of CD47-SIRPa enough for treating hematopoietic malignancy?", Blood, 2012, pp. 4333-4334, vol. 119, Issue 18, he American Society of Hematology, Washington, D.C.
Tioma Therapeutics, Inc., Notice of Opposition to European Patent EP2242512, Jan. 20, 2017, pp. 1-40.
Blink Biomedical SAS, Notice of Opposition to European Patent EP2242512, Jan. 26, 2017, pp. 1-42.
Bristol-Myers Squibb Company, Notice of Opposition to to European Patent European Patent EP2242512, Jan. 26, 2017, pp. 1-29.
Avidity IP Limited, Notice of Opposition to European Patent EP2242512, Jan. 26, 2017, pp. 1-36.
Wilding, Notice of Opposition to European Patent EP2242512, Jan. 26, 2017, pp. 1-52.
Surface Oncology, Inc., Notice of Opposition to European Patent EP2242512, Jan. 27, 2017, pp. 1-45.
Strawman Limited, Notice of Opposition to European Patent EP2242512, Jan. 27, 2017, pp. 1-36.

Wiesenthal, Human Tumor Assay Journal, Mar. 14, 2012, on-line at http://weisenthal.org/synergy1.htm, p. 1.
Berenbaum, "Synergy, additivism and antagonism in immunosuppression. A critical review", Clin exp Immunol, Apr. 1997, pp. 1-18, 28(1), Wilely, Hoboken, NJ.
Harmsen et al., "Properties, production, and applications of camelid single-domain antibody fragments", Applied Microbiology and Biotechnology, Nov. 2007, pp. 13-22, vol. 77, Issue 1, Springer Publishing, New York, NY.
Zegers et al., "Studies on Fd Fragments of Human Immunoglobulins", Scand. J. Immunol., Mar. 1975, pp. 161-169, vol. 4, Issue 2, Wilely, Hoboken, NJ.
Valneva Austria GMBH, Third Party Observation for Publication No. EP2242512, Filed on Jan. 15, 2009, 4 Pages.
Jamieson et al., "Increased Ecpression of CD47 is a Constant Marker in Mouse and Human Myelodi Leukemias" Blood (ASH Annual Meeting Abstracts), 2005, pp. 1-2, 106, Abstract 3260, American Society of Hematology, Washington, DC.
Clynes et al., "Inhibitory Fc Receptors Modulate in vivo Cytoxicity Against Tumor Targets" Nature Medicine, Apr. 2000, pp. 443-446, vol. 6, No. 4, Nature America, Inc., New York, NY.
Arsenijevic et al., "Phagocytic Activity of Monocytes in Patients with Breast Cancer at Different Clinical Stages", Breast Cancer Research, Jun. 2001, pp. S1-S24, Abstract "A4" vol. 3 Suppl 1, 23rd Congress of the International Association for Breast Cancer Research, Düsseldorf, Germany.
Oldenborg et al., "Role of CD47 as a Marker of Self on Red Blood Cells", Science, Jun. 16, 2000, pp. 2051-2054, vol. 288, No. 5473, American Association for the Advancement of Science, Washington, D.C.
Gokbuget et al., "Novel Antibody-Based Therapy for Acute Lymphoblastic Leukaemia", Best Practice & Research Clinical Haematology, 2006, pp. 701-713, vol. 19, Elsevier Ltd., Atlanta, GA.
Younes et al., "A Pilot Study of Rixuximab in Patents with Recurrent, Classic Hodgkin Disease", Cancer, 2003, pp. 310-314, vol. 98, American Cancer Society, Atlanta, GA.
Beuzeboc et al., "Trastuzmab (T) combined with standard chemotherapy in HER+ metastic bladder cancer (BC) patients: Interim safety results of a prospective randomized phase II study", Journal of Clinical Oncology, Abstract, Jun. 2007, vol. 25, No. 18S, American Society of Clinical Oncology.
Mawby et al., "Isolation and characterization of CD47 glycoprotein: a multispanning membrane protein which is the same as integrin-associated protein (IAP) and the ovarian tumour marker OA3", The Biochemical Journal, 1994, pp. 525-530, vol. 304, Portland Press, London, England.
Bookman et al., "Evaluation of Monoclonal Humanized Anti-HER2 Antibody, Trastuzumab, in Patients With Recurrent or Refractory Ovarian or Primary Peritoneal Carcinoma With Over expression of HER2: A Phase II Trial of the Gynecologic Oncology Group", Journal of Clinical Oncology, Jan. 15, 2003, pp. 283-290, vol. 21, American Society of Clinical Oncology, Alexandria, VA.
Kovacsovics-Bankowski et al., "Efficient major histocompatibility complex class I presentation of exogenous antigen upon phagocytosis by macrophages", Proc. Natl. Acad. Sci., 1993, pp. 4942-4946, vol. 90, PNAS, Washington, DC.
NCBI protein database-SIRP alpha (Jun. 6, 2006).
Gibson et al., "Phase III Trial of a Humanized Anti-CD33 Antibody (HuM195) in Patients with Relapsed or Refractory Acute Myeloid Leukemia", Clin Lymphoma, Jun. 2002, pp. 18-19, vol. 3, Issue 1, Elsevier, Amsterdam, Netherlands.
Alinari et ai.,"Aiemtuzumab (Campath-1 H) in the treatment of chronic lymphocytic leukemia", Oncogene, 2007, pp. 3644-3653, 26, Nature Publishing Group, London, United Kingdom.
Burger et al., "Phase II Trial of Bevacizumab in Persistent or Recurrent Epithelial Ovarian Cancer or Primary Peritoneal Cancer: A Gynecologic Oncology Group Study", Journal Of Clinical Oncology, Nov. 20, 2007, pp. p165-5172, vol. 25, No. 33, American Society of Clinical Oncology, Alexandria, VA.
Clynes et al., "Inhibitory Fe receptors modulate in vivo cytoxicity against tumor targets", Nature Medicine, Apr. 2000, pp. 443-446, vol. 6, No. 4, Nature Publishing Group, London, United Kingdom.

(56) References Cited

OTHER PUBLICATIONS

Curriculum Vitae Randolph Wall, Ph.D., Filed: Aug. 5, 2016, 9 pages.
Declaration of Randolph Wall, Ph.D., Filed: Aug. 5, 2016, 107 Pages.
Imai et al., "Comparing antibody and small-molecule therapies for cancer", Nature Reviews/Cancer, Sep. 2006, pp. 714-727, vol. 6, Nature Publishing Group, London, United Kingdom.
Kim et al., "Antibody Engineering for the Development of Therapeutic Antibodies", Molecules and Cells, Aug. 18, 2005, pp. 17-29, vol. 20, No. 1, Korean Society for Molecular and Cellular Biology, Seoul, Korea.
Mawby et al., "Isolation and characterization of CD47 glycoprotein: a multispanning membrane protein which is the same as integrin-associated protein (IAP) and the ovarian tumour marker OA3", Biochem. J., 1994, pp. 525-530, 304, Portland Press Limited, London, United Kingdom.
Musolino et al., Immunoglobulin G Fragment C Receptor Polymorphisms and Clinical Efficacy of Trastuzumab-Based Therapy in Patients With HER-2/neu-Positive Metastatic Breast Cancer, Journal Of Clinical Oncology, Apr. 10, 2008, pp. 1789-1796, vol. 26, No. 11, American Society of Clinical Oncology, Alexandria, VA.
Okazawa et al., "Negative Regulation of Phagocytosis in Macrophages by the CD47-SHPS-1 System", The Journal of Immunology, 2005, pp. 2004-2011, 174, The American Association of Immunologists, Inc., Bethesda, MD.
Oldenborg et al., "CD47-Signal Regulatory Protein a (SIRPa) Regulates Fey and Complement Receptor-mediated Phagocytosis", J. Exp. Med., Apr. 2, 2001, pp. 855-861, vol. 193, No. 7, The Rockefeller University Press, New York, NY.
Ozols, "Challenges for chemotherapy in ovarian cancer", Annals of Oncology, May 2006, pp. v181-v187, vol. 17, Supplement 5, European Society for Medical Oncology, Lugano, Switzerland.
Forty Seven, Inc., Petition For Inter Partes Review of U.S. Pat. No. 9,352,037, filed Aug. 5, 2016, Case No. PR2016-01529, 74 Pages.
Forty Seven, Inc., Petition For Inter Partes Review of U.S. Pat. No. 9,352,037, filed Aug. 8, 2016, Case No. PR2016-01530, 76 Pages.
Tibes et al., "Activity of Alemtuzumab in Patients with CD52-Positive Acute Leukemia", Cancer, Jun. 15, 2006, pp. 645-2651, vol. 106, No. 12, American Cancer Society, Atlanta, GA.
Veillette et al., "High Expression of Inhibitory Receptor SHPS-1 and Its Association with Protein-tyrosine Phosphatase SHP-1 in Macrophages", The Journal of Biological Chemistry, Aug. 28, 1998, pp. 22719-22728, vol. 273, No. 35, The American Society for Biochemistry and Molecular Biology, Inc., Rockville, MD.
Zheng et al., "Gene expression profiling of CD34~ cells identifies a molecular signature of chronic myeloid leukemia blast crisis", Leukemia, Apr. 13, 2006, pp. 1028-1034, 20, Nature Publishing Group, London, United Kingdom.
White et al., "Monoclonal antibodies inhibit prion replication and delay the development of prion disease", Nature, 2003, p. 80-83, vol. 422, Nature Publishing Group, London, United Kingdom.
Motegi et al., Role of the CD47-SHPS-1 system in regulation of cell migration, EMBO Journal, 2003, pp. 634-2644, vol. 22, No. 11, European Molecular Biology Organization, Heidelberg, Germany.
Shahan et al., "Identification of CD47/Integrin-associated Protein and av83 as Two Receptors for the a3(1V) Chain of Type IV Collagen on Tumor Cells", Cancer Research, Sep. 15, 1999, pp. 4584-4590, vol. 59, American Association for Cancer Research, Philadelphia, PA.
Ouban et al., "Expression and Distribution of Insulin-Like Growth Factor-1 Receptor in Human Carcinomas", Human Pathology, Aug. 2003, pp. 803-808, vol. 34, No. 8, Elsevier, Amsterdam, Netherlands.
Schlom, "Monoclonal Antibodies: They're More and Less Than You Think", In: Molecular Foundations of Oncology, 1991, pp. 95-134, Williams & Wilkins, Baltimore, MD.
Ishikawa et al., "Chemotherapy-resistant human AML stem cells home to and engraft within the bone-marrow endosteal region", Nature Biotechnology, Nov. 2007, pp. 1315-1321, vol. 25, Nature Publishing Group, London, United Kingdom.
Levesque et al., "Mobilization of bone marrow-derived progenitors", In: "Bone Marrow-Derived Progenitors", Handbook of Experimental Pharmacology, 2007, pp. 3-36, vol. 180, Springer, Salmon Tower Building, New York City.
Matsuo et al., "Two acute monocytic leukemia (AML-M5a) cell lines (MOLM-13 and MOLM-14) with interclonal phenotypic heterogeneity showing MLL-AF9 fusion resulting from an occult chromosome insertion, ins(11 ;9)(q23;p22p23)", Leukemia, 1997, pp. 1469-1477, vol. 11, Stockton Press, Amsterdam, The Netherlands.
McCormack et al., "Animal models of acute myelogenous leukaemia-development, application and future perspectives", Leukemia, 2005, pp. 687-706, vol. 19, Nature Publishing Group, London, United Kingdom.
Mazurier et al., "A Novel Immunodeficient Mouse Model-RAG2 X Common Cytokine Receptor y Chain Double Mutants-Requiring Exogenous Cytokine Administration for Human ~ Hematopoietic Stem Cell Engraftment", Journal of Interferon and Cytokine Research, 1999, pp. 533-541, vol. 19, Mary Ann Liebert, Inc., New Rochelle, NY.
Vigna et al., "Robust and Efficient Regulation of Transgene Expression in Vivo by Improved Tetracycline-Dependent Ientiviral Vectors", Molecular Therapy, 2002, pp. 252-261, vol. 5, The American Society of Gene Therapy, Milwaukee, WI.
Hatherley et al., "Paired Receptor Specificity Explained by Structures of Signal Regulatory Proteins Alone and Complexed with CD47", Molecular Cell, Jul. 25, 2008, pp. 266-277, vol. 31, Elsevier, New York City, NY.
Ide et al., "Role for CD47-SIRP [alpha] signaling in xenograft rejection by macrophages", PNAS, Mar. 20, 2007, pp. 5062-5066, vol. 104, No. 12, National Academy of Sciences, Washington, D.C.
Metayer et al., "Anti-CD47 antibodies induce phagocytosis of live, malignant B cells by macrophages via Fc domain, resulting in cell death by phagoptosis", Oncotarget, Sep. 5, 2017, pp. 60892-60903, vol. 8(37), National Center for Biotechnology Information, Bethesda MD.
Pettersen, "CD47 and death signaling in the immune system", Apoptosis, Oct. 2000, pp. 299-306, vol. 5(4), Springer, Berlin, Germany.
Pietsch et al., "Anti-leukemic activity and tolerability of anti-human CD47 monoclonal antibodies", Blood Cancer Journal, Feb. 24, 2017, pp. 1-25, vol. 7(e536), Macmillan Publishers Limited, Basingstoke, United Kingdom.
Tioma Threapeutics, Oral Proceedings—Opposition against EP2242512, Cover letter, Submission and references D100, D101, D102 and D103 cited in cover letter, Jun. 27, 2018, 22 pages.
Martin-Subero et al., "Amplification of ERBB2, RARA, and TOP2A genes in a myelodysplastic syndrome transforming to acute myeloid leukemia", Cancer Genetics and Cytogenetics, Jun. 2001, pp. 174-176, vol. 127, Issue 2, Elsevier, Amsterdam, Netherlands.
Agerstam et al. "Antibodies targeting human ILIRAP (IL1R3) show therapeutic effects in xenograft models of acute myeloid leukemia" A Proceedings of The National Academy Of Sciences, vol. 112. No. 34. pp. 10786-10791.
Cullinan et al. "IL-1 Receptor 1 Accessory Protein Is an Essential Component of the IL-I Receptor" The Journal of Immunology, p. 5614.
Boyd-Kirkup et al., (2017) "HMBD004, a Novel Anti-CD47xCD33 Bispecific Antibody Displays Potent Anti-Tumor Effects in Pre-Clinical Models of AML,"Blood, 2017, 130: suppl. 1, abstract, p. 1378.
Chari et al., (2014) "Antibody-Drug Conjugates: An Emerging Concept in Cancer Therapy" Angew Chem Int Ed Engl. 53: 3796-3827.
Jalil et al., (2020) "Macrophage checkpoint blockade: results from initial clinical trials, binding analyses, and CD47-SIRPα structure-function" Antibody Therapeutics, 3: pp. 80-94.
Lu et al., (2020) "Potential New Cancer Immunotherapy: Anti-CD47-SIRPα Antibodies" Oncotargets and Therapy, 2020, 13: 9323-9331.

(56) References Cited

OTHER PUBLICATIONS

Piccione et al., (2015) "A bispecific antibody targeting CD47 and CD20 selectively binds and eliminates dual antigen expressing lymphoma cells" mAbs, 7: 946-956.

Qu, (2022) "Targeting CD47/SIRPα as a therapeutic strategy, where we are and where we are headed" Biomarker Research, 10:20, 18 pages.

Sailman et al., (2019) "The first-in-class anti-CD47 antibody Hu5F9-G4 is active and well tolerated alone or with azacitidine in AML and MDS patients: Initial phase 1b results" Journal of Clinical Oncology, 37:15, suppl., abstract No. 7009.

Shlush et al., (2017) "Tracing the origins of relapse in acute myeloid leukaemia to stem cells" Nature, 547: 104-110 plus extended data, 10 pages.

Whiteman et al., (2014) "IMGN779: A CD33-Targeted Antibody-Drug Conjugate (ADC) Utilizing a Novel DNA Alkylator, DGN462, Is Highly Active In vitro Against Primary Patient AML Cells and In Vivo Against AML Xenografts in Mice," Haematologica, 99: suppl. 1, pp. 293, Abstract No. P802.

Valent et al., (2020) "Cell-based and antibody-mediated immunotherapies directed against leukemic stem cells in acute myeloid leukemia: Perspectives and open issues" Stem Cells Translational Medicine 9:1331-1343.

Zeidan et al., (2022) "Phase 1 study of anti-CD47 monoclonal antibody CC-90002 in patients with relapsed/refractory acute myeloid leukemia and high-risk myelodysplastic syndromes" Annals of Hematology, vol. 101: 557-569.

Gardai et al., (2005) "Cell-surface calreticulin initiates clearance of viable apoptotic cells through trans-activation of LRP on the phagocyte." Cell Elsevier, vol. 123, pp. 321-334.

Jaiswal et al., (2009) "CD47 Is Upregulated on Circulating Hematopoietic Stem Cells and Leukemia Cells to Avoid Phagocytosis", Cell, Cell Press, vol. 138, No. 2, pp. 271-285.

\* cited by examiner

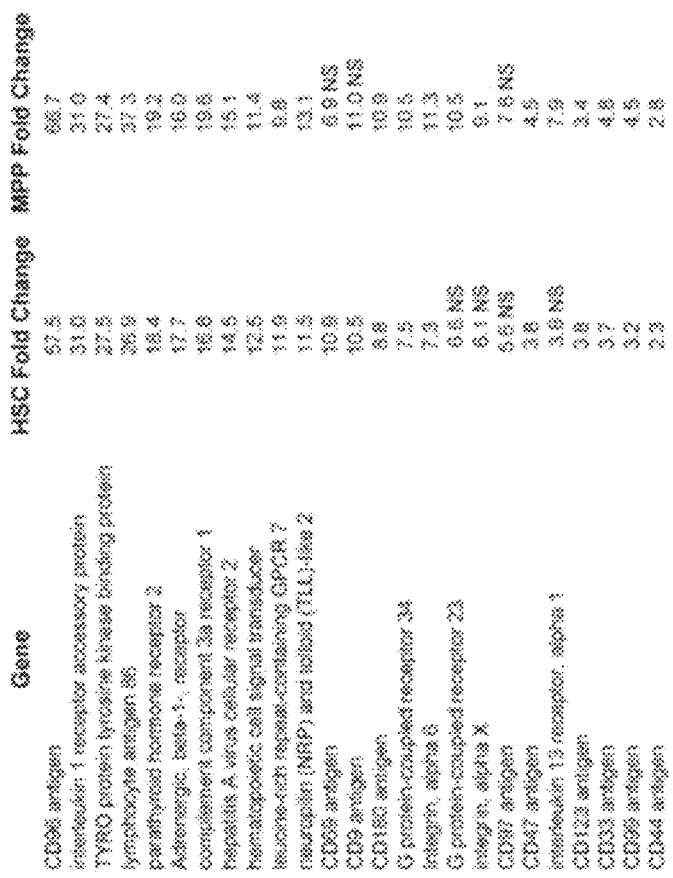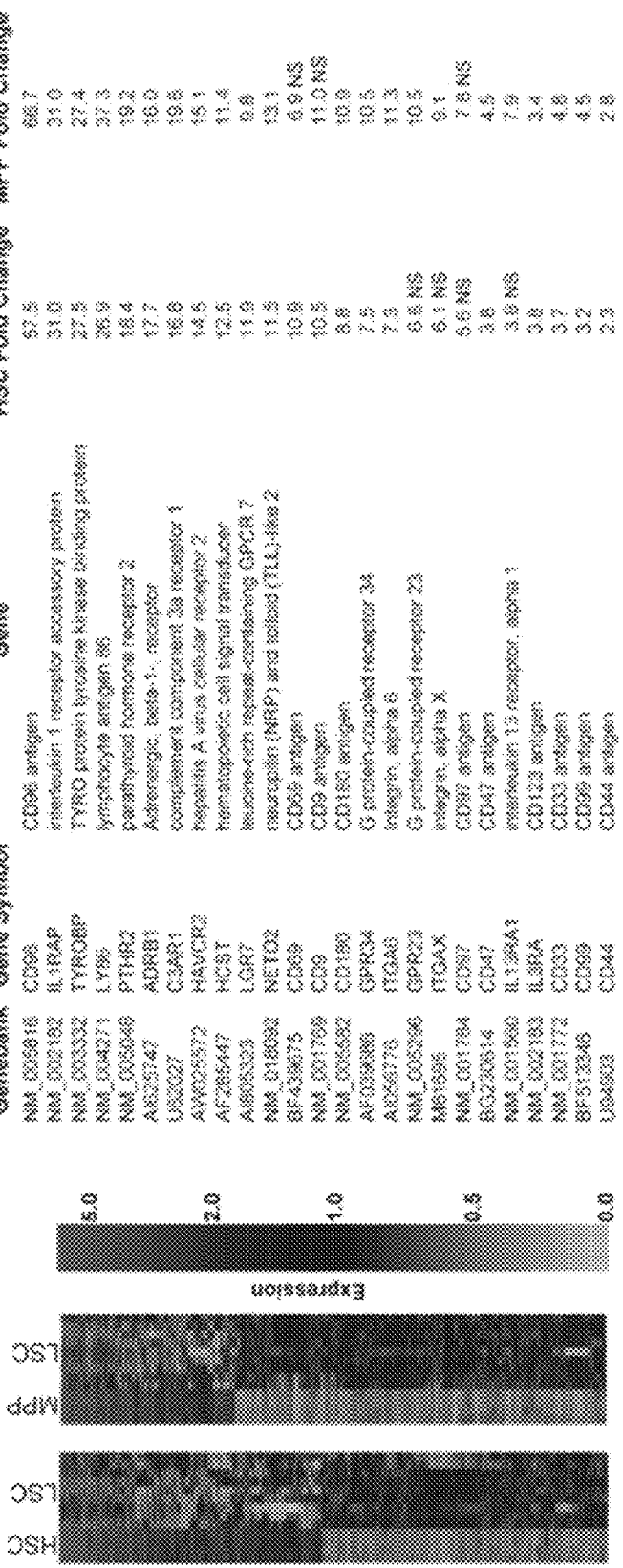

Figure 3A            Figure 3B
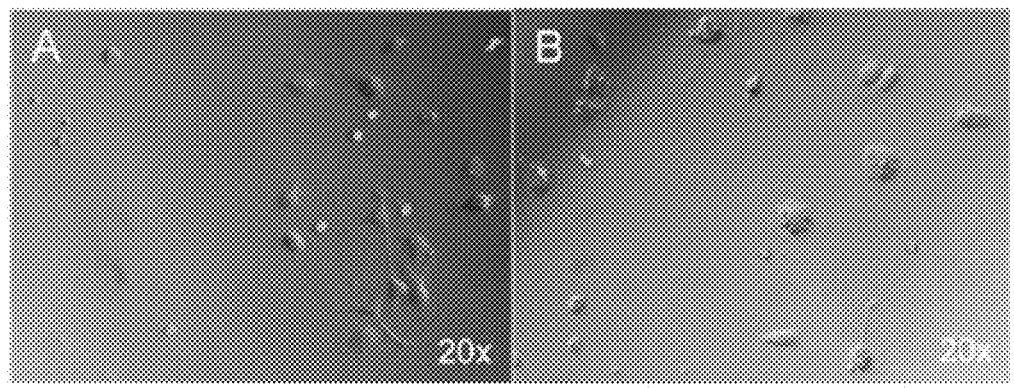
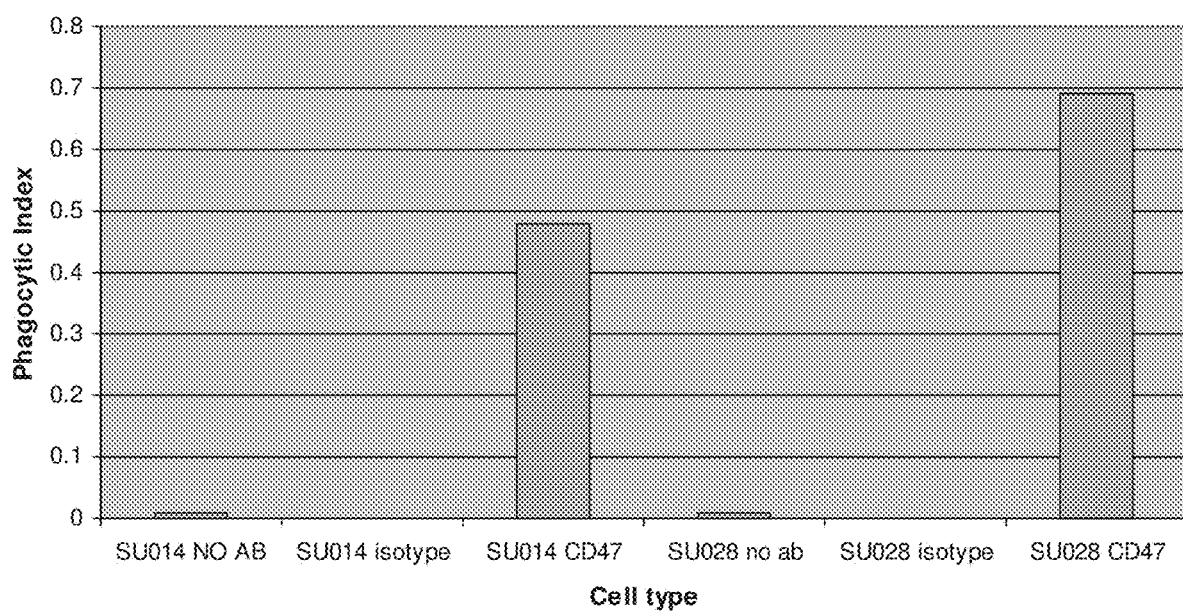
Figure 3C

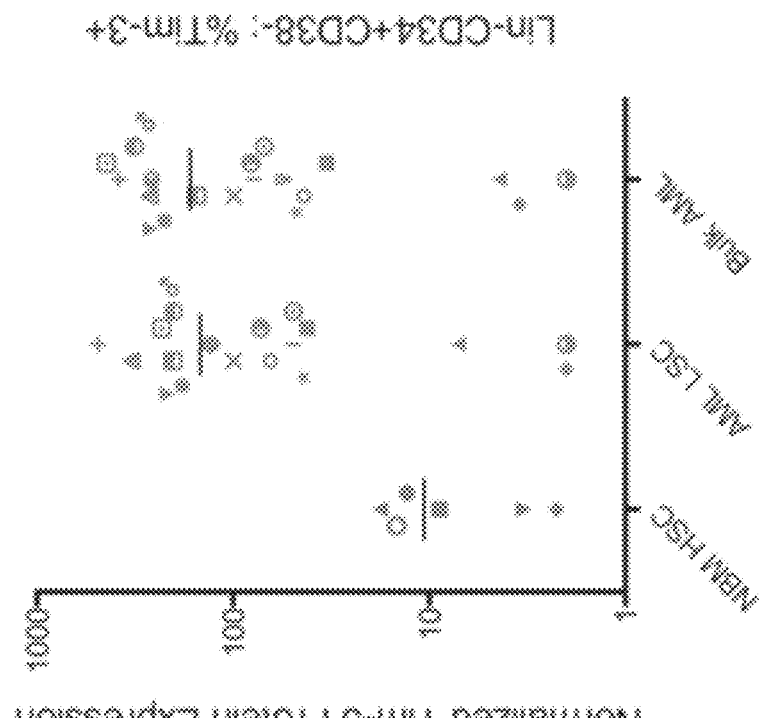
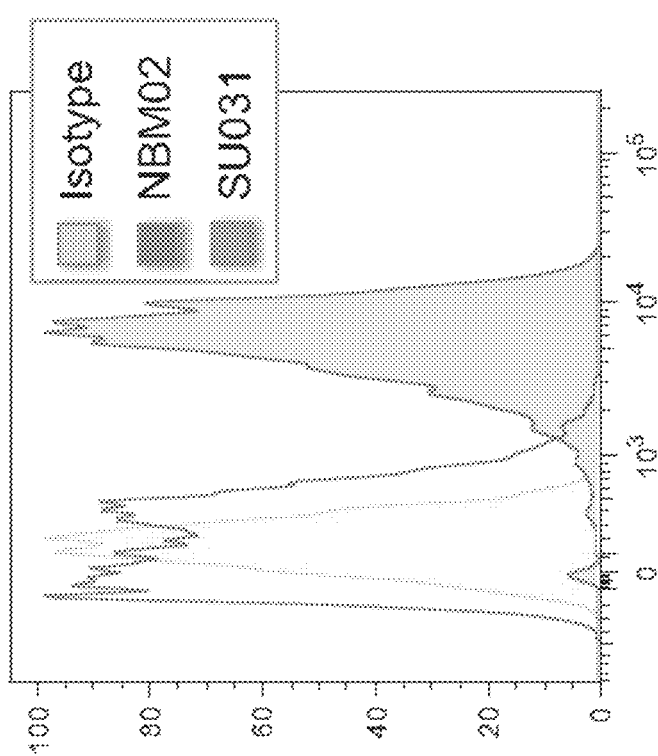
Figure 11A
Figure 11B

Figure 12B
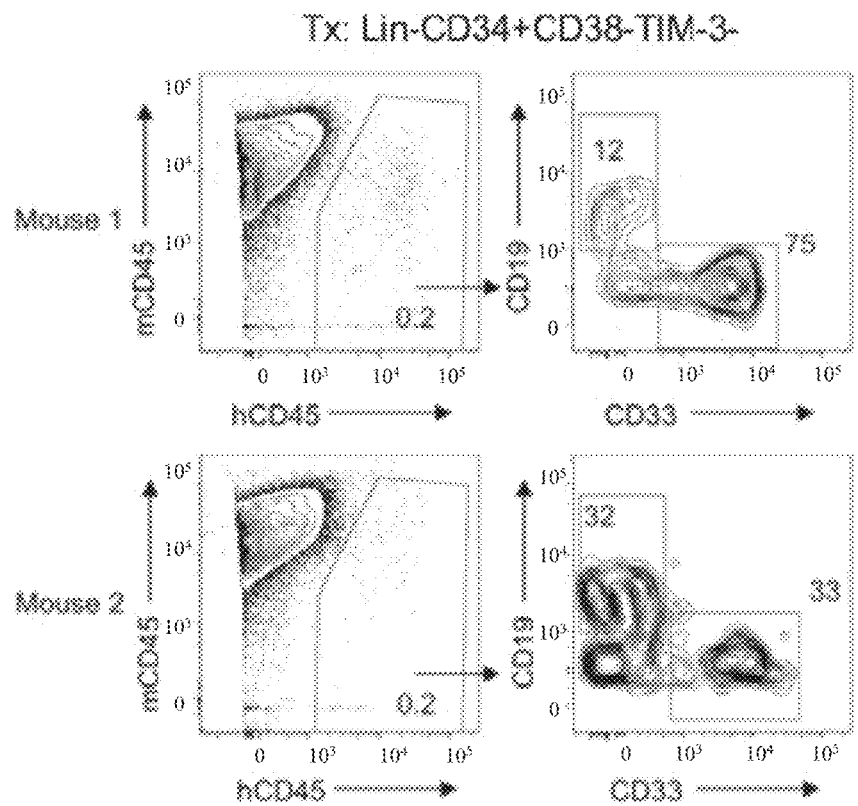
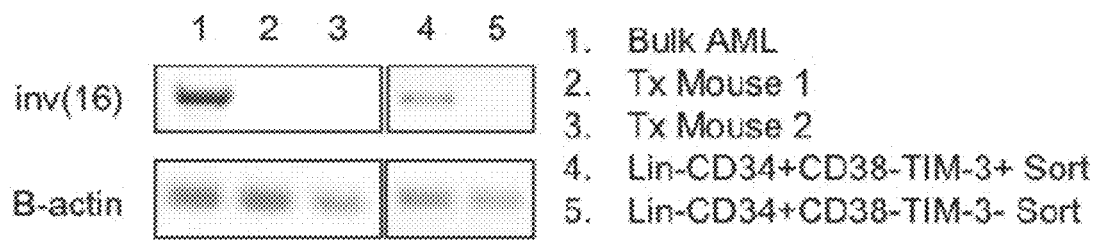
Figure 12C

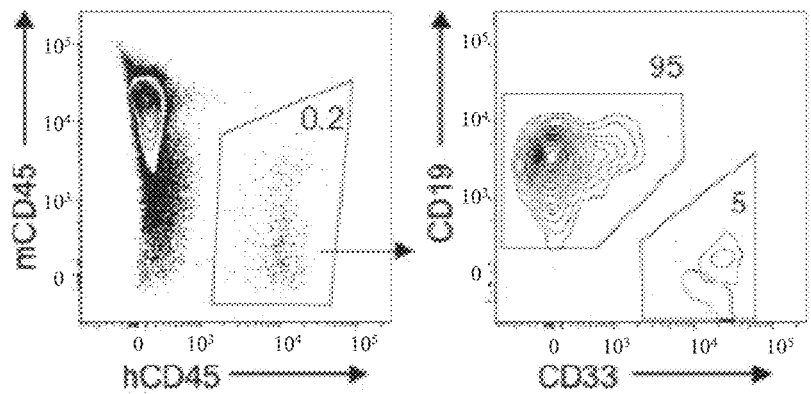
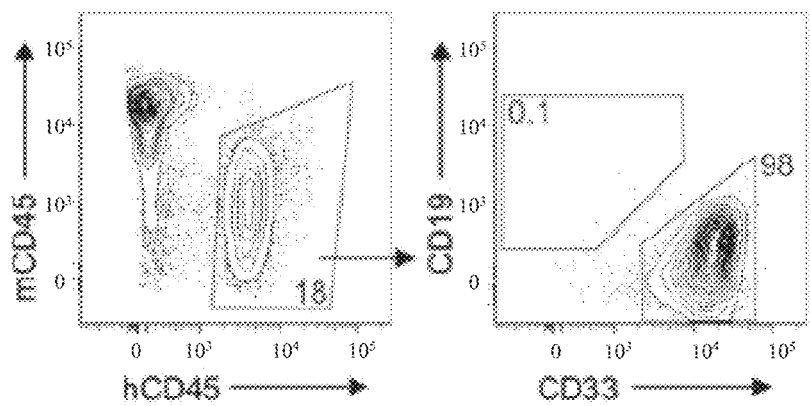
| Lin-CD34+CD38-<br>AML Fraction Tx | TIM-3- | TIM-3- | |
|---|---|---|---|
| Cell dose | 400 | 20,000 | 200,000 |
| CD19+; CD33+ | 2/4 | 0/2 | 0/2 |
| CD33+ | 0/4 | 2/2 | 2/2 |
Figure 13C

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: synthetic primer

<400> SEQUENCE: 1
gggctgtctg gagtttgatg                                              20

<210> SEQ ID NO 2
<211> LENGTH: 22
<212> TYPE: DNA
<213> ORGANISM: Artificial Sequence
<220> FEATURE:
<223> OTHER INFORMATION: synthetic primer

<400> SEQUENCE: 2
tcctcttctc ctcattctgc tc                                           22

<210> SEQ ID NO 3
<211> LENGTH: 23
<212> TYPE: DNA
<213> ORGANISM: Artificial Sequence
<220> FEATURE:
<223> OTHER INFORMATION: synthetic primer

<400> SEQUENCE: 3
gcaatttagg tatgaaagcc agc                                          23

<210> SEQ ID NO 4
<211> LENGTH: 23
<212> TYPE: DNA
<213> ORGANISM: Artificial Sequence
<220> FEATURE:
```

```
<223> OTHER INFORMATION: synthetic primer

<400> SEQUENCE: 4
ctttcagcat tttgacggca acc                                           23
```

MARKERS OF ACUTE MYELOID LEUKEMIA STEM CELLS

CROSS REFERENCE

This application claims benefit and is a Continuation of application Ser. No. 15/704,790, filed Sep. 14, 2017, which is a a Continuation of application Ser. No. 14/927,349 filed Oct. 29, 2015, which is a a Continuation of application Ser. No. 14/164,009 filed Jan. 24, 2014, now U.S. Pat. No. 9,193,955 issued Nov. 24, 2015, which is a a Continuation of application Ser. No. 13/739,788 filed Jan. 11, 2013, now U.S. Pat. No. 8,709,429 issued Apr. 29, 2014, which is a a Continuation of application Ser. No. 12/836,152 filed Jul. 14, 2010, now U.S. Pat. No. 8,361,736 issued Jan. 29, 2013, which is a Continuation in Part and claims the benefit of PCT Application No. PCT/US2009/000224, filed Jan. 13, 2009, which claims benefit of U.S. Provisional Patent Application No. 61/011,324, filed Jan. 15, 2008, which applications are incorporated herein by reference in their entirety.

FEDERALLY SPONSORED RESEARCH AND DEVELOPMENT

This invention was made with Government support under contract CA086017 awarded by the National Institutes of Health. The Government has certain rights in the invention.

BACKGROUND OF THE INVENTION

Basic cancer research has focused on identifying the genetic changes that lead to cancer. This has led to major advances in our understanding of the molecular and biochemical pathways that are involved in tumorigenesis and malignant transformation. However, our understanding of the cellular biology has lagged. Although the effects of particular mutations on the proliferation and survival of model cells, such as fibroblasts or cell lines, can be predicted, the effects of such mutations on the actual cells involved in specific cancers is largely guesswork.

A tumor can be viewed as an aberrant organ initiated by a tumorigenic cancer cell that acquired the capacity for indefinite proliferation through accumulated mutations. In this view of a tumor as an abnormal organ, the principles of normal stem cell biology can be applied to better understand how tumors develop. Many observations suggest that analogies between normal stem cells and tumorigenic cells are appropriate. Both normal stem cells and tumorigenic cells have extensive proliferative potential and the ability to give rise to new (normal or abnormal) tissues. Both tumors and normal tissues are composed of heterogeneous combinations of cells, with different phenotypic characteristics and different proliferative potentials.

Because most tumors have a clonal origin, the original tumorigenic cancer cell gives rise to phenotypically diverse progeny, including cancer cells with indefinite proliferative potential, as well as cancer cells with limited or no proliferative potential. This suggests that tumorigenic cancer cells undergo processes that are analogous to the self-renewal and differentiation of normal stem cells. Tumorigenic cells can be thought of as cancer stem cells that undergo an aberrant and poorly regulated process of organogenesis analogous to what normal stem cells do. Although some of the heterogeneity in tumors arises as a result of continuing mutagenesis, it is likely that heterogeneity also arises through the aberrant differentiation of cancer cells.

It is well documented that many types of tumors contain cancer cells with heterogeneous phenotypes, reflecting aspects of the differentiation that normally occurs in the tissues from which the tumors arise. The variable expression of normal differentiation markers by cancer cells in a tumor suggests that some of the heterogeneity in tumors arises as a result of the anomalous differentiation of tumor cells. Examples of this include the variable expression of myeloid markers in chronic myeloid leukaemia, the variable expression of neuronal markers within peripheral neurectodermal tumors, and the variable expression of milk proteins or the estrogen receptor within breast cancer.

It was first extensively documented for leukemia and multiple myeloma that only a small subset of cancer cells is capable of extensive proliferation. Because the differences in clonogenicity among the leukemia cells mirrored the differences in clonogenicity among normal hematopoietic cells, the clonogenic leukemic cells were described as leukemic stem cells. It has also been shown for solid cancers that the cells are phenotypically heterogeneous and that only a small proportion of cells are clonogenic in culture and in vivo. Just as in the context of leukemic stem cells, these observations led to the hypothesis that only a few cancer cells are actually tumorigenic and that these tumorigenic cells act as cancer stem cells.

In support of this hypothesis, recent studies have shown that, similar to leukemia and other hematologic malignancies, tumorigenic and non-tumorigenic populations of breast cancer cells can be isolated based on their expression of cell surface markers. In many cases of breast cancer, only a small subpopulation of cells had the ability to form new tumors. This work strongly supports the existence of CSC in breast cancer. Further evidence for the existence of cancer stem cells occurring in solid tumors has been found in central nervous system (CNS) malignancies. Using culture techniques similar to those used to culture normal neuronal stem cells it has been shown that neuronal CNS malignancies contain a small population of cancer cells that are clonogenic in vitro and initiate tumors in vivo, while the remaining cells in the tumor do not have these properties.

Stem cells are defined as cells that have the ability to perpetuate themselves through self-renewal and to generate mature cells of a particular tissue through differentiation. In most tissues, stem cells are rare. As a result, stem cells must be identified prospectively and purified carefully in order to study their properties. Perhaps the most important and useful property of stem cells is that of self-renewal. Through this property, striking parallels can be found between stem cells and cancer cells: tumors may often originate from the transformation of normal stem cells, similar signaling pathways may regulate self-renewal in stem cells and cancer cells, and cancers may comprise rare cells with indefinite potential for self-renewal that drive tumorigenesis.

The presence of cancer stem cells has profound implications for cancer therapy. At present, all of the phenotypically diverse cancer cells in a tumor are treated as though they have unlimited proliferative potential and can acquire the ability to metastasize. For many years, however, it has been recognized that small numbers of disseminated cancer cells can be detected at sites distant from primary tumors in patients that never manifest metastatic disease. One possibility is that immune surveillance is highly effective at killing disseminated cancer cells before they can form a detectable tumor. Another possibility is that most cancer cells lack the ability to form a new tumor such, that only the dissemination of rare cancer stem cells can lead to metastatic disease. If so, the goal of therapy must be to identify and kill this cancer stem cell population.

The prospective identification and isolation of cancer stem cells will allow more efficient identification of diagnostic markers and therapeutic targets expressed by the stem cells. Existing therapies have been developed largely against the bulk population of tumor cells, because the therapies are identified by their ability to shrink the tumor mass. However, because most cells within a cancer have limited proliferative potential, an ability to shrink a tumor mainly reflects an ability to kill these cells. Therapies that are more specifically directed against cancer stem cells may result in more durable responses and cures of metastatic tumors.

Hematopoiesis proceeds through an organized developmental hierarchy initiated by hematopoietic stem cells (HSC) that give rise to progressively more committed progenitors and eventually terminally differentiated blood cells. Although the concept of the HSC was not new, it was not until 1988 that it was shown that this population could be prospectively isolated from mouse bone marrow on the basis of cell-surface markers using fluorescence-activated cell sorting (FACS). Since that time, the surface immunophenotype of the mouse HSC has become increasingly refined, such that functional HSC can be isolated with exquisite sensitivity, resulting in a purity of 1 in 1.3 cells. While our ability to prospectively isolate mouse HSC has improved dramatically over the past 20 years, our understanding of the earliest events in the human hematopoietic system lags far behind.

Cancer stem cells are discussed in, for example, Pardal et al. (2003) Nat Rev Cancer 3, 895-902; Reya et al. (2001) Nature 414, 105-11; Bonnet & Dick (1997) Nat Med 3, 730-7; Al-Hajj et al. (2003) Proc Natl Acad Sci USA 100, 3983-8; Dontu et al. (2004) Breast Cancer Res 6, R605-15; Singh et al. (2004) Nature 432, 396-401.

The identification of a hierarchy of multipotent hematopoietic progenitors in human cord blood, including multipotent progenitor cells, may be found in Majeti et al. (2007) Cell Stem Cell1(6):635-45, herein specifically incorporated by reference, particularly with respect to the teaching of markers identifying the multipotent progenitors.

SUMMARY OF THE INVENTION

Markers of acute myeloid leukemia stem cells (AMLSC) are provided herein. The markers are polynucleotides or polypeptides that are differentially expressed on AMLSC as compared to normal counterpart cells. Uses of the markers include use as targets for therapeutic antibodies or ligands; as targets for drug development, and for identification or selection of AMLSC cell populations.

The AMLSC markers are useful as targets of therapeutic monoclonal antibodies for treatment of patients with de novo, relapsed, or refractory acute myeloid leukemia. Such monoclonal antibodies are also useful in the treatment of pre-leukemic conditions, such as myelodysplastic syndromes (MDS) and myeloproliferative disorders (MPDs) including: chronic myelogenous leukemia, polycythemia vera, essential thrombocytosis, agnogenic myelofibrosis and myeloid metaplasia, and others. Antibodies include free antibodies and antigen binding fragments derived therefrom, and conjugates, e.g. pegylated antibodies, drug, radioisotope, or toxin conjugates, and the like.

In some embodiments, combinations of monoclonal antibodies are used in the treatment of human AML or pre-leukemic conditions. In one embodiment, a monoclonal antibody directed against CD47, for example an antibody that blocks the interaction of CD47 with SIRPα, combined with monoclonal antibodies directed against one or more additional AMLSC markers, e.g. CD96, CD97, CD99, CD180, PTHR2, HAVCR2 (also referred to as TIM3), and the like, which compositions can be synergistic in enhancing phagocytosis and elimination of AML LSC as compared to the use of single antibodies.

The AMLSC markers are useful as targets of monoclonal antibodies for use in ex vivo purging of autologous stem cell products (mobilized peripheral blood or bone marrow) for use in autologous transplantation for patients with acute myeloid leukemia or the pre-leukemic conditions outlined above. Combinations of monoclonal antibodies directed against AML LSC-specific cell surface molecules, as described above, can be synergistic in eliminating LSC.

The AMLSC markers are useful in clinical diagnostic applications including, without limitation, primary diagnosis of AML or pre-leukemic conditions from blood and/or bone marrow specimens, evaluation of leukemic involvement of the cerebrospinal and other body fluids, monitoring of interval disease progression, and monitoring of minimal residual disease status.

As an alternative to monoclonal antibodies, the ligands of AMLSC markers, either as single agents or in combination, may be used to target them in AML or the pre-leukemic conditions outlined above. The ligands can be free or conjugated, for direct administration to patients or for ex vivo purging of autologous stem cell products. Some specific molecules and their ligands include, without limitation, CD155-Fc fusion protein that binds CD96; TIP39 that binds PTHR2; Galectin-9 that binds HAVCR2.

The AMLSC cells can be prospectively isolated or identified from primary tumor samples, and possess the unique properties of cancer stem cells in functional assays for cancer stem cell self-renewal and differentiation.

In some embodiments of the invention, methods are provided for detection, classification or clinical staging of acute myeloid leukemias according to the stem cells that are present in the leukemia, where greater numbers of stem cells are indicative of a more aggressive cancer phenotype. Staging is useful for prognosis and treatment. In some embodiments, a tumor sample is analyzed by histochemistry, including immunohistochemistry, in situ hybridization, and the like, for the presence of $CD34^+CD38^-$ cells that express one or more AMLSC markers provided herein. The presence of such cells indicates the presence of AMLSC.

In another embodiment of the invention, methods for the isolation of AMLSC are provided, comprising contacted a candidate cell population with a binding reagent specific for one or more of the AMLSC markers provided herein, and selecting for cells that have bound to the reagent(s). The cells may further be selected as being $CD34^+CD38^-$. The cells are useful for experimental evaluation, and as a source of lineage and cell specific products, including mRNA species useful in identifying genes specifically expressed in these cells, and as targets for the discovery of factors or molecules that can affect them. AMLSC may be used, for example, in a method of screening a compound for an effect on the cells. This involves combining the compound with the cell population of the invention, and then determining any modulatory effect resulting from the compound. This may include examination of the cells for viability, toxicity, metabolic change, or an effect on cell function. The phenotype of AMLSC described herein provides a means of predicting disease progression, relapse, and development of drug resistance.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 1A-1B: Differential Gene Expression Between AML LSC and Normal Bone Marrow HSC and MPP (FIG. 1A) Heat maps demonstrating genes found to be differentially expressed at least 2 fold between bone marrow HSC (n=4) and AML LSC (n=9) or bone marrow MPP (n=4) and AML LSC (n=9). Expression relative to the median is indicated for genes with p<0.05 and a FDR of 5%. (FIG. 1B) Selected list of transmembrane proteins found to be at least 2-fold more highly expressed in AML LSC than HSC of MPP. NS: not significant.

(FIG. 2A) Representative flow cytometry plots indicating expression of CD47 relative to an isotype control. (FIG. 2B) Summary of CD47 expression on all samples assayed, with the indicated means.

FIG. 3A-3C: Anti-CD47 Antibody Stimulates In Vitro Macrophage Phagocytosis of Primary Human AML LSC. AML LSC were purified by FACS from two primary human AML samples, labeled with the fluorescent dye CFSE, and incubated with mouse bone marrow-derived macrophages either in the presence of an isotype control (FIG. 3A) or anti-CD47 antibody (FIG. 3B). These cells were assessed by immunofluorescence microscopy for the presence of fluorescently labeled LSC within the macrophages. (FIG. 3C) The phagocytic index was determined for each condition by calculating the number of ingested cells per 100 macrophages.

(FIG. 4A, 4B) two independent primary AML LSC samples.

FIG. 11A-11G: TIM-3 is More Highly Expressed on Functional AML LSC Than on Functional NBM HSC. (FIG. 11A) Representative flow cytometry histograms indicating TIM-3 expression on NBM HSC (Lin−CD34+CD38−CD90+) and AML LSC (Lin−CD34+CD38−CD90). (FIG. 11B) TIM-3 protein expression was assessed by flow cytometry for multiple specimens of NBM HSC, primary AML LSC, and bulk AML. Mean fluorescence intensity was normalized for cell size and against lineage-positive cells for comparison between measurements conducted on different days. (FIG. 11C) The percentage of cells positive for TIM-3 expression by flow cytometry within the Lin−CD34+CD38− compartment of AML and normal bone marrow samples was determined by comparison to isotype control. (FIG. 11D) TIM-3+ and TIM-3− fractions of the Lin−CD34+CD38− compartment from normal human bone marrow sample NBM05 were purified by two rounds of fluorescence-activated cell sorting (FACS). Top panels demonstrate expression of the indicated surface markers prior to sorting, while the bottom panels indicate results post-sorting. (FIG. 11E) These cells were transplanted into NSG pups and, twelve weeks later, bone marrow was analyzed by flow cytometry for the presence of human CD45+ leukocyte engraftment (left) whose lineage was further defined by expression of CD19 on lymphoid cells and CD33 on myeloid cells (right). (FIG. 11F) TIM-3+ and TIM-3− fractions of the Lin−CD34+ compartment from AML sample SU018 were double-sorted by FACS. (FIG. 11G) These cells were transplanted into NSG pups and 12 weeks later, human engraftment in mouse bone marrow was analyzed as above.

FIG. 12A-12F: Prospective Isolation of Residual Normal HSC From AML Patient Samples. (FIG. 12A) TIM-3 expression was determined on the Lin−CD34+CD38−fraction of AML sample SU031 by flow cytometry. TIM-3− and TIM-3+ cells were double-sorted to >99% purity by FACS. (FIG. 12B) These sorted cells were transplanted into NSG pups and, 12 weeks later, human engraftment in mouse bone marrow was analyzed. (FIG. 12C) RT-PCR for the CBFB-MYH11 fusion transcript produced by inv(16) and human β-actin. (FIG. 12D) TIM-3 expression was determined on the Lin−CD34+CD38− fraction of AML sample SU043 by flow cytometry. TIM-3− and TIM-3+ cells of were double-sorted to >98% purity by FACS. (FIG. 12E) These sorted cells were plated in duplicate into complete methylcellulose media and, fourteen days later, myeloid colony formation was determined by microscopy. (FIG. 12F) PCR of genomic DNA FLT3 amplicon size identified wild-type FLT3 and FLT3-ITD. Note that in the leukemic cells, no wild-type FLT3 is detected indicating homozygous FLT3-ITD.

FIG. 13A-13D: Prospective Separation of Functional HSC and Functional AML LSC From a Single Patient Sample. (FIG. 13A) TIM-3 expression was determined on the Lin−CD34+CD38− fraction of AML sample SU030 by flow cytometry. TIM-3+ and TIM-3− cells were double-sorted to >99% purity by FACS. (FIG. 13B) These sorted cells were plated in duplicate into complete methylcellulose media, and fourteen days later, myeloid colony formation was determined by microscopy. A representative BFU-E is shown. (FIG. 13C) Lin−CD34+CD38−TIM-3+ and Lin−CD34+CD38−TIM-3−sorted cells were transplanted into NSG pups and, 12 weeks later, human engraftment in mouse bone marrow was analyzed. (FIG. 13D) PCR of genomic DNA for FLT3 amplicon size identified wild-type FLT3 and FLT3-ITD.

DETAILED DESCRIPTION OF THE EMBODIMENTS

Figures 2A, 2B:
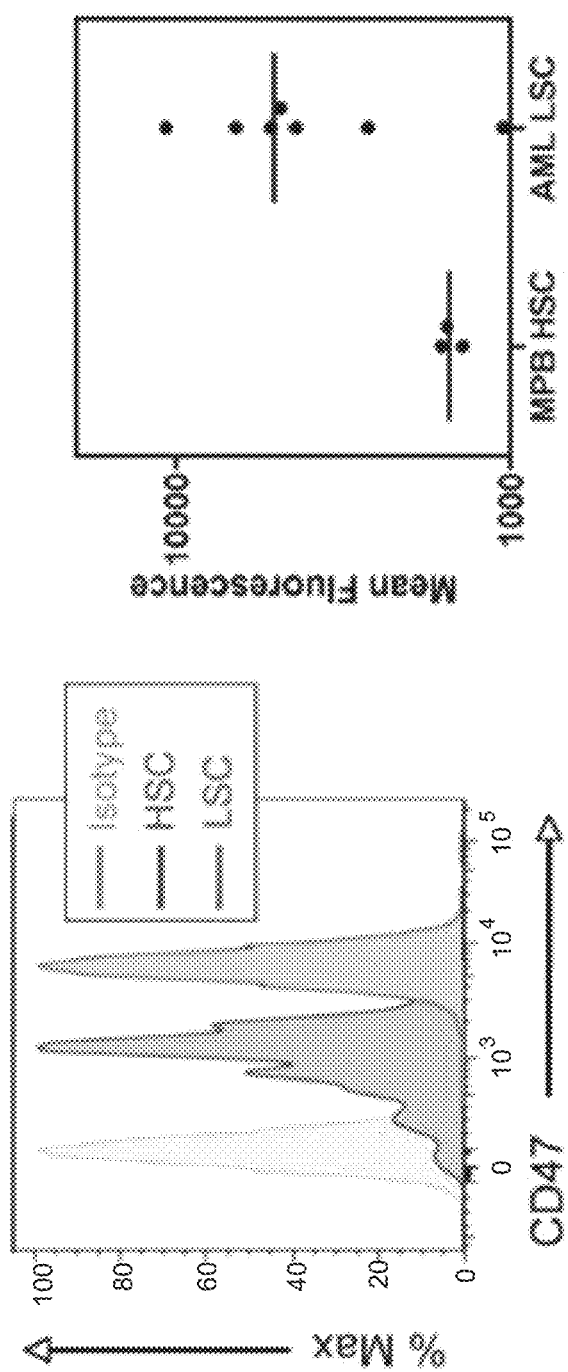
FIG. 2A-2B: CD47 is more highly expressed on AML LSC. Mobilized peripheral blood (MPB) HSC and AML LSC were examined for CD47 expression by flow cytometry.
Figures 4A, 4B:
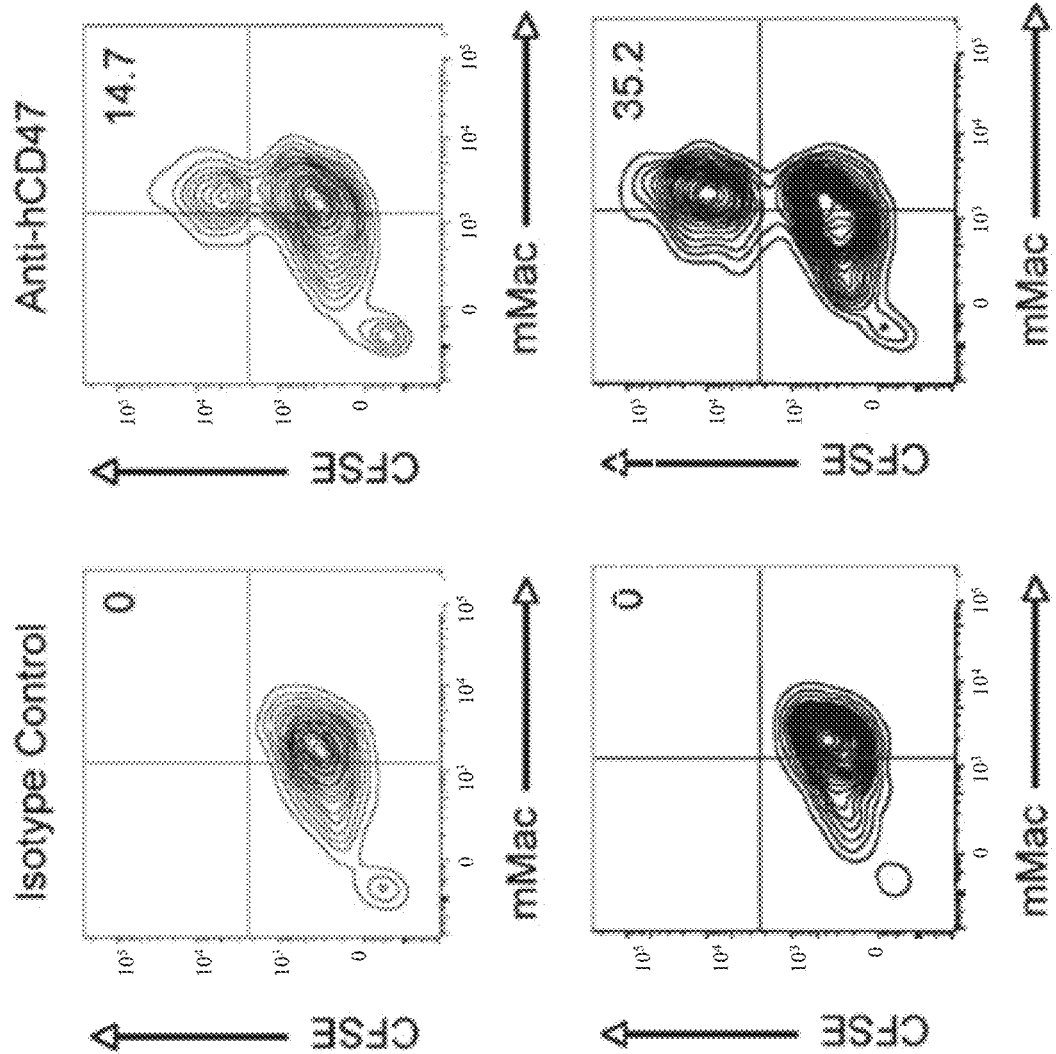
FIG. 4A-4B: Anti-CD47 antibody stimulates in vitro macrophage phagocytosis of primary human AML LSC. AML LSC were purified by FACS from two primary human AML samples and labeled with the fluorescent dye CFSE. These cells were incubated with mouse bone marrow-derived macrophages, either in the presence of an isotype matched control (left) or anti-CD47 antibody (right). The macrophages were harvested, stained with a fluorescently labeled anti-mouse macrophage antibody, and analyzed by flow cytometry. mMac+CFSE+ double-positive events identify macrophages that have phagocytosed CFSE-labeled LSC.

The present invention identifies polynucleotides, as well as polypeptides encoded thereby, that are differentially expressed in acute myeloid leukemia stem cells (AMLSC). Methods are provided in which these polynucleotides and polypeptides, which may be collectively referred to as AMLSC markers, are used for detecting, assessing, and reducing the growth of cancer cells. Methods may use one or a combination of markers, where a combination may include 2, 3 or more markers, and in some embodiments will include CD47 in combination with 1, 2 or more markers. Other embodiments include TIM3 in combination with 1, 2 or more markers, including a combination of TIM3 and CD47, for example where antibodies that specifically bind to each of TIM3 and CD47 are used in the identification, characterization and/or elimination of AMLSC. The invention finds use in the prevention, treatment, detection or research of leukemic and pre-leukemic conditions.

The markers of the invention in some embodiments are expressed on the AMLSC cell surface. In some embodiments, the markers are expressed as a level at least 2× the expression level of a counterpart non-transformed cell, e.g. a human hematopoietic stem cell, and/or a human hematopoietic multipotent progenitor cell, where expression may be determined as the level of transcription, mRNA accumulation, and/or protein accumulation. In other embodiments the markers are expressed as a level at least 3×, at least 4×, at least 5×, at least 10×, at least 20× or greater, than the expression level of a counterpart non-transformed cell.

The present invention provides methods of using the markers described herein in diagnosis of cancer, classification and treatment of leukemic and pre-leukemic conditions according to expression profiles. The methods are useful for detecting AMLSC, facilitating diagnosis of AML and the severity of the cancer (e.g., tumor grade, tumor burden, and the like) in a subject, facilitating a determination of the prognosis of a subject, and assessing the responsiveness of the subject to therapy. The detection methods of the invention can be conducted in vitro or in vivo, on isolated cells, or in whole tissues or a bodily fluid, e.g., blood, lymph node biopsy samples, and the like.

As used herein, the terms "a gene that is differentially expressed in a cancer stem cell," and "a polynucleotide that is differentially expressed in a cancer stem cell", are used interchangeably herein, and generally refer to a polynucleotide that represents or corresponds to a gene that is differentially expressed in a cancer stem cell when compared with a cell of the same cell type that is not cancerous, e.g., mRNA is found at levels at least about 25%, at least about 50% to about 75%, at least about 90%, at least about 1.5-fold, at least about 2-fold, at least about 3-fold, at least about 5-fold, at least about 10-fold, or at least about 50-fold or more, different (e.g., higher or lower). The comparison can be made between AMLSC and the normal counterpart cells a human hematopoietic stem cell (HSC), which include without limitation cells having the phenotype Lin$^-$CD34$^+$CD38$^-$CD90$^+$; or the phenotype Lin$^-$CD34$^+$CD38$^-$CD90$^+$CD45RA$^-$ and a human hematopoietic multipotent progenitor cell (MPP), which include without limitation cells having the phenotype Lin$^-$CD34$^+$CD38$^-$CD90$^-$; or the phenotype Lin$^-$CD34$^+$CD38$^-$CD90$^-$CD45RA$^-$. The term "a polypeptide marker for a cancer stem cell" refers to a polypeptide encoded by a polynucleotide that is differentially expressed in a cancer stem cell.

In some embodiments of the invention, the markers are demonstrated by flow cytometry to be present on a majority of AMLSC, when compared to human HSC or MPP, as defined above. Such markers include, without limitation, CD47, CD96, CD97, TIM3 and CD99.

In other embodiments of the invention, the markers are absent on human HSC or human MPP, but are highly expressed on AMLSC. Such markers include, without limitation, those set forth in Table 1.

In other embodiments, the markers are differentially expressed on AMLSC, as compared to human HSC or MPP. Such markers include, without limitation, those set forth in Table 1.

A polynucleotide or sequence that corresponds to, or represents a gene means that at least a portion of a sequence of the polynucleotide is present in the gene or in the nucleic acid gene product (e.g., mRNA or cDNA). A subject nucleic acid may also be "identified" by a polynucleotide if the polynucleotide corresponds to or represents the gene. Genes identified by a polynucleotide may have all or a portion of the identifying sequence wholly present within an exon of a genomic sequence of the gene, or different portions of the sequence of the polynucleotide may be present in different exons (e.g., such that the contiguous polynucleotide sequence is present in an mRNA, either pre- or post-splicing, that is an expression product of the gene). An "identifying sequence" is a minimal fragment of a sequence of contiguous nucleotides that uniquely identifies or defines a polynucleotide sequence or its complement.

The polynucleotide may represent or correspond to a gene that is modified in a cancer stem cell (CSC) relative to a normal cell. The gene in the CSC may contain a deletion, insertion, substitution, or translocation relative to the polynucleotide and may have altered regulatory sequences, or may encode a splice variant gene product, for example. The gene in the CSC may be modified by insertion of an endogenous retrovirus, a transposable element, or other naturally occurring or non-naturally occurring nucleic acid.

Sequences of interest include those set forth in Table 1, which are differentially expressed in AMLSC relative to normal counterpart cells.

Methods are also provided for optimizing therapy, by first classification, and based on that information, selecting the appropriate therapy, dose, treatment modality, etc. which optimizes the differential between delivery of an anti-proliferative treatment to the undesirable target cells, while minimizing undesirable toxicity. The treatment is optimized by selection for a treatment that minimizes undesirable toxicity, while providing for effective anti-proliferative activity.

The invention finds use in the prevention, treatment, detection or research of acute myeloid leukemias. Acute leukemias are rapidly progressing leukemia characterized by replacement of normal bone marrow by blast cells of a clone arising from malignant transformation of a hematopoietic stem cell. The acute leukemias include acute lymphoblastic leukemia (ALL) and acute myelogenous leukemia (AML). ALL often involves the CNS, whereas acute monoblastic leukemia involves the gums, and AML involves localized collections in any site (granulocytic sarcomas or chloromas). AML is the most common acute leukemia affecting adults, and its incidence increases with age. While AML is a relatively rare disease overall, accounting for approximately 1.2% of cancer deaths in the United States, its incidence is expected to increase as the population ages.

The presenting symptoms are usually nonspecific (e.g., fatigue, fever, malaise, weight loss) and reflect the failure of normal hematopoiesis. Anemia and thrombocytopenia are very common (75 to 90%). The WBC count may be decreased, normal, or increased. Blast cells are usually found in the blood smear unless the WBC count is markedly decreased. The blasts of ALL can be distinguished from those of AML by histochemical studies, cytogenetics, immunophenotyping, and molecular biology studies. In addition to smears with the usual stains, terminal transferase, myeloperoxidase, Sudan black B, and specific and nonspecific esterase.

"Diagnosis" as used herein generally includes determination of a subject's susceptibility to a disease or disorder, determination as to whether a subject is presently affected by a disease or disorder, prognosis of a subject affected by a disease or disorder (e.g., identification of cancerous states, stages of cancer, or responsiveness of cancer to therapy), and use of therametrics (e.g., monitoring a subject's condition to provide information as to the effect or efficacy of therapy).

The term "biological sample" encompasses a variety of sample types obtained from an organism and can be used in a diagnostic or monitoring assay. The term encompasses blood and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components. The term encompasses a clinical sample, and also includes cells in cell culture, cell supernatants, cell lysates, serum, plasma, biological fluids, and tissue samples.

The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

The terms "individual," "subject," "host," and "patient," used interchangeably herein and refer to any mammalian subject for whom diagnosis, treatment, or therapy is desired, particularly humans.

A "host cell", as used herein, refers to a microorganism or a eukaryotic cell or cell line cultured as a unicellular entity which can be, or has been, used as a recipient for a recombinant vector or other transfer polynucleotides, and include the progeny of the original cell which has been transfected. It is understood that the progeny of a single cell may not necessarily be completely identical in morphology or in genomic or total DNA complement as the original parent, due to natural, accidental, or deliberate mutation.

The terms "cancer", "neoplasm", "tumor", and "carcinoma", are used interchangeably herein to refer to cells which exhibit relatively autonomous growth, so that they exhibit an aberrant growth phenotype characterized by a significant loss of control of cell proliferation. In general, cells of interest for detection or treatment in the present application include precancerous (e.g., benign), malignant, pre-metastatic, metastatic, and non-metastatic cells. Detection of cancerous cells is of particular interest. The term "normal" as used in the context of "normal cell," is meant to refer to a cell of an untransformed phenotype or exhibiting a morphology of a non-transformed cell of the tissue type being examined. "Cancerous phenotype" generally refers to any of a variety of biological phenomena that are characteristic of a cancerous cell, which phenomena can vary with the type of cancer. The cancerous phenotype is generally identified by abnormalities in, for example, cell growth or proliferation (e.g., uncontrolled growth or proliferation), regulation of the cell cycle, cell mobility, cell-cell interaction, or metastasis, etc.

"Therapeutic target" refers to a gene or gene product that, upon modulation of its activity (e.g., by modulation of expression, biological activity, and the like), can provide for modulation of the cancerous phenotype. As used throughout, "modulation" is meant to refer to an increase or a decrease in the indicated phenomenon (e.g., modulation of a biological activity refers to an increase in a biological activity or a decrease in a biological activity).

Acute Myeloid Leukemia

Acute Myelocytic Leukemia (AML, Acute Myelogenous Leukemia; Acute Myeloid

Leukemia). In AML, malignant transformation and uncontrolled proliferation of an abnormally differentiated, long-lived myeloid progenitor cell results in high circulating numbers of immature blood forms and replacement of normal marrow by malignant cells. Symptoms include fatigue, pallor, easy bruising and bleeding, fever, and infection; symptoms of leukemic infiltration are present in only about 5% of patients (often as skin manifestations). Examination of peripheral blood smear and bone marrow is diagnostic. Treatment includes induction chemotherapy to achieve remission and post-remission chemotherapy (with or without stem cell transplantation) to avoid relapse.

AML has a number of subtypes that are distinguished from each other by morphology, immunophenotype, and cytochemistry. Five classes are described, based on predominant cell type, including myeloid, myeloid-monocytic, monocytic, erythroid, and megakaryocytic. Acute promyelocytic leukemia is a particularly important subtype, representing 10 to 15% of all cases of AML, striking a younger age group (median age 31 yr) and particular ethnicity (Hispanics), in which the patient commonly presents with a coagulation disorder.

Remission induction rates range from 50 to 85%. Long-term disease-free survival reportedly occurs in 20 to 40% of patients and increases to 40 to 50% in younger patients treated with stem cell transplantation.

Prognostic factors help determine treatment protocol and intensity; patients with strongly negative prognostic features are usually given more intense forms of therapy, because the potential benefits are thought to justify the increased treatment toxicity. The most important prognostic factor is the leukemia cell karyotype; favorable karyotypes include t(15; 17), t(8;21), and inv16 (p13;q22). Negative factors include increasing age, a preceding myelodysplastic phase, secondary leukemia, high WBC count, and absence of Auer rods. The FAB or WHO classification alone does not predict response.

Initial therapy attempts to induce remission and differs most from ALL in that AML responds to fewer drugs. The basic induction regimen includes cytarabine by continuous IV infusion or high doses for 5 to 7 days; daunorubicin or idarubicin is given IV for 3 days during this time. Some regimens include 6-thioguanine, etoposide, vincristine, and prednisone, but their contribution is unclear. Treatment usually results in significant myelosuppression, with infection or bleeding; there is significant latency before marrow recovery. During this time, meticulous preventive and supportive care is vital.

Polypeptide and Polynucleotide Sequences and Antibodies

The invention provides polynucleotides and polypeptides that represent genes that are differentially expressed in human AMLSC. These polynucleotides, polypeptides and fragments thereof have uses that include, but are not limited to, diagnostic probes and primers as starting materials for probes and primers, as immunogens for antibodies useful in cancer diagnosis and therapy, and the like as discussed herein.

Nucleic acid compositions include fragments and primers, and are at least about 15 bp in length, at least about 30 bp in length, at least about 50 bp in length, at least about 100 bp, at least about 200 bp in length, at least about 300 bp in length, at least about 500 bp in length, at least about 800 bp in length, at least about 1 kb in length, at least about 2.0 kb in length, at least about 3.0 kb in length, at least about 5 kb in length, at least about 10 kb in length, at least about 50 kb in length and are usually less than about 200 kb in length. In some embodiments, a fragment of a polynucleotide is the coding sequence of a polynucleotide. Also included are variants or degenerate variants of a sequence provided herein. In general, variants of a polynucleotide provided herein have a fragment of sequence identity that is greater than at least about 65%, greater than at least about 70%, greater than at least about 75%, greater than at least about 80%, greater than at least about 85%, or greater than at least about 90%, 95%, 96%, 97%, 98%, 99% or more (i.e. 100%) as compared to an identically sized fragment of a provided sequence. as determined by the Smith-Waterman homology search algorithm as implemented in MPSRCH program (Oxford Molecular). Nucleic acids having sequence similarity can be detected by hybridization under low stringency conditions, for example, at 50° C. and 10×SSC (0.9 M saline/0.09 M sodium citrate) and remain bound when subjected to washing at 55° C. in 1×SSC. Sequence identity can be determined by hybridization under high stringency conditions, for example, at 50° C. or higher and 0.1×SSC (9 mM saline/0.9 mM sodium citrate). Hybridization methods and conditions are well known in the art, see, e.g., U.S. Pat. No. 5,707,829. Nucleic acids that are substantially identical to the provided polynucleotide sequences, e.g. allelic variants, genetically altered versions of the gene, etc., bind to the provided polynucleotide sequences under stringent hybridization conditions.

Probes specific to the polynucleotides described herein can be generated using the polynucleotide sequences disclosed herein. The probes are usually a fragment of a polynucleotide sequences provided herein. The probes can be synthesized chemically or can be generated from longer polynucleotides using restriction enzymes. The probes can be labeled, for example, with a radioactive, biotinylated, or fluorescent tag. Preferably, probes are designed based upon an identifying sequence of any one of the polynucleotide sequences provided herein.

The nucleic acid compositions described herein can be used to, for example, produce polypeptides, as probes for the detection of mRNA in biological samples (e.g., extracts of human cells) or cDNA produced from such samples, to generate additional copies of the polynucleotides, to generate ribozymes or antisense oligonucleotides, and as single stranded DNA probes or as triple-strand forming oligonucleotides.

The probes described herein can be used to, for example, determine the presence or absence of any one of the polynucleotide provided herein or variants thereof in a sample. These and other uses are described in more detail below. In one embodiment, real time PCR analysis is used to analyze gene expression.

The polypeptides contemplated by the invention include those encoded by the disclosed polynucleotides and the genes to which these polynucleotides correspond, as well as nucleic acids that, by virtue of the degeneracy of the genetic code, are not identical in sequence to the disclosed polynucleotides. Further polypeptides contemplated by the invention include polypeptides that are encoded by polynucleotides that hybridize to polynucleotide of the sequence listing. Thus, the invention includes within its scope a polypeptide encoded by a polynucleotide having the sequence of any one of the polynucleotide sequences provided herein, or a variant thereof.

In general, the term "polypeptide" as used herein refers to both the full length polypeptide encoded by the recited polynucleotide, the polypeptide encoded by the gene represented by the recited polynucleotide, as well as portions or fragments thereof. "Polypeptides" also includes variants of the naturally occurring proteins, where such variants are homologous or substantially similar to the naturally occurring protein, and can be of an origin of the same or different species as the naturally occurring protein. In general, variant polypeptides have a sequence that has at least about 80%, usually at least about 90%, and more usually at least about 98% sequence identity with a differentially expressed polypeptide described herein. The variant polypeptides can be naturally or non-naturally glycosylated, i.e., the polypeptide has a glycosylation pattern that differs from the glycosylation pattern found in the corresponding naturally occurring protein.

Fragments of the polypeptides disclosed herein, particularly biologically active fragments and/or fragments corresponding to functional domains, are of interest. Fragments of interest will typically be at least about 10 aa to at least about 15 aa in length, usually at least about 50 aa in length, and can be as long as 300 aa in length or longer, but will usually not exceed about 1000 aa in length, where the fragment will have a stretch of amino acids that is identical to a polypeptide encoded by a polynucleotide having a sequence of any one of the polynucleotide sequences provided herein, or a homolog thereof. A fragment "at least 20 aa in length," for example, is intended to include 20 or more contiguous amino acids from, for example, the polypeptide encoded by a cDNA, in a cDNA clone contained in a deposited library or the complementary stand thereof. In this context "about" includes the particularly recited value or a value larger or smaller by several (5, 4, 3, 2, or 1) amino acids. The protein variants described herein are encoded by polynucleotides that are within the scope of the invention. The genetic code can be used to select the appropriate codons to construct the corresponding variants. The polynucleotides may be used to produce polypeptides, and these polypeptides may be used to produce antibodies by known methods described above and below.

A polypeptide of this invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast higher plant, insect, and mammalian cells.

Gene products, including polypeptides, mRNA (particularly mRNAs having distinct secondary and/or tertiary structures), cDNA, or complete gene, can be prepared and used for raising antibodies for experimental, diagnostic, and therapeutic purposes. Antibodies may be used to identify AMLSC cells or subtypes. The polynucleotide or related cDNA is expressed as described herein, and antibodies are prepared. These antibodies are specific to an epitope on the polypeptide encoded by the polynucleotide, and can precipitate or bind to the corresponding native protein in a cell or tissue preparation or in a cell-free extract of an in vitro expression system.

The antibodies may be utilized for immunophenotyping of cells and biological samples.

The translation product of a differentially expressed gene may be useful as a marker. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al. Cell, 96:737-49 (1999)). These techniques allow for the screening of particular populations of cells; in immunohistochemistry of biopsy samples; in detecting the presence of markers shed by cancer cells into the blood and other biologic fluids, and the like.

In many embodiments, the levels of a subject gene or gene product are measured. By measured is meant qualitatively or quantitatively estimating the level of the gene product in a first biological sample either directly (e.g. by determining or estimating absolute levels of gene product) or relatively by comparing the levels to a second control biological sample. In many embodiments the second control biological sample is obtained from an individual not having cancer. As will be appreciated in the art, once a standard control level of gene expression is known, it can be used repeatedly as a standard for comparison. Other control samples include samples of cancerous tissue.

The methods can be used to detect and/or measure mRNA levels of a gene that is differentially expressed in a cancer cell. In some embodiments, the methods comprise: contacting a sample with a polynucleotide that corresponds to a differentially expressed gene described herein under conditions that allow hybridization; and detecting hybridization, if any. Detection of differential hybridization, when compared to a suitable control, is an indication of the presence in the sample of a polynucleotide that is differentially expressed in a cancer cell. Appropriate controls include, for example, a sample that is known not to contain a polynucleotide that is differentially expressed in a cancer cell. Conditions that allow hybridization are known in the art, and have been described in more detail above.

Detection can also be accomplished by any known method, including, but not limited to, in situ hybridization, PCR (polymerase chain reaction), RT-PCR (reverse transcription-PCR), and "Northern" or RNA blotting, arrays, microarrays, etc, or combinations of such techniques, using a suitably labeled polynucleotide. A variety of labels and labeling methods for polynucleotides are known in the art and can be used in the assay methods of the invention. Specific hybridization can be determined by comparison to appropriate controls.

Labeled nucleic acid probes may be used to detect expression of a gene corresponding to the provided polynucleotide, e.g. in a macroarray format, Northern blot, etc. The amount of hybridization can be quantitated to determine relative amounts of expression, for example under a particular condition. Probes are used for in situ hybridization to cells to detect expression. Probes can also be used in vivo for diagnostic detection of hybridizing sequences. Probes may be labeled with a radioactive isotope. Other types of detectable labels can be used such as chromophores, fluorophores, and enzymes.

Polynucleotide arrays provide a high throughput technique that can assay a large number of polynucleotides or polypeptides in a sample. This technology can be used as a tool to test for differential expression. A variety of methods of producing arrays, as well as variations of these methods, are known in the art and contemplated for use in the invention. For example, arrays can be created by spotting polynucleotide probes onto a substrate (e.g., glass, nitrocellulose, etc.) in a two-dimensional matrix or array having bound probes. The probes can be bound to the substrate by either covalent bonds or by non-specific interactions, such as hydrophobic interactions.

Characterization of Acute Myeloid Leukemia Stem Cells

In acute myeloid leukemias, characterization of cancer stem cells allows for the development of new treatments that are specifically targeted against this critical population of cells, particularly their ability to self-renew, resulting in more effective therapies.

In human acute myeloid leukemias it is shown herein that there is a subpopulation of tumorigenic cancer cells with both self-renewal and differentiation capacity. These tumorigenic cells are responsible for tumor maintenance, and also give rise to large numbers of abnormally differentiating progeny that are not tumorigenic, thus meeting the criteria of cancer stem cells. Tumorigenic potential is contained within a subpopulation of cancer cells differentially expressing the markers of the present invention.

In some embodiments of the invention, the number of AMLSC in a patient sample is determined relative to the total number of AML cancer cells, where a greater percentage of AMLSC is indicative of the potential for continued self-renewal of cells with the cancer phenotype. The quantitation of AMLSC in a patient sample may be compared to a reference population, e.g. a patient sample such as a blood sample, a remission patient sample, etc. In some embodiments, the quantitation of AMLSC is performed during the course of treatment, where the number of AML cancer cells and the percentage of such cells that are AMLSC are quantitated before, during and as follow-up to a course of therapy. Desirably, therapy targeted to cancer stem cells results in a decrease in the total number, and/or percentage of AMLSC in a patient sample.

In other embodiments of the invention, anti-cancer agents are targeted to AMLSC by specific binding to a marker or combination of markers of the present invention. In such embodiments, the anti-cancer agents include antibodies and antigen-binding derivatives thereof specific for a marker or combination of markers of the present invention, which are optionally conjugated to a cytotoxic moiety. Depletion of AMLSC is useful in the treatment of AML. Depletion achieves a reduction in circulating AMLSC by up to about 30%, or up to about 40%, or up to about 50%, or up to about 75% or more. Depletion can be achieved by using a an agent to deplete AMLSC either in vivo or ex vivo.

The AMLSC are identified by their phenotype with respect to particular markers, and/or by their functional phenotype. In some embodiments, the AMLSC are identified and/or isolated by binding to the cell with reagents specific for the markers of interest. The cells to be analyzed may be viable cells, or may be fixed or embedded cells.

In some embodiments, the reagents specific for the markers of interest are antibodies, which may be directly or indirectly labeled. Such antibodies will usually include antibodies specific for a marker or combination of markers of the present invention.

Treatment of Cancer

The invention further provides methods for reducing growth of cancer cells. The methods provide for decreasing the number of cancer cells bearing a specific marker or combination of markers, as provided herein, decreasing expression of a gene that is differentially expressed in a cancer cell, or decreasing the level of and/or decreasing an activity of a cancer-associated polypeptide. In general, the methods comprise contacting a cancer cell with a binding agent, e.g. an antibody or ligand specific for a marker or combination of markers provided herein.

"Reducing growth of cancer cells" includes, but is not limited to, reducing proliferation of cancer cells, and reducing the incidence of a non-cancerous cell becoming a cancerous cell. Whether a reduction in cancer cell growth has been achieved can be readily determined using any known assay, including, but not limited to, [$^3$H]-thymidine incorporation; counting cell number over a period of time; detecting and/or measuring a marker associated with AML, etc.

The present invention provides methods for treating cancer, generally comprising administering to an individual in need thereof a substance that reduces cancer cell growth, in an amount sufficient to reduce cancer cell growth and treat the cancer. Whether a substance, or a specific amount of the substance, is effective in treating cancer can be assessed using any of a variety of known diagnostic assays for cancer, including, but not limited to biopsy, contrast radiographic studies, CAT scan, and detection of a tumor marker associated with cancer in the blood of the individual. The substance can be administered systemically or locally, usually systemically.

A substance, e.g. a chemotherapeutic drug that reduces cancer cell growth, can be targeted to a cancer cell. Thus, in some embodiments, the invention provides a method of delivering a drug to a cancer cell, comprising administering a drug-antibody complex to a subject, wherein the antibody is specific for a cancer-associated polypeptide, and the drug is one that reduces cancer cell growth, a variety of which are known in the art. Targeting can be accomplished by coupling (e.g., linking, directly or via a linker molecule, either covalently or non-covalently, so as to form a drug-antibody complex) a drug to an antibody specific for a cancer-associated polypeptide. Methods of coupling a drug to an antibody are well known in the art and need not be elaborated upon herein.

Staging and Diagnosis

Acute myeloid leukemias are staged by analysis of the presence of cancer stem cells. Staging is useful for prognosis and treatment. In one embodiment of the invention, a sample from an acute myeloid leukemia patient is stained with reagents specific for a marker or combination of markers of the present invention. The analysis of staining patterns provides the relative distribution of AMLSC, which distribution predicts the stage of leukemia. In some embodiments, the sample is analyzed by histochemistry, including immunohistochemistry, in situ hybridization, and the like, for the presence of $CD34^+CD38^-$ cells that express a marker or combination of markers of the present invention. The presence of such cells indicates the presence of AMLSC.

In one embodiment, the patient sample is compared to a control, or a standard test value. In another embodiment, the patient sample is compared to a pre-leukemia sample, or to one or more time points through the course of the disease.

Samples, including tissue sections, slides, etc. containing an acute myeloid leukemia tissue, are stained with reagents specific for markers that indicate the presence of cancer stem cells. Samples may be frozen, embedded, present in a tissue microarray, and the like. The reagents, e.g. antibodies, polynucleotide probes, etc. may be detectably labeled, or may be indirectly labeled in the staining procedure. The data provided herein demonstrate that the number and distribution of progenitor cells is diagnostic of the stage of the leukemia.

The information thus derived is useful in prognosis and diagnosis, including susceptibility to acceleration of disease, status of a diseased state and response to changes in the environment, such as the passage of time, treatment with drugs or other modalities. The cells can also be classified as to their ability to respond to therapeutic agents and treatments, isolated for research purposes, screened for gene expression, and the like. The clinical samples can be further characterized by genetic analysis, proteomics, cell surface staining, or other means, in order to determine the presence of markers that are useful in classification. For example, genetic abnormalities can be causative of disease susceptibility or drug responsiveness, or can be linked to such phenotypes.

Differential Cell Analysis

The presence of AMLSC in a patient sample can be indicative of the stage of the leukemia. In addition, detection of AMLSC can be used to monitor response to therapy and to aid in prognosis. The presence of AMLSC can be determined by quantitating the cells having the phenotype of the stem cell. In addition to cell surface phenotyping, it may be useful to quantitate the cells in a sample that have a "stem cell" character, which may be determined by functional criteria, such as the ability to self-renew, to give rise to tumors in vivo, e.g. in a xenograft model, and the like.

Clinical samples for use in the methods of the invention may be obtained from a variety of sources, particularly blood, although in some instances samples such as bone marrow, lymph, cerebrospinal fluid, synovial fluid, and the like may be used. Such samples can be separated by centrifugation, elutriation, density gradient separation, apheresis, affinity selection, panning, FACS, centrifugation with Hypaque, etc. prior to analysis, and usually a mononuclear fraction (PBMC) will be used. Once a sample is obtained, it can be used directly, frozen, or maintained in appropriate culture medium for short periods of time. Various media can be employed to maintain cells. The samples may be obtained by any convenient procedure, such as the drawing of blood, venipuncture, biopsy, or the like. Usually a sample will comprise at least about $10^2$ cells, more usually at least about $10^3$ cells, and preferable $10^4$, $10^5$ or more cells. Typically the samples will be from human patients, although animal models may find use, e.g. equine, bovine, porcine, canine, feline, rodent, e.g. mice, rats, hamster, primate, etc.

An appropriate solution may be used for dispersion or suspension of the cell sample. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

Analysis of the cell staining will use conventional methods. Techniques providing accurate enumeration include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g. propidium iodide).

The affinity reagents may be specific receptors or ligands for the cell surface molecules indicated above. In addition to antibody reagents, peptide-MHC antigen and T cell receptor pairs may be used; peptide ligands and receptors; effector and receptor molecules, and the like. Antibodies and T cell receptors may be monoclonal or polyclonal, and may be produced by transgenic animals, immunized animals, immortalized human or animal B-cells, cells transfected with DNA vectors encoding the antibody or T cell receptor, etc. The details of the preparation of antibodies and their suitability for use as specific binding members are well-known to those skilled in the art.

Of particular interest is the use of antibodies as affinity reagents. Conveniently, these antibodies are conjugated with a label for use in separation. Labels include magnetic beads, which allow for direct separation, biotin, which can be removed with avidin or streptavidin bound to a support, fluorochromes, which can be used with a fluorescence activated cell sorter, or the like, to allow for ease of separation of the particular cell type. Fluorochromes that find use include phycobiliproteins, e.g. phycoerythrin and allophycocyanins, fluorescein and Texas red. Frequently each antibody is labeled with a different fluorochrome, to permit independent sorting for each marker.

The antibodies are added to a suspension of cells, and incubated for a period of time sufficient to bind the available cell surface antigens. The incubation will usually be at least about 5 minutes and usually less than about 30 minutes. It is desirable to have a sufficient concentration of antibodies in the reaction mixture, such that the efficiency of the separation is not limited by lack of antibody. The appropriate concentration is determined by titration. The medium in which the cells are separated will be any medium that maintains the viability of the cells. A preferred medium is phosphate buffered saline containing from 0.1 to 0.5% BSA. Various media are commercially available and may be used according to the nature of the cells, including Dulbecco's Modified Eagle Medium (dMEM), Hank's Basic Salt Solution (HBSS), Dulbecco's phosphate buffered saline (dPBS), RPMI, Iscove's medium, PBS with 5 mM EDTA, etc., frequently supplemented with fetal calf serum, BSA, HSA, etc.

The labeled cells are then quantitated as to the expression of cell surface markers as previously described.

The comparison of a differential progenitor analysis obtained from a patient sample, and a reference differential progenitor analysis is accomplished by the use of suitable deduction protocols, AI systems, statistical comparisons, etc. A comparison with a reference differential progenitor analysis from normal cells, cells from similarly diseased tissue, and the like, can provide an indication of the disease staging. A database of reference differential progenitor analyses can be compiled. An analysis of particular interest tracks a patient, e.g. in the chronic and pre-leukemic stages of disease, such that acceleration of disease is observed at an early stage. The methods of the invention provide detection of acceleration prior to onset of clinical symptoms, and therefore allow early therapeutic intervention, e.g. initiation of chemotherapy, increase of chemotherapy dose, changing selection of chemotherapeutic drug, and the like.

AMLSC Compositions

AMLSC may be separated from a complex mixture of cells by techniques that enrich for cells that differentially express a marker or combination of markers of the present invention. For isolation of cells from tissue, an appropriate solution may be used for dispersion or suspension. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

The separated cells may be collected in any appropriate medium that maintains the viability of the cells, usually having a cushion of serum at the bottom of the collection tube. Various media are commercially available and may be used according to the nature of the cells, including dMEM, HBSS, dPBS, RPMI, Iscove's medium, etc., frequently supplemented with fetal calf serum.

Compositions highly enriched for AMLSC are achieved in this manner. The subject population may be at or about 50% or more of the cell composition, and preferably be at or about 75% or more of the cell composition, and may be 90% or more. The desired cells are identified by their surface phenotype, by the ability to self-renew, ability to form tumors, etc. The enriched cell population may be used immediately, or may be frozen at liquid nitrogen temperatures and stored for long periods of time, being thawed and capable of being reused. The cells may be stored in 10% DMSO, 90% FCS medium. The population of cells enriched for AMLSC may be used in a variety of screening assays and cultures, as described below.

The enriched AMLSC population may be grown in vitro under various culture conditions. Culture medium may be liquid or semi-solid, e.g. containing agar, methylcellulose, etc. The cell population may be conveniently suspended in an appropriate nutrient medium, such as Iscove's modified DMEM or RPMI-1640, normally supplemented with fetal calf serum (about 5-10%), L-glutamine, a thiol, particularly 2-mercaptoethanol, and antibiotics, e.g. penicillin and streptomycin.

The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors. A wide variety of growth factors may be used in culturing the cells, e.g. LIF, steel factor (c-kit ligand), EGF, insulin, IGF, Flk-2 ligand, IL-11, IL-3, GM-CSF, erythropoietin, thrombopoietin, etc In addition to, or instead of growth factors, the subject cells may be grown in a co-culture with fibroblasts, stromal or other feeder layer cells. Stromal cells suitable for use in the growth of hematopoietic cells are known in the art. These include bone marrow stroma as used in "Whitlock-Witte" (Whitlock et al. [1985] *Annu Rev Immunol* 3:213-235) or "Dexter" culture conditions (Dexter et al. [1977] *J Exp Med* 145:1612-1616); and heterogeneous thymic stromal cells.

Screening Assays

AMLSC expressing a marker or combination of markers of the present invention are also useful for in vitro assays and screening to detect factors and chemotherapeutic agents that are active on cancer stem cells. Of particular interest are screening assays for agents that are active on human cells. A wide variety of assays may be used for this purpose, including immunoassays for protein binding; determination of cell growth, differentiation and functional activity; production of factors; and the like. In other embodiments, isolated polypeptides corresponding to a marker or combination of markers of the present invention are useful in drug screening assays.

In screening assays for biologically active agents, antiproliferative drugs, etc. the marker or AMLSC composition is contacted with the agent of interest, and the effect of the agent assessed by monitoring output parameters on cells, such as expression of markers, cell viability, and the like; or binding efficacy or effect on enzymatic or receptor activity for polypeptides. The cells may be freshly isolated, cultured, genetically altered, and the like. The cells may be environmentally induced variants of clonal cultures: e.g. split into independent cultures and grown under distinct conditions, for example with or without drugs; in the presence or absence of cytokines or combinations thereof. The manner in which cells respond to an agent, particularly a pharmacologic agent, including the timing of responses, is an important reflection of the physiologic state of the cell.

Parameters are quantifiable components of cells, particularly components that can be accurately measured, desirably in a high throughput system. A parameter can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values.

Agents of interest for screening include known and unknown compounds that encompass numerous chemical classes, primarily organic molecules, which may include organometallic molecules, inorganic molecules, genetic sequences, etc. An important aspect of the invention is to evaluate candidate drugs, including toxicity testing; and the like.

In addition to complex biological agents candidate agents include organic molecules comprising functional groups necessary for structural interactions, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Included are pharmacologically active drugs, genetically active molecules, etc. Compounds of interest include chemotherapeutic agents, hormones or hormone antagonists, etc. Exemplary of pharmaceutical agents suitable for this invention are those described in, "The Pharmacological Basis of Therapeutics," Goodman and Gilman, McGraw-Hill, New York, N.Y., (1996), Ninth edition, under the sections: Water, Salts and Ions; Drugs Affecting Renal Function and Electrolyte Metabolism; Drugs Affecting Gastrointestinal Function; Chemotherapy of Microbial Diseases; Chemotherapy of Neoplastic Diseases; Drugs Acting on Blood-Forming organs; Hormones and Hormone Antagonists; Vitamins, Dermatology; and Toxicology, all incorporated herein by reference. Also included are toxins, and biological and chemical warfare agents, for example see Somani, S.M. (Ed.), "Chemical Warfare Agents," Academic Press, New York, 1992).

Test compounds include all of the classes of molecules described above, and may further comprise samples of unknown content. Of interest are complex mixtures of naturally occurring compounds derived from natural sources such as plants. While many samples will comprise compounds in solution, solid samples that can be dissolved in a suitable solvent may also be assayed. Samples of interest include environmental samples, e.g. ground water, sea water, mining waste, etc.; biological samples, e.g. lysates prepared from crops, tissue samples, etc.; manufacturing samples, e.g. time course during preparation of pharmaceuticals; as well as libraries of compounds prepared for analysis; and the like. Samples of interest include compounds being assessed for potential therapeutic value, i.e. drug candidates.

The term "samples" also includes the fluids described above to which additional components have been added, for example components that affect the ionic strength, pH, total protein concentration, etc. In addition, the samples may be treated to achieve at least partial fractionation or concentration. Biological samples may be stored if care is taken to reduce degradation of the compound, e.g. under nitrogen, frozen, or a combination thereof. The volume of sample used is sufficient to allow for measurable detection, usually from about 0.1 to 1 ml of a biological sample is sufficient.

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Agents are screened for biological activity by adding the agent to at least one and usually a plurality of cell samples, usually in conjunction with cells lacking the agent. The change in parameters in response to the agent is measured, and the result evaluated by comparison to reference cultures, e.g. in the presence and absence of the agent, obtained with other agents, etc.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

Preferred agent formulations do not include additional components, such as preservatives, that may have a significant effect on the overall formulation. Thus preferred formulations consist essentially of a biologically active compound and a physiologically acceptable carrier, e.g. water, ethanol, DMSO, etc. However, if a compound is liquid without a solvent, the formulation may consist essentially of the compound itself.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

Various methods can be utilized for quantifying the presence of the selected markers. For measuring the amount of a molecule that is present, a convenient method is to label a molecule with a detectable moiety, which may be fluorescent, luminescent, radioactive, enzymatically active, etc., particularly a molecule specific for binding to the parameter with high affinity. Fluorescent moieties are readily available for labeling virtually any biomolecule, structure, or cell type. Immunofluorescent moieties can be directed to bind not only to specific proteins but also specific conformations, cleavage products, or site modifications like phosphorylation. Individual peptides and proteins can be engineered to autofluoresce, e.g. by expressing them as green fluorescent protein chimeras inside cells (for a review see Jones et al. (1999) *Trends Biotechnol.* 17(12):477-81). Thus, antibodies can be genetically modified to provide a fluorescent dye as part of their structure. Depending upon the label chosen, parameters may be measured using other than fluorescent labels, using such immunoassay techniques as radioimmunoassay (RIA) or enzyme linked immunosorbance assay (ELISA), homogeneous enzyme immunoassays, and related non-enzymatic techniques. The quantitation of nucleic acids, especially messenger RNAs, is also of interest as a parameter. These can be measured by hybridization techniques that depend on the sequence of nucleic acid nucleotides. Techniques include polymerase chain reaction methods as well as gene array techniques. See Current Protocols in Molecular Biology, Ausubel et al., eds, John Wiley & Sons, New York, N.Y., 2000; Freeman et al. (1999) *Biotechniques* 26(1):112-225; Kawamoto et al. (1999) *Genome Res* 9(12):1305-12; and Chen et al. (1998) *Genomics* 51(3): 313-24, for examples.

Depletion of AMLSC

Depletion of AMLSC is useful in the treatment of AML. Depletion can be achieved by several methods. Depletion is defined as a reduction in the target population by up to about 30%, or up to about 40%, or up to about 50%, or up to about 75% or more. An effective depletion is usually determined by the sensitivity of the particular disease condition to the levels of the target population. Thus in the treatment of certain conditions a depletion of even about 20% could be beneficial.

A marker-specific agent that specifically depletes the targeted AMLSC is used to contact the patient blood in vitro or in vivo, wherein after the contacting step, there is a reduction in the number of viable AMLSC in the targeted population. An exemplary agent for such purposes is an antibody that specifically binds to a marker or combination of markers of the present invention on the surface of the targeted AMLSC. An effective dose of antibodies for such a purpose is sufficient to decrease the targeted population to the desired level, for example as described above. Antibodies for such purposes may have low antigenicity in humans or may be humanized antibodies.

In one embodiment of the invention, antibodies for depleting target population are added to patient blood in vivo. In another embodiment, the antibodies are added to the patient blood ex vivo. Beads coated with the antibody of interest can be added to the blood, target cells bound to these beads can then be removed from the blood using procedures common in the art. In one embodiment the beads are magnetic and are removed using a magnet. Alternatively, when the antibody is biotinylated, it is also possible to indirectly immobilize the antibody onto a solid phase which has adsorbed avidin, streptavidin, or the like. The solid phase, usually agarose or sepharose beads are separated from the blood by brief centrifugation. Multiple methods for tagging antibodies and removing such antibodies and any cells bound to the antibodies are routine in the art. Once the desired degree of depletion has been achieved, the blood is returned to the patient. Depletion of target cells ex vivo decreases the side effects such as infusion reactions associated with the intravenous administration. An additional advantage is that the repertoire of available antibodies is expanded significantly as this procedure does not have to be limited to antibodies with low antigenicity in humans or humanized antibodies.

In some embodiments, the antibodies for depletion are bispecific antibodies.

"Bispecific antibody" and "bispecific antibodies," also known as bifunctional antibodies, refers to antibodies that recognize two different antigens by virtue of possessing at least one first antigen combining site specific for a first antigen or hapten, and at least one second antigen combining site specific for a second antigen or hapten. Such antibodies can be produced by recombinant DNA methods or include, but are not limited to, antibodies produced chemically by methods known in the art. Bispecific antibodies include all antibodies or conjugates of antibodies, or polymeric forms of antibodies which are capable of recognizing two different antigens. Bispecific antibodies include antibodies that have been reduced and reformed so as to retain their bivalent characteristics and to antibodies that have been chemically coupled so that they can have several antigen recognition sites for each antigen.

Bispecific antibodies for use in the methods of the present invention bind to at least one of the AMLSC antigens described herein, and may bind to two or more AMLSC antigens described herein. Antigen combinations of interest include, without limitation, CD47+CD96, CD47+CD99, CD47+Tim3, CD47+CD97, CD97+TIM3. In some embodiments, one specificity of the antibody has a low affinity, e.g. less than about $10^{-9}$ binding constant, usually less than about $10^{-8}$ binding constant, and may be more than about $10^{-7}$ binding constant.

Antibodies suitable for practicing the methods of the invention are preferably monoclonal and multivalent, and may be human, humanized or chimeric antibodies, comprising single chain antibodies, Fab fragments, F(ab') fragments, fragments produced by a Fab expression library, and/or binding fragments of any of the above. In certain embodiments of the invention, the antibodies are human antigen-binding antibody fragments of the present invention and include, but are not limited to, Fab, Fab' and F(ab')$_2$, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, $CH_1$, $CH_2$, $CH_3$ and CL domains. Also included in the invention are antigen-binding fragments comprising any combination of variable region(s) with a hinge region, $CH_1$, $CH_2$, $CH_3$ and CL domains. Preferably, the antibodies are human, murine (e.g., mouse and rat), donkey, sheep, rabbit, goat, guinea pig, camelid, horse, or chicken. As used herein, "human" antibodies include antibodies having the amino acid sequence of a human immunoglobulin and include antibodies isolated from human immunoglobulin libraries, from human B cells, or from animals transgenic for one or more human immunoglobulins.

The antibodies suitable for practicing the methods of the present invention may be bispecific, trispecific or of greater multispecificity. Further, the antibodies of the present invention may have low risk of toxicity against granulocyte (neutrophil), NK cells, and CD4$^+$ cells as bystander cells.

Methods for making bispecific antibodies are known in the art. Traditional production of full length bispecific antibodies is based on the coexpression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al, EMBO J., 10:3655-3659 (1991).

According to another approach described in WO96/27011, the interface between a pair of antibody molecules can be engineered to maximize the percentage of heterodimers which are recovered from recombinant cell culture. Such interfaces may comprise at least a part of the $CH_3$ domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers. An alternative method links two different single chain variable regions to heat stable antigen (HSA). Using HSA as linker increases serum half life, and has the benefit of low immunogenicity.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoet-hylamine and is mixed with an equimolar amount of the other Fab'-TNB derivative to form the bispecific antibody. The bispecific antibodies produced can be used as agents for the selective immobilization of enzymes.

Various techniques for making and isolating bispecific antibody fragments directly from recombinant cell culture have also been described. For example, bispecific antibodies have been produced using leucine zippers. Kos-telny et al., J. Immunol, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., J. Immunol., 152:5368 (1994). Alternatively, the antibodies can be "linear antibodies" as described in Zapata et al. Protein Eng. 8(10): 1057-1062 (1995). Briefly, these antibodies comprise a pair of tandem Fd segments ($V_H$ —$C_{H1}$— $V_H$ —$C_H1$) which form a pair of antigen binding regions. Linear antibodies can be bispecific or monospecific.

Within the context of the present invention, antibodies are understood to include monoclonal antibodies and polyclonal antibodies, antibody fragments (e.g., Fab and F(ab')$_2$), chimeric antibodies bifunctional or bispecific antibodies and tetrameric antibody complexes. Antibodies are understood to be reactive against a selected antigen on the surface of a T cell if they bind with an appropriate affinity (association constant), e.g. greater than or equal to $10^7 M^{-1}$. Additionally, antibodies that may be used in the methods of the present invention may also be described or specified in terms of their binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-9}$ M, $5-10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, $10^{-15}$ M.

Antibodies can be fragmented using conventional techniques and the fragments screened for utility in the same manner as described above for the whole antibodies. For example, F(ab')$_2$ fragments can be generated by treating antibody with pepsin. The resulting F(ab')$_2$ fragment can be treated to reduce disulfide bridges to produce Fab' fragments.

The invention also contemplates chimeric antibody derivatives, i.e., antibody molecules that combine a non-human animal variable region and a human constant region. Chimeric antibody molecules can include, for example, the antigen binding domain from an antibody of a mouse, rat, or other species, with human constant regions. A variety of approaches for making chimeric antibodies have been described and can be used to make chimeric antibodies containing the immunoglobulin variable region which recognizes the selected antigens on the surface of differentiated cells or tumor cells. See, for example, Morrison et al., 1985; Proc. Natl. Acad. Sci. U.S.A. 81,6851; Takeda et al., 1985, Nature 314:452; Cabilly et al., U.S. Pat. No. 4,816,567; Boss et al., U.S. Pat. No. 4,816,397; Tanaguchi et al., European Patent Publication EP171496; European Patent Publication 0173494, United Kingdom patent GB 2177096B.

Chemical conjugation is based on the use of homo- and heterobifunctional reagents with E-amino groups or hinge region thiol groups. Homobifunctional reagents such as 5,5'-Dithiobis(2-nitrobenzoic acid)(DNTB) generate disulfide bonds between the two Fabs, and 0-phenylenedimaleimide (O-PDM) generate thioether bonds between the two Fabs (Brenner et al., 1985, Glennie et al., 1987). Heterobifunctional reagents such as N-succinimidyl-3-(2-pyridylditio)propionate (SPDP) combine exposed amino groups of antibodies and Fab fragments, regardless of class or isotype (Van Dijk et al., 1989).

The antibodies of the invention, i.e., antibodies that are useful for treating cancers, as well as other cancer comprising cancer stem cells expressing antigens set forth in Table 1, include derivatives that are modified, i.e., by the covalent attachment of any type of molecule to the antibody such that covalent attachment does not prevent the antibody from binding to the antigens. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

Kits may be provided, where the kit will comprise staining reagents that are sufficient to differentially identify the AMLSC described herein. A combination of interest may include one or more reagents specific for a marker or combination of markers of the present invention, and may further include antibodies specific for CD96, CD34, and CD38. The staining reagents are preferably antibodies, and may be detectably labeled. Kits may also include tubes, buffers, etc., and instructions for use.

Each publication cited in this specification is hereby incorporated by reference in its entirety for all purposes.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents Experimental

EXAMPLE 1

Identification of Cell Surface Molecules Preferentially Expressed on Human Acute Myeloid Leukemia Stem Cells Compared to Their Normal Counterparts Prospective Identification of a Human Multipotent Progenitor, the Cell of Origin for AML LSC. Identification of cell surface molecules that are preferentially expressed on AML LSC would be greatly facilitated by determining the cell within the normal hematopoietic hierarchy that undergoes transformation to become an AML LSC. The prevailing view in the field has been that AML LSC arise out of hematopoietic stem cells (HSC), since both stem cell populations are enriched in Lin−CD34+CD38− cells. However, human HSC have been shown to express CD90, while AML LSC are CD90−. Furthermore, HSC from long-term remission t(8;21) AML patients were found to contain the AML1-ETO translocation product, suggesting that the HSC were pre-leukemic, and that full transformation to AML LSC occurred in a downstream progenitor.

While it is certainly possible that HSC are in fact the cell of origin for AML LSC, and that these cells lose expression of CD90 as a consequence of transformation, it is also possible that AML LSC originate from downstream Lin−CD34+CD38−CD90− cells. We utilized a NOD/SCID/IL-2R gamma null (NOG) newborn xenotransplantation model to assay the function of subpopulations of Lin−CD34+CD38− cord blood, identified on the basis of CD90 and CD45RA expression. Lin−CD34+CD38−CD90+ cells produced long-term multi-lineage engraftment and formed successful secondary transplants, and therefore contained HSC. Transplantation of purified Lin−CD34+CD38−CD90−CD45RA− cells resulted in lower levels of multi-lineage engraftment in primary recipients, and a statistically significant reduced ability to form long-term secondary transplants. In fact, with transplantation of 50 purified cells, these cells failed to long-term engraft, unlike the Lin−CD34+CD38−CD90+ HSC. Thus, Lin−CD34+CD38−CD90−CD45RA− cells are multipotent and possess limited self-renewal ability. These cells are termed multipotent progenitors (MPP) and represent the possible cell of origin of AML LSC.

Use of Gene Expression Profiling to Identify Cell Surface Molecules Preferentially Expressed on AML LSC Compared to Their Normal Counterparts, HSC and MPP. Cell surface molecules preferentially expressed on human acute myeloid leukemia stem cells (AML LSC) compared to their normal counterparts have therapeutic applications outlined below. One strategy to identify such molecules has been to generate gene expression profiles of AML LSC and normal HSC and MPP, and compare them for differentially expressed genes.

Normal bone marrow HSC and MPP (n=4) and AML LSC (n=9) were purified by FACS. Total RNA was prepared, amplified, and hybridized to Affymetrix human DNA microarrays. Statistical analysis identified 4037 genes differentially expressed between HSC and LSC, and 4208 genes differentially expressed between MPP and LSC, with $p<0.05$ and a False Discovery Rate of 5% (FIG. 1A). Investigation of these differentially expressed genes identified 288 and 318 cell surface molecules preferentially expressed in AML LSC by at least 2-fold compared to HSC and MPP, respectively. Selected members of this list, including many with the greatest preferential expression in AML LSC are indicated (FIG. 1B, Table 1).

TABLE 1

| Fold Change | Genbank | Gene Symbol | Description |
|---|---|---|---|
| 94.34 | M27331 | TRGC2 | T cell receptor gamma constant 2 |
| 57.47 | NM_005816 | CD96 | CD96 antigen |
| 47.17 | AI862120 | MAMDC2 | MAM domain containing 2 |
| 32.36 | AF348078 | SUCNR1 | succinate receptor 1 |
| 32.05 | M16768 | TRGC2 | T cell receptor gamma constant 2 |
| 30.96 | NM_002182 | IL1RAP | interleukin 1 receptor accessory protein |
| 29.85 | M13231 | TRGC2 | T cell receptor gamma constant 2 |
| 27.55 | NM_003332 | TYROBP | TYRO protein tyrosine kinase binding protein |
| 26.88 | NM_004271 | LY86 | lymphocyte antigen 86 |
| 20.96 | NM_014879 | P2RY14 | purinergic receptor P2Y, G-protein coupled, 14 |
| 18.38 | BC020749 | CD96 | CD96 antigen |
| 18.38 | NM_005048 | PTHR2 | parathyroid hormone receptor 2 |
| 17.73 | AI625747 | ADRB1 | Adrenergic, beta-1-, receptor |
| 17.36 | NM_015376 | RASGRP3 | RAS guanyl releasing protein 3 (calcium and DAG-regulated) |
| 16.84 | U62027 | C3AR1 | complement component 3a receptor 1 |
| 14.49 | AW025572 | HAVCR2 | hepatitis A virus cellular receptor 2 |
| 12.48 | AF285447 | HCST | hematopoietic cell signal transducer |
| 11.92 | AI805323 | LGR7 | leucine-rich repeat-containing G protein-coupled receptor 7 |
| 11.67 | NM_001197 | BIK | BCL2-interacting killer (apoptosis-inducing) |
| 11.53 | NM_018092 | NETO2 | neuropilin (NRP) and tolloid (TLL)-like 2 |
| 11.07 | N74607 | AQP3 | aguaporin 3 |
| 10.88 | BF439675 | CD69 | CD69 antigen (p60, early T-cell activation antigen) |
| 10.48 | NM_001769 | CD9 | CD9 antigen (p24) |
| 10.32 | AF167343 | IL1RAP | interleukin 1 receptor accessory protein |
| 9.52 | AA814140 | C5orf18 | chromosome 5 open reading frame 18 |
| 8.77 | NM_005582 | CD180 | CD180 antigen |
| 7.46 | AF039686 | GPR34 | G protein-coupled receptor 34 |

TABLE 1-continued

| Fold Change | Genbank | Gene Symbol | Description |
|---|---|---|---|
| 7.30 | AI056776 | ITGA6 | Integrin, alpha 6 |
| 7.19 | AJ277151 | TNFRSF4 | tumor necrosis factor receptor superfamily, member 4 |
| 6.99 | AI738675 | SELPLG | Selectin P ligand |
| 6.85 | AA888858 | PDE3B | Phosphodiesterase 3B, cGMP-inhibited |
| 6.80 | AU149572 | ADCY2 | adenylate cyclase 2 (brain) |
| 6.80 | NM_002299 | LCT | lactase |
| 6.58 | NM_005296 | GPR23 | G protein-coupled receptor 23 |
| 6.45 | NM_004106 | FCER1G | Fc fragment of IgE, high affinity receptor |
| 6.29 | AI741056 | SELPLG | selectin P ligand |
| 6.25 | AW406569 | MGC15619 | |
| 6.06 | M81695 | ITGAX | integrin, alpha X |
| 5.92 | NM_003494 | DYSF | dysferlin |
| 5.85 | AI860212 | PAG1 | phosphoprotein associated with glycosphingolipid microdomains 1 |
| 5.75 | NM_013447 | EMR2 | egf-like module containing, mucin-like, hormone receptor-like 2 |
| 5.62 | NM_017806 | LIME1 | Lck interacting transmembrane adaptor 1 |
| 5.62 | AK092824 | AMN | Amnionless homolog (mouse) |
| 5.59 | AF345567 | GPR174 | G protein-coupled receptor 174 |
| 5.29 | BC041928 | IL1RAP | Interleukin 1 receptor accessory protein |
| 5.26 | L03419 | FCGR1A | Fc fragment of IgG, high affinity Ia, receptor (CD64); Fc-gamma receptor I B2 |
| 5.24 | BG230586 | SLC7A6 | solute carrier family 7 (cationic amino acid transporter, y+ system), member 6 |
| 5.18 | AF015524 | CCRL2 | chemokine (C-C motif) receptor-like 2 |
| 5.13 | AA631143 | SLC45A3 | solute carrier family 45, member 3 |
| 5.10 | AJ240085 | TRAT1 | T cell receptor associated transmembrane adaptor 1 |
| 5.05 | AW183080 | GPR92 | G protein-coupled receptor 92 |
| 5.03 | NM_002120 | HLA-DOB | major histocompatibility complex, class II, DO beta |
| 5.03 | NM_015364 | LY96 | lymphocyte antigen 96 |
| 4.90 | NM_020399 | GOPC | golgi associated PDZ and coiled-coil motif containing |
| 4.88 | AK026133 | SEMA4B | semaphorin |
| 4.88 | BC041664 | VMD2 | vitelliform macular dystrophy 2 |
| 4.85 | NM_152592 | C14orf49 | chromosome 14 open reading frame 49 |
| 4.85 | AA923524 | RASGRP4 | RAS guanyl releasing protein 4 |
| 4.85 | BC008777 | ITGAL | integrin, alpha L) |
| 4.67 | AF014403 | PPAP2A | phosphatidic acid phosphatase type 2A |
| 4.65 | AK097698 | SORCS2 | Sortilin-related VPS10 domain containing receptor 2 |
| 4.63 | X14355 | FCGR1A | Fc fragment of IgG, high affinity Ia, receptor (CD64) |
| 4.55 | NM_001629 | ALOX5AP | arachidonate 5-lipoxygenase-activating protein |
| 4.50 | AU155968 | C18orf1 | chromosome 18 open reading frame 1 |
| 4.44 | AK075092 | HERV-FRD | HERV-FRD provirus ancestral Env polyprotein |
| 4.42 | NM_020960 | GPR107 | G protein-coupled receptor 107 |
| 4.37 | BC000039 | FAM26B | family with sequence similarity 26, member B |
| 4.35 | NM_153701 | IL12RB1 | interleukin 12 receptor, beta 1 |
| 4.35 | AI762344 | PTGER1 | prostaglandin E receptor 1 (subtype EP1), 42 kDa |
| 4.31 | NM_006459 | SPFH1 | SPFH domain family, member 1 |
| 4.27 | NM_003126 | SPTA1 | spectrin, alpha, erythrocytic 1 (elliptocytosis 2) |
| 4.22 | AL518391 | AQP1 | aquaporin 1 (channel-forming integral protein, 28 kDa) |
| 4.12 | AK026188 | PCDHGC3 | protocadherin gamma subfamily C |
| 4.10 | AU146685 | EDG2 | Endothelial differentiation, lysophosphatidic acid G-protein-coupled receptor, 2 |
| 4.05 | BE673587 | SLC14A1 | Solute carrier family 14 (urea transporter), member 1 (Kidd blood group) |
| 4.02 | BF129969 | TSPAN2 | tetraspanin 2 |
| 4.00 | AW243272 | KCNK5 | Potassium channel, subfamily K, member 5 |
| 3.98 | T68858 | DHRS3 | Dehydrogenase/reductase (SDR family) member 3 |
| 3.94 | AI827849 | VTI1A | Vesicle transport through interaction with t-SNAREs homolog 1A (yeast) |
| 3.86 | AL134012 | NRXN2 | Neurexin 2 |
| 3.83 | BG230614 | CD47 | CD47 antigen |
| 3.80 | AI869717 | MGC15523 | MGC15523 |
| 3.80 | AI458583 | SIMP | Source of immunodominant MHC-associated peptides |
| 3.79 | NM_002183 | IL3RA | interleukin 3 receptor, alpha (low affinity) |
| 3.79 | AA608820 | NRXN2 | neurexin 2 |
| 3.73 | NM_000206 | IL2RG | interleukin 2 receptor |
| 3.72 | BC002737 | VAMP2 | synaptobrevin 2 |
| 3.72 | BC005884 | BID | BH3 interacting domain death agonist; BH3 interacting domain death agonist |
| 3.68 | AI688418 | PLXNA2 | plexin A2 |
| 3.68 | BC003105 | PTP4A3 | protein tyrosine phosphatase type IVA, member 3 |
| 3.68 | NM_001772 | CD33 | CD33 antigen (gp67) |
| 3.65 | BC007524 | SPAG9 | sperm associated antigen 9 |
| 3.64 | AI344200 | SLC25A35 | solute carrier family 25, member 35 |
| 3.64 | BC005253 | KLHL20 | kelch-like 20 (*Drosophila*) |
| 3.60 | AI335263 | NETO2 | neuropilin (NRP) and tolloid (TLL)-like 2 |
| 3.58 | BF381837 | C20orf52 | chromosome 20 open reading frame 52 |

TABLE 1-continued

| Fold Change | Genbank | Gene Symbol | Description |
|---|---|---|---|
| 3.51 | NM_002886 | RAP2A | RAP2A |
| 3.50 | NM_007063 | TBC1D8 | TBC1 domain family, member 8 (with GRAM domain) |
| 3.45 | AK027160 | BCL2L11 | BCL2-like 11 (apoptosis facilitator) |
| 3.44 | BF055366 | EDG2 | endothelial differentiation, lysophosphatidic acid G-protein-coupled receptor, 2 |
| 3.42 | NM_003608 | GPR65 | G protein-coupled receptor 65 |
| 3.41 | AI675453 | PLXNA3 | plexin A3 |
| 3.40 | AV734194 | DPP8 | dipeptidylpeptidase 8 |
| 3.38 | BC000232 | C5orf18 | chromosome 5 open reading frame 18 |
| 3.36 | BC001956 | KIAA1961 | KIAA1961 gene |
| 3.34 | NM_013332 | HIG2 | hypoxia-inducible protein 2 |
| 3.31 | BC029450 | SLC33A1 | Solute carrier family 33 (acetyl-CoA transporter), member 1 |
| 3.30 | AW008505 | C18orf1 | chromosome 18 open reading frame 1 |
| 3.29 | BF693956 | CD47 | CD47 antigen |
| 3.28 | BF677986 | KIAA1961 | KIAA1961 gene |
| 3.27 | AI433691 | CACNA2D4 | calcium channel, voltage-dependent, alpha 2/delta subunit 4 |
| 3.26 | AB014573 | NPHP4 | nephronophthisis 4 |
| 3.25 | AL582804 | LY9 | lymphocyte antigen 9 |
| 3.25 | BG236280 | CD86 | CD86 antigen |
| 3.24 | AA639289 | SLC26A7 | Solute carrier family 26, member 7 |
| 3.24 | NM_005211 | CSF1R | colony stimulating factor 1 receptor |
| 3.24 | AI051254 | TRPM2 | transient receptor potential cation channel, subfamily M, member 2 |
| 3.23 | AW292816 | ABHD2 | abhydrolase domain containing 2 |
| 3.23 | BC040275 | RASGRF1 | Ras protein-specific guanine nucleotide-releasing factor 1 |
| 3.22 | NM_021911 | GABRB2 | gamma-aminobutyric acid (GABA) A receptor, beta 2 |
| 3.19 | AI660619 | SLC7A6 | solute carrier family 7 (cationic amino acid transporter, y+ system), member 6 |
| 3.19 | NM_001860 | SLC31A2 | solute carrier family 31 (copper transporters), member 2 |
| 3.18 | NM_015680 | C2orf24 | chromosome 2 open reading frame 24 |
| 3.17 | AW058600 | SLC36A1 | solute carrier family 36 |
| 3.16 | AU145049 | HIP1 | Huntingtin interacting protein 1 |
| 3.15 | NM_005770 | SERF2 | small EDRK-rich factor 2 |
| 3.15 | NM_003566 | EEA1 | Early endosome antigen 1, 162 kD |
| 3.14 | NM_020041 | SLC2A9 | solute carrier family 2 (facilitated glucose transporter), member 9 |
| 3.14 | W90718 | SLC24A4 | solute carrier family 24 |
| 3.13 | AI423165 | TICAM2 | toll-like receptor adaptor molecule 2 |
| 3.12 | AI674647 | SPPL2A | signal peptide peptidase-like 2A |
| 3.11 | NM_004121 | GGTLA1 | gamma-glutamyltransferase-like activity 1 |
| 3.10 | NM_004546 | NDUFB2 | NADH dehydrogenase (ubiquinone) 1 beta subcomplex, 2, 8 kDa |
| 3.05 | X15786 | RET | ret proto-oncogene (multiple endocrine neoplasia and medullary thyroid carcinoma 1, Hirschsprung disease) |
| 3.05 | AF181660 | MPZL1 | myelin protein zero-like 1 |
| 3.05 | BG230614 | CD47 | CD47 antigen (Rh-related antigen, integrin-associated signal transducer) |
| 3.00 | AI571996 | STAM2 | signal transducing adaptor molecule (SH3 domain and ITAM motif) 2 |
| 2.99 | NM_000201 | ICAM1 | intercellular adhesion molecule 1 (CD54), human rhinovirus receptor |
| 2.93 | NM_025244 | TSGA10 | testis specific, 10 |
| 2.93 | AU147538 | PRKCE | Protein kinase C, epsilon |
| 2.92 | NM_024576 | OGFRL1 | opioid growth factor receptor-like 1 |
| 2.91 | AI248055 | ABCC4 | ATP-binding cassette, sub-family C (CFTR/MRP), member 4 |
| 2.86 | AA503877 | CEPT1 | Choline/ethanolamine phosphotransferase 1 |
| 2.84 | BC030993 | FLJ21127 | Hypothetical protein FLJ21127 |
| 2.82 | AA829818 | LY86 | Lymphocyte antigen 86 |
| 2.82 | NM_001859 | SLC31A1 | solute carrier family 31 (copper transporters), member 1 |
| 2.81 | M74721 | CD79A | CD79A antigen (immunoglobulin-associated alpha) |
| 2.79 | AI986112 | MGAT4B | Mannosyl (alpha-1,3-)-glycoprotein beta-1,4-N-acetylglucosaminyltransferase, isoenzyme B |
| 2.79 | NM_030930 | UNC93B1 | unc-93 homolog B1 (*C. elegans*); unc-93 homolog B1 (*C. elegans*) |
| 2.79 | X74039 | PLAUR | plasminogen activator, urokinase receptor |
| 2.78 | BF514291 | LY86 | Lymphocyte antigen 86 |
| 2.75 | BC005253 | KLHL20 | kelch-like 20 (*Drosophila*) |
| 2.73 | AB036432 | AGER | advanced glycosylation end product-specific receptor |
| 2.71 | NM_007245 | ATXN2L | ataxin 2-like |
| 2.71 | NM_016072 | GOLT1B | golgi transport 1 homolog B (*S. cerevisiae*) |
| 2.71 | AI453548 | ZDHHC8 | zinc finger, DHHC-type containing 8 |
| 2.70 | AI636233 | TMEM8 | transmembrane protein 8 (five membrane-spanning domains) |
| 2.69 | BE502509 | T3JAM | TRAF3 interacting protein 3 |

TABLE 1-continued

| Fold Change | Genbank | Gene Symbol | Description |
|---|---|---|---|
| 2.69 | AW117765 | PEX13 | peroxisome biogenesis factor 13 |
| 2.69 | AW052216 | IL17RB | Interleukin 17 receptor B |
| 2.67 | NM_003853 | IL18RAP | interleukin 18 receptor accessory protein |
| 2.66 | NM_002490 | NDUFA6 | NADH dehydrogenase (ubiquinone) 1 alpha subcomplex, 6, 14 kDa |
| 2.65 | NM_016639 | TNFRSF12A | tumor necrosis factor receptor superfamily, member 12A |
| 2.65 | AI363185 | FLJ20255 | Hypothetical protein FLJ20255 |
| 2.65 | NM_052931 | SLAMF6 | SLAM family member 6 |
| 2.65 | AW571669 | TNFRSF19L | tumor necrosis factor receptor superfamily, member 19-like |
| 2.64 | AA654142 | CEECAM1 | cerebral endothelial cell adhesion molecule 1 |
| 2.62 | AW510783 | TMEM63A | transmembrane protein 63A |
| 2.61 | W95007 | ACSL4 | Acyl-CoA synthetase long-chain family member 4 |
| 2.60 | S76475 | NTRK3 | neurotrophic tyrosine kinase, receptor, type 3 |
| 2.60 | AJ130713 | SIGLEC7 | sialic acid binding Ig-like lectin 7 |
| 2.56 | NM_003775 | EDG6 | endothelial differentiation, G-protein-coupled receptor 6 |
| 2.55 | AI978986 | MAMDC4 | MAM domain containing 4 |
| 2.54 | AF010447 | MR1 | major histocompatibility complex, class I-related |
| 2.54 | NM_006068 | TLR6 | toll-like receptor 6 |
| 2.53 | AF041811 | NTRK3 | neurotrophic tyrosine kinase, receptor, type 3 |
| 2.53 | AW953521 | SERF2; HYPK | small EDRK-rich factor 2; Huntingtin interacting protein K |
| 2.51 | AW293276 | CD53 | CD53 antigen |
| 2.49 | AK023058 | PLXNA2 | Plexin A2 |
| 2.49 | AI125204 | C6orf128 | chromosome 6 open reading frame 128 |
| 2.49 | NM_000392 | ABCC2 | ATP-binding cassette, sub-family C (CFTR/MRP), member 2 |
| 2.46 | BC032474 | TIRAP | toll-interleukin 1 receptor (TIR) domain containing adaptor protein |
| 2.44 | NM_031211 | IMAA | SLC7A5 pseudogene |
| 2.44 | AI797836 | CD5 | CD5 antigen (p56-62) |
| 2.41 | W72082 | C1QR1 | complement component 1 |
| 2.40 | AA708616 | DPP9 | dipeptidylpeptidase 9 |
| 2.40 | BM987094 | DLGAP4 | discs, large (*Drosophila*) homolog-associated protein 4 |
| 2.40 | AL713719 | LOC283501 | ATPase, Class VI, type 11A |
| 2.39 | AI628734 | PRLR | prolactin receptor |
| 2.39 | NM_012110 | CHIC2 | cysteine-rich hydrophobic domain 2 |
| 2.38 | AK022002 | TFR2 | transferrin receptor 2 |
| 2.37 | NM_001555 | IGSF1 | immunoglobulin superfamily, member 1 |
| 2.36 | AA426091 | C19orf15 | chromosome 19 open reading frame 15 |
| 2.36 | BE547542 | GOPC | golgi associated PDZ and coiled-coil motif containing |
| 2.36 | NM_004231 | ATP6V1F | ATPase, H+ transporting, lysosomal 14 kDa, V1 subunit F |
| 2.36 | AJ130712 | SIGLEC7 | sialic acid binding Ig-like lectin 7 |
| 2.36 | NM_017905 | TMCO3 | transmembrane and coiled-coil domains 3 |
| 2.35 | AB054985 | CACNB1 | calcium channel, voltage-dependent, beta 1 subunit |
| 2.35 | NM_005003 | NDUFAB1 | NADH dehydrogenase (ubiquinone) 1, alpha/beta subcomplex, 1, 8 kDa |
| 2.35 | NM_001251 | CD68 | CD68 antigen |
| 2.35 | AA700869 | PSCD2 | Pleckstrin homology, Sec7 and coiled-coil domains 2 (cytohesin-2) |
| 2.35 | U94903 | CD44 | CD44 antigen (homing function and Indian blood group system) |
| 2.35 | NM_003841 | TNFRSF10C | tumor necrosis factor receptor superfamily, member 10c, decoy without an intracellular domain |
| 2.33 | NM_004541 | NDUFA1 | NADH dehydrogenase (ubiquinone) 1 alpha subcomplex, 1, 7.5 kDa |
| 2.33 | BE567130 | KLRK1 | Killer cell lectin-like receptor subfamily K, member 1 |
| 2.31 | NM_017460 | CYP3A4 | cytochrome P450, family 3, subfamily A, polypeptide 4 |
| 2.31 | AI339536 | DSC1 | Desmocollin 1 |
| 2.31 | NM_001783 | CD79A | CD79A antigen (immunoglobulin-associated alpha); CD79A antigen (immunoglobulin-associated alpha) |
| 2.30 | AA333161 | VTI1A | vesicle transport through interaction with t-SNAREs homolog 1A (yeast) |
| 2.30 | AW134823 | CD6 | CD6 antigen; CD6 antigen |
| 2.30 | AL137537 | ATP8B2 | ATPase, Class I, type 8B, member 2 |
| 2.29 | AI671983 | SLC2A9 | solute carrier family 2 (facilitated glucose transporter), member 9 |
| 2.29 | AA018187 | C22orf3 | chromosome 22 open reading frame 3 |
| 2.29 | AL117415 | ADAM33 | ADAM metallopeptidase domain 33 |
| 2.29 | NM_002588 | PCDHGC3 | protocadherin gamma subfamily C |
| 2.29 | NM_020960 | GPR107 | G protein-coupled receptor 107 |
| 2.29 | AK074635 | GENX-3414 | Genethonin 1 |
| 2.29 | BE138575 | ITGB5 | Integrin, beta 5 |
| 2.28 | NM_003830 | SIGLEC5 | sialic acid binding Ig-like lectin 5; sialic acid binding Ig-like lectin 5 |
| 2.28 | NM_013319 | UBIAD1 | UbiA prenyltransferase domain containing 1 |
| 2.28 | M63889 | FGFR1 | fibroblast growth factor receptor 1 (fms-related tyrosine kinase 2, Pfeiffer syndrome) |

TABLE 1-continued

| Fold Change | Genbank | Gene Symbol | Description |
|---|---|---|---|
| 2.27 | H67156 | MSCP | Solute carrier family 25, member 37 |
| 2.27 | BC006215 | SMEK2 | KIAA1387 protein; KIAA1387 protein |
| 2.27 | AL109653 | SLITRK2 | SLIT and NTRK-like family, member 2 |
| 2.27 | NM_007011 | ABHD2 | abhydrolase domain containing 2 |
| 2.26 | AI767210 | MGC11332 | Hypothetical protein MGC11332 |
| 2.26 | BF723605 | NRCAM | Neuronal cell adhesion molecule |
| 2.26 | R08129 | CDA08 | T-cell immunomodulatory protein |
| 2.26 | AF052059 | SEL1L | sel-1 suppressor of lin-12-like (*C. elegans*) |
| 2.26 | NM_005729 | PPIF | peptidylprolyl isomerase F (cyclophilin F) |
| 2.25 | BE858032 | ARL2L1 | ADP-ribosylation factor-like 2-like 1 |
| 2.25 | AI950390 | C14orf118 | Chromosome 14 open reading frame 118 |
| 2.24 | NM_017767 | SLC39A4 | solute carrier family 39 (zinc transporter), member 4 |
| 2.24 | AL110273 | SPTAN1 | Spectrin, alpha, non-erythrocytic 1 (alpha-fodrin) |
| 2.24 | AI077660 | CDA08 | T-cell immunomodulatory protein |
| 2.23 | AA488687 | SLC7A11 | solute carrier family 7, (cationic amino acid transporter, y+ system) member 11 |
| 2.23 | NM_000634 | IL8RA | interleukin 8 receptor, alpha |
| 2.22 | AL390177 | MGC34032 | Solute carrier family 44, member 5 |
| 2.21 | NM_001531 | MR1 | major histocompatibility complex, class I-related |
| 2.21 | NM_003183 | ADAM17 | ADAM metallopeptidase domain 17 (tumor necrosis factor, alpha, converting enzyme) |
| 2.20 | AC003999 | SCAP2 | src family associated phosphoprotein 2 |
| 2.20 | BC014416 | SLC33A1 | solute carrier family 33 (acetyl-CoA transporter), member 1 |
| 2.20 | AF226731 | ADORA3 | adenosine A3 receptor |
| 2.19 | AI608725 | ICAM1 | intercellular adhesion molecule 1 (CD54), human rhinovirus receptor |
| 2.19 | U41163 | SLC6A8; FLJ43855 | solute carrier family 6 (neurotransmitter transporter, creatine), member 8; similar to sodium- and chloride-dependent creatine transporter |
| 2.19 | AU147799 | LRRC15 | leucine rich repeat containing 15 |
| 2.18 | AW337166 | LOC255104 | Transmembrane and coiled-coil domains 4 |
| 2.18 | NM_006505 | PVR | poliovirus receptor |
| 2.18 | AI638420 | CLIC4 | chloride intracellular channel 4 |
| 2.18 | AI167482 | SCUBE3 | Signal peptide, CUB domain, EGF-like 3 |
| 2.18 | AI739514 | HAS3 | hyaluronan synthase 3 |
| 2.18 | NM_005971 | FXYD3 | FXYD domain containing ion transport regulator 3 |
| 2.17 | AL022398 | TRAF3IP3 | TRAF3 interacting protein 3 |
| 2.17 | U90940 | FCGR2C | Fc fragment of IgG, low affinity IIc, receptor for (CD32) |
| 2.16 | BC023540 | SORCS1 | Sortilin-related VPS10 domain containing receptor 1 |
| 2.16 | AV713913 | OSTM1 | osteopetrosis associated transmembrane protein 1 |
| 2.15 | NM_024505 | NOX5 | NADPH oxidase, EF-hand calcium binding domain 5 |
| 2.15 | BC006178 | SEC22L3 | SEC22 vesicle trafficking protein-like 3 (*S. cerevisiae*); SEC22 vesicle trafficking protein-like 3 (*S. cerevisiae*) |
| 2.15 | BG151527 | GRIK5 | glutamate receptor, ionotropic, kainate 5 |
| 2.14 | AW001754 | NEGR1 | neuronal growth regulator 1 |
| 2.14 | NM_013979 | BNIP1 | BCL2/adenovirus E1B 19 kDa interacting protein 1 |
| 2.14 | NM_018643 | TREM1 | triggering receptor expressed on myeloid cells 1 |
| 2.12 | NM_005284 | GPR6 | G protein-coupled receptor 6 |
| 2.11 | AA454190 | ZDHHC20 | zinc finger, DHHC-type containing 20 |
| 2.11 | AB048796 | TMPRSS13 | transmembrane protease, serine 13 |
| 2.11 | AL044520 | NYD-SP21 | testes development-related NYD-SP21 |
| 2.11 | BE463930 | TMAP1 | Matrix-remodelling associated 7 |
| 2.10 | NM_152264 | SLC39A13 | solute carrier family 39 (zinc transporter), member 13 |
| 2.08 | AL530874 | EPHB2 | EPH receptor B2 |
| 2.07 | NM_018668 | VPS33B | vacuolar protein sorting 33B (yeast) |
| 2.07 | NM_024531 | GPR172A | G protein-coupled receptor 172A |
| 2.07 | NM_023038 | ADAM19 | ADAM metallopeptidase domain 19 (meltrin beta) |
| 2.07 | BC001281 | TNFRSF10B | tumor necrosis factor receptor superfamily, member 10b |
| 2.07 | AF217749 | PCDHB9 | protocadherin beta 9 |
| 2.06 | AB030077 | FGFR2 | fibroblast growth factor receptor 2 (bacteria-expressed kinase, keratinocyte growth factor receptor, craniofacial dysostosis 1, Crouzon syndrome, Pfeiffer syndrome, Jackson-Weiss syndrome) |
| 2.06 | AL137432 | SUSD1 | sushi domain containing 1 |
| 2.05 | NM_004518 | KCNQ2 | potassium voltage-gated channel, KQT-like subfamily, member 2 |
| 2.04 | AI672363 | VPS33B | vacuolar protein sorting 33B (yeast) |
| 2.04 | NM_006671 | SLC1A7 | solute carrier family 1 (glutamate transporter), member 7 |
| 2.03 | AA215519 | DLGAP1 | Discs, large (*Drosophila*) homolog-associated protein 1 |
| 2.02 | NM_004648 | PTPNS1 | protein tyrosine phosphatase, non-receptor type substrate 1 |
| 2.02 | NM_002564 | P2RY2 | purinergic receptor P2Y, G-protein coupled, 2 |
| 2.01 | BF511678 | SCUBE3 | Signal peptide, CUB domain, EGF-like 3 |
| 2.01 | BC013385 | CLEC7A | C-type lectin domain family 7, member A |

TABLE 2

| Fold Change | Genbank | Gene Symbol | Description |
|---|---|---|---|
| 57.47 | NM_005816 | CD96 | CD96 antigen |
| 32.36 | AF348078 | SUCNR1 | succinate receptor 1 |
| 30.96 | NM_002182 | IL1RAP | interleukin 1 receptor accessory protein |
| 27.55 | NM_003332 | TYROBP | TYRO protein tyrosine kinase binding protein |
| 26.88 | NM_004271 | LY86 | lymphocyte antigen 86 |
| 20.96 | NM_014879 | P2RY14 | purinergic receptor P2Y, G-protein coupled, 14 |
| 18.38 | NM_005048 | PTHR2 | parathyroid hormone receptor 2 |
| 17.73 | AI625747 | ADRB1 | Adrenergic, beta-1-, receptor |
| 17.36 | NM_015376 | RASGRP3 | RAS guanyl releasing protein 3 (calcium and DAG-regulated) |
| 16.84 | U62027 | C3AR1 | complement component 3a receptor 1 |
| 14.49 | AW025572 | HAVCR2 | hepatitis A virus cellular receptor 2 |
| 12.48 | AF285447 | HCST | hematopoietic cell signal transducer |
| 11.92 | AI805323 | LGR7 | leucine-rich repeat-containing G protein-coupled receptor 7 |
| 11.67 | NM_001197 | BIK | BCL2-interacting killer (apoptosis-inducing) |
| 11.53 | NM_018092 | NETO2 | neuropilin (NRP) and tolloid (TLL)-like 2 |
| 11.07 | N74607 | AQP3 | aquaporin 3 |
| 10.48 | NM_001769 | CD9 | CD9 antigen (p24) |
| 8.77 | NM_005582 | CD180 | CD180 antigen |
| 7.46 | AF039686 | GPR34 | G protein-coupled receptor 34 |
| 7.19 | AJ277151 | TNFRSF4 | tumor necrosis factor receptor superfamily, member 4 |
| 6.85 | AA888858 | PDE3B | Phosphodiesterase 3B, cGMP-inhibited |
| 6.80 | AU149572 | ADCY2 | adenylate cyclase 2 (brain) |
| 6.80 | NM_002299 | LCT | lactase |
| 6.58 | NM_005296 | GPR23 | G protein-coupled receptor 23 |
| 6.45 | NM_004106 | FCER1G | Fc fragment of IgE, high affinity I, receptor for; gamma polypeptide |
| 6.25 | AW406569 | MGC15619 | hypothetical protein MGC15619 |
| 6.06 | M81695 | ITGAX | integrin, alpha X (antigen CD11C (p150), alpha polypeptide) |
| 5.92 | NM_003494 | DYSF | dysferlin, limb girdle muscular dystrophy 2B (autosomal recessive) |
| 5.75 | NM_013447 | EMR2 | egf-like module containing, mucin-like, hormone receptor-like 2 |
| 5.62 | NM_017806 | LIME1 | Lck interacting transmembrane adaptor 1 |
| 5.62 | AK092824 | AMN | Amnionless homolog (mouse) |
| 5.59 | AF345567 | GPR174 | G protein-coupled receptor 174 |
| 5.26 | L03419 | FCGR1A; LOC440607 | Fc fragment of IgG, high affinity Ia, receptor (CD64); Fc-gamma receptor I B2 |
| 5.18 | AF015524 | CCRL2 | chemokine (C-C motif) receptor-like 2 |
| 5.13 | AA631143 | SLC45A3 | solute carrier family 45, member 3 |
| 5.10 | AJ240085 | TRAT1 | T cell receptor associated transmembrane adaptor 1 |
| 5.05 | AW183080 | GPR92 | G protein-coupled receptor 92 |
| 5.03 | NM_002120 | HLA-DOB | major histocompatibility complex, class II, DO beta |
| 5.03 | NM_015364 | LY96 | lymphocyte antigen 96 |

TABLE 3

| Fold Change | Genbank | Gene Symbol | Description |
|---|---|---|---|
| 57.47 | NM_005816 | CD96 | CD96 antigen |
| 32.36 | AF348078 | SUCNR1 | succinate receptor 1 |
| 30.96 | NM_002182 | IL1RAP | interleukin 1 receptor accessory protein |
| 27.55 | NM_003332 | TYROBP | TYRO protein tyrosine kinase binding protein |
| 26.88 | NM_004271 | LY86 | lymphocyte antigen 86 |
| 20.96 | NM_014879 | P2RY14 | purinergic receptor P2Y, G-protein coupled, 14 |
| 18.38 | NM_005048 | PTHR2 | parathyroid hormone receptor 2 |
| 17.73 | AI625747 | ADRB1 | Adrenergic, beta-1-, receptor |
| 17.36 | NM_015376 | RASGRP3 | RAS guanyl releasing protein 3 (calcium and DAG-regulated) |
| 16.84 | U62027 | C3AR1 | complement component 3a receptor 1 |
| 14.49 | AW025572 | HAVCR2 | hepatitis A virus cellular receptor 2 |
| 12.48 | AF285447 | HCST | hematopoietic cell signal transducer |
| 11.92 | AI805323 | LGR7 | leucine-rich repeat-containing G protein-coupled receptor 7 |
| 11.67 | NM_001197 | BIK | BCL2-interacting killer (apoptosis-inducing) |
| 11.53 | NM_018092 | NETO2 | neuropilin (NRP) and tolloid (TLL)-like 2 |
| 11.07 | N74607 | AQP3 | aquaporin 3 |
| 10.88 | BF439675 | CD69 | CD69 antigen (p60, early T-cell activation antigen) |
| 10.48 | NM_001769 | CD9 | CD9 antigen (p24) |
| 9.52 | AA814140 | C5orf18 | chromosome 5 open reading frame 18 |
| 8.77 | NM_005582 | CD180 | CD180 antigen |
| 7.46 | AF039686 | GPR34 | G protein-coupled receptor 34 |

TABLE 3-continued

| Fold Change | Genbank | Gene Symbol | Description |
|---|---|---|---|
| 7.30 | AI056776 | ITGA6 | Integrin, alpha 6 |
| 7.19 | AJ277151 | TNFRSF4 | tumor necrosis factor receptor superfamily, member 4 |
| 6.99 | AI738675 | SELPLG | Selectin P ligand |
| 6.85 | AA888858 | PDE3B | Phosphodiesterase 3B, cGMP-inhibited |
| 6.80 | AU149572 | ADCY2 | adenylate cyclase 2 (brain) |
| 6.80 | NM_002299 | LCT | lactase |
| 6.58 | NM_005296 | GPR23 | G protein-coupled receptor 23 |
| 6.45 | NM_004106 | FCER1G | Fc fragment of IgE, high affinity I, receptor for; gamma polypeptide |
| 6.25 | AW406569 | MGC15619 | hypothetical protein MGC15619 |
| 6.06 | M81695 | ITGAX | integrin, alpha X (antigen CD11C (p150), alpha polypeptide) |
| 5.92 | NM_003494 | DYSF | dysferlin, limb girdle muscular dystrophy 2B (autosomal recessive) |
| 5.85 | AI860212 | PAG1 | phosphoprotein associated with glycosphingolipid microdomains 1 |
| 5.75 | NM_013447 | EMR2 | egf-like module containing, mucin-like, hormone receptor-like 2 |
| 5.62 | NM_017806 | LIME1 | Lck interacting transmembrane adaptor 1 |
| 5.62 | AK092824 | AMN | Amnionless homolog (mouse) |
| 5.59 | AF345567 | GPR174 | G protein-coupled receptor 174 |
| 5.26 | L03419 | FCGR1A; LOC440607 | Fc fragment of IgG, high affinity Ia, receptor (CD64); Fc-gamma receptor I B2 |
| 5.24 | BG230586 | SLC7A6 | solute carrier family 7 (cationic amino acid transporter, y+ system), member 6 |
| 5.18 | AF015524 | CCRL2 | chemokine (C-C motif) receptor-like 2 |
| 5.13 | AA631143 | SLC45A3 | solute carrier family 45, member 3 |
| 5.10 | AJ240085 | TRAT1 | T cell receptor associated transmembrane adaptor 1 |
| 5.05 | AW183080 | GPR92 | G protein-coupled receptor 92 |
| 5.03 | NM_002120 | HLA-DOB | major histocompatibility complex, class II, DO beta |
| 5.03 | NM_015364 | LY96 | lymphocyte antigen 96 |
| 4.90 | NM_020399 | GOPC | golgi associated PDZ and coiled-coil motif containing |
| 4.88 | AK026133 | SEMA4B | sema domain, immunoglobulin domain (Ig), transmembrane domain (TM) and short cytoplasmic domain, (semaphorin) 4B |
| 4.88 | BC041664 | VMD2 | vitelliform macular dystrophy 2 (Best disease, bestrophin) |
| 4.85 | NM_152592 | C14orf49 | chromosome 14 open reading frame 49 |
| 4.85 | AA923524 | RASGRP4 | RAS guanyl releasing protein 4 |
| 4.85 | BC008777 | ITGAL | integrin, alpha L (antigen CD11A (p180) |
| 4.67 | AF014403 | PPAP2A | phosphatidic acid phosphatase type 2A |
| 4.65 | AK097698 | SORCS2 | Sortilin-related VPS10 domain containing receptor 2 |
| 4.63 | X14355 | FCGR1A | Fc fragment of IgG, high affinity Ia, receptor (CD64) |
| 4.55 | NM_001629 | ALOX5AP | arachidonate 5-lipoxygenase-activating protein |
| 4.50 | AU155968 | C18orf1 | chromosome 18 open reading frame 1 |
| 4.44 | AK075092 | HERV-FRD | HERV-FRD provirus ancestral Env polyprotein |
| 4.42 | NM_020960 | GPR107 | G protein-coupled receptor 107 |
| 4.37 | BC000039 | FAM26B | family with sequence similarity 26, member B |
| 4.35 | NM_153701 | IL12RB1 | interleukin 12 receptor, beta 1 |
| 4.35 | AI762344 | PTGER1 | prostaglandin E receptor 1 (subtype EP1), 42 kDa |
| 4.31 | NM_006459 | SPFH1 | SPFH domain family, member 1 |
| 4.27 | NM_003126 | SPTA1 | spectrin, alpha, erythrocytic 1 (elliptocytosis 2) |
| 4.22 | AL518391 | AQP1 | aquaporin 1 (channel-forming integral protein, 28 kDa) |
| 4.12 | AK026188 | PCDHGC3 | protocadherin gamma subfamily C |
| 4.10 | AU146685 | EDG2 | Endothelial differentiation, lysophosphatidic acid G-protein-coupled receptor, 2 |
| 4.05 | BE673587 | SLC14A1 | Solute carrier family 14 (urea transporter), member 1 (Kidd blood group) |
| 4.02 | BF129969 | TSPAN2 | tetraspanin 2 |
| 4.00 | AW243272 | KCNK5 | Potassium channel, subfamily K, member 5 |
| 3.98 | T68858 | DHRS3 | Dehydrogenase/reductase (SDR family) member 3 |
| 3.94 | AI827849 | VTI1A | Vesicle transport through interaction with t-SNAREs homolog 1A (yeast) |
| 3.86 | AL134012 | NRXN2 | Neurexin 2 |
| 3.83 | BG230614 | CD47 | CD47 antigen (Rh-related antigen, integrin-associated signal transducer) |
| 3.80 | AI869717 | MGC15523 | hypothetical protein MGC15523 |
| 3.80 | AI458583 | SIMP | Source of immunodominant MHC-associated peptides |
| 3.79 | NM_002183 | IL3RA | interleukin 3 receptor, alpha (low affinity) |
| 3.79 | AA608820 | NRXN2 | neurexin 2 |
| 3.73 | NM_000206 | IL2RG | interleukin 2 receptor, gamma (severe combined immunodeficiency) |
| 3.72 | BC002737 | VAMP2 | vesicle-associated membrane protein 2 (synaptobrevin 2) |
| 3.72 | BC005884 | BID | BH3 interacting domain death agonist; BH3 interacting domain death agonist |

TABLE 3-continued

| Fold Change | Genbank | Gene Symbol | Description |
|---|---|---|---|
| 3.68 | AI688418 | PLXNA2 | plexin A2 |
| 3.68 | BC003105 | PTP4A3 | protein tyrosine phosphatase type IVA, member 3 |
| 3.68 | NM_001772 | CD33 | CD33 antigen (gp67) |
| 3.66 | AI955119 | VAMP2 | vesicle-associated membrane protein 2 (synaptobrevin 2) |
| 3.65 | BC007524 | SPAG9 | sperm associated antigen 9 |
| 3.64 | AI344200 | SLC25A35 | solute carrier family 25, member 35 |
| 3.64 | BC005253 | KLHL20 | kelch-like 20 (Drosophila) |
| 3.58 | BF381837 | C20orf52 | chromosome 20 open reading frame 52 |
| 3.51 | NM_002886 | RAP2A; RAP2B | RAP2A, member of RAS oncogene family; RAP2B, member of RAS oncogene family |
| 3.50 | NM_007063 | TBC1D8 | TBC1 domain family, member 8 (with GRAM domain) |
| 3.45 | AK027160 | BCL2L11 | BCL2-like 11 (apoptosis facilitator) |
| 3.44 | BF055366 | EDG2 | endothelial differentiation, lysophosphatidic acid G-protein-coupled receptor, 2 |
| 3.42 | NM_003608 | GPR65 | G protein-coupled receptor 65 |
| 3.41 | AI675453 | PLXNA3 | plexin A3 |
| 3.40 | AV734194 | DPP8 | dipeptidylpeptidase 8 |
| 3.36 | BC001956 | KIAA1961 | KIAA1961 gene |
| 3.34 | NM_013332 | HIG2 | hypoxia-inducible protein 2 |
| 3.31 | BC029450 | SLC33A1 | Solute carrier family 33 (acetyl-CoA transporter), member 1 |
| 3.28 | BF677986 | KIAA1961 | KIAA1961 gene |
| 3.27 | AI433691 | CACNA2D4 | calcium channel, voltage-dependent, alpha 2/delta subunit 4 |
| 3.26 | AB014573 | NPHP4 | nephronophthisis 4 |
| 3.25 | AL582804 | LY9 | lymphocyte antigen 9 |
| 3.25 | BG236280 | CD86 | CD86 antigen (CD28 antigen ligand 2, B7-2 antigen) |
| 3.24 | AA639289 | SLC26A7 | Solute carrier family 26, member 7 |
| 3.24 | NM_005211 | CSF1R | colony stimulating factor 1 receptor, formerly McDonough feline sarcoma viral (v-fms) oncogene homolog; colony stimulating factor 1 receptor, formerly McDonough feline sarcoma viral (v-fms) oncogene homolog |
| 3.24 | AI051254 | TRPM2 | transient receptor potential cation channel, subfamily M, member 2 |
| 3.23 | AW292816 | ABHD2 | abhydrolase domain containing 2 |
| 3.23 | BC040275 | RASGRF1 | Ras protein-specific guanine nucleotide-releasing factor 1 |
| 3.22 | NM_021911 | GABRB2 | gamma-aminobutyric acid (GABA) A receptor, beta 2 |
| 3.19 | AI660619 | SLC7A6 | solute carrier family 7 (cationic amino acid transporter, y+ system), member 6 |
| 3.19 | NM_001860 | SLC31A2 | solute carrier family 31 (copper transporters), member 2 |
| 3.18 | NM_015680 | C2orf24 | chromosome 2 open reading frame 24 |
| 3.17 | AW058600 | SLC36A1 | solute carrier family 36 (proton/amino acid symporter), member 1 |
| 3.16 | AU145049 | HIP1 | Huntingtin interacting protein 1 |
| 3.15 | NM_005770 | SERF2 | small EDRK-rich factor 2 |
| 3.15 | NM_003566 | EEA1 | Early endosome antigen 1, 162 kD |
| 3.14 | NM_020041 | SLC2A9 | solute carrier family 2 (facilitated glucose transporter), member 9 |
| 3.14 | W90718 | SLC24A4 | solute carrier family 24 (sodium/potassium/calcium exchanger), member 4 |
| 3.13 | AI423165 | TICAM2 | toll-like receptor adaptor molecule 2 |
| 3.12 | AI674647 | SPPL2A | signal peptide peptidase-like 2A |
| 3.11 | NM_004121 | GGTLA1 | gamma-glutamyltransferase-like activity 1 |
| 3.10 | NM_004546 | NDUFB2 | NADH dehydrogenase (ubiquinone) 1 beta subcomplex, 2, 8 kDa |
| 3.05 | X15786 | RET | ret proto-oncogene (multiple endocrine neoplasia and medullary thyroid carcinoma 1, Hirschsprung disease) |
| 3.05 | AF181660 | MPZL1 | myelin protein zero-like 1 |
| 3.00 | AI571996 | STAM2 | signal transducing adaptor molecule (SH3 domain and ITAM motif) 2 |
| 2.99 | NM_000201 | ICAM1 | intercellular adhesion molecule 1 (CD54), human rhinovirus receptor |
| 2.93 | NM_025244 | TSGA10 | testis specific, 10 |
| 2.93 | AU147538 | PRKCE | Protein kinase C, epsilon |
| 2.92 | NM_024576 | OGFRL1 | opioid growth factor receptor-like 1 |
| 2.91 | AI248055 | ABCC4 | ATP-binding cassette, sub-family C (CFTR/MRP), member 4 |
| 2.86 | AA503877 | CEPT1 | Choline/ethanolamine phosphotransferase 1 |
| 2.84 | BC030993 | FLJ21127 | Hypothetical protein FLJ21127 |

TABLE 3-continued

| Fold Change | Genbank | Gene Symbol | Description |
|---|---|---|---|
| 2.82 | NM_001859 | SLC31A1 | solute carrier family 31 (copper transporters), member 1 |
| 2.81 | M74721 | CD79A | CD79A antigen (immunoglobulin-associated alpha) |
| 2.79 | AI986112 | MGAT4B | Mannosyl (alpha-1,3-)-glycoprotein beta-1,4-N-acetylglucosaminyltransferase, isoenzyme B |
| 2.79 | NM_030930 | UNC93B1 | unc-93 homolog B1 (*C. elegans*); unc-93 homolog B1 (*C. elegans*) |
| 2.79 | X74039 | PLAUR | plasminogen activator, urokinase receptor |
| 2.75 | BC005253 | KLHL20 | kelch-like 20 (*Drosophila*) |
| 2.73 | AB036432 | AGER | advanced glycosylation end product-specific receptor |
| 2.71 | NM_007245 | ATXN2L | ataxin 2-like |
| 2.71 | NM_016072 | GOLT1B | golgi transport 1 homolog B (*S. cerevisiae*) |
| 2.71 | AI453548 | ZDHHC8 | zinc finger, DHHC-type containing 8 |
| 2.70 | AI636233 | TMEM8 | transmembrane protein 8 (five membrane-spanning domains) |
| 2.69 | BE502509 | T3JAM | TRAF3 interacting protein 3 |
| 2.69 | AW117765 | PEX13 | peroxisome biogenesis factor 13 |
| 2.69 | AW052216 | IL17RB | Interleukin 17 receptor B |
| 2.67 | NM_003853 | IL18RAP | interleukin 18 receptor accessory protein |
| 2.66 | NM_002490 | NDUFA6 | NADH dehydrogenase (ubiquinone) 1 alpha subcomplex, 6, 14 kDa |
| 2.65 | NM_016639 | TNFRSF12A | tumor necrosis factor receptor superfamily, member 12A |
| 2.65 | AI363185 | FLJ20255 | Hypothetical protein FLJ20255 |
| 2.65 | NM_052931 | SLAMF6 | SLAM family member 6 |
| 2.65 | AW571669 | TNFRSF19L | tumor necrosis factor receptor superfamily, member 19-like |
| 2.64 | AA654142 | CEECAM1 | cerebral endothelial cell adhesion molecule 1 |
| 2.62 | AW510783 | TMEM63A | transmembrane protein 63A |
| 2.61 | W95007 | ACSL4 | Acyl-CoA synthetase long-chain family member 4 |
| 2.60 | S76475 | NTRK3 | neurotrophic tyrosine kinase, receptor, type 3 |
| 2.60 | AJ130713 | SIGLEC7 | sialic acid binding Ig-like lectin 7 |
| 2.56 | NM_003775 | EDG6 | endothelial differentiation, G-protein-coupled receptor 6 |
| 2.55 | AI978986 | MAMDC4 | MAM domain containing 4 |
| 2.54 | AF010447 | MR1 | major histocompatibility complex, class I-related |
| 2.54 | NM_006068 | TLR6 | toll-like receptor 6 |
| 2.53 | AF041811 | NTRK3 | neurotrophic tyrosine kinase, receptor, type 3 |
| 2.53 | AW953521 | SERF2; HYPK | small EDRK-rich factor 2; Huntingtin interacting protein K |
| 2.51 | AW293276 | CD53 | CD53 antigen |
| 2.49 | AK023058 | PLXNA2 | Plexin A2 |
| 2.49 | AI125204 | C6orf128 | chromosome 6 open reading frame 128 |
| 2.49 | NM_000392 | ABCC2 | ATP-binding cassette, sub-family C (CFTR/MRP), member 2 |
| 2.46 | BC032474 | TIRAP | toll-interleukin 1 receptor (TIR) domain containing adaptor protein |
| 2.44 | NM_031211 | IMAA; LOC388221; LOC440345; LOC440354; LOC595101; LOC641298 | SLC7A5 pseudogene; SLC7A5 pseudogene; NPIP-like locus; NPIP-like locus; hypothetical protein LOC440345; hypothetical protein LOC440345; PI-3-kinase-related kinase SMG-1 pseudogene; PI-3-kinase-related kinase SMG-1 pseudogene; PI-3-kinase-related kinase SMG-1 pseudogene; PI-3-kinase-related kinase SMG-1 pseudogene; PI-3-kinase-related kinase SMG-1 - like locus; PI-3-kinase-related kinase SMG-1 - like locus |
| 2.44 | AI797836 | CD5 | CD5 antigen (p56-62) |
| 2.41 | W72082 | C1QR1 | complement component 1, q subcomponent, receptor 1; complement component 1, q subcomponent, receptor 1 |
| 2.40 | AA708616 | DPP9 | dipeptidylpeptidase 9 |
| 2.40 | BM987094 | DLGAP4 | discs, large (*Drosophila*) homolog-associated protein 4 |
| 2.40 | AL713719 | LOC283501 | ATPase, Class VI, type 11A |
| 2.39 | AI628734 | PRLR | prolactin receptor |
| 2.39 | NM_012110 | CHIC2 | cysteine-rich hydrophobic domain 2 |
| 2.38 | AK022002 | TFR2 | transferrin receptor 2 |
| 2.37 | NM_001555 | IGSF1 | immunoglobulin superfamily, member 1 |
| 2.36 | AA426091 | C19orf15 | chromosome 19 open reading frame 15 |
| 2.36 | BE547542 | GOPC | golgi associated PDZ and coiled-coil motif containing |
| 2.36 | NM_004231 | ATP6V1F | ATPase, H+ transporting, lysosomal 14 kDa, V1 subunit F |
| 2.36 | AJ130712 | SIGLEC7 | sialic acid binding Ig-like lectin 7 |
| 2.36 | NM_017905 | TMCO3 | transmembrane and coiled-coil domains 3 |

TABLE 3-continued

| Fold Change | Genbank | Gene Symbol | Description |
|---|---|---|---|
| 2.35 | AB054985 | CACNB1 | calcium channel, voltage-dependent, beta 1 subunit |
| 2.35 | NM_005003 | NDUFAB1 | NADH dehydrogenase (ubiquinone) 1, alpha/beta subcomplex, 1, 8 kDa |
| 2.35 | NM_001251 | CD68 | CD68 antigen |
| 2.35 | AA700869 | PSCD2 | Pleckstrin homology, Sec7 and coiled-coil domains 2 (cytohesin-2) |
| 2.35 | U94903 | CD44 | CD44 antigen (homing function and Indian blood group system) |
| 2.35 | NM_003841 | TNFRSF10C | tumor necrosis factor receptor superfamily, member 10c, decoy without an intracellular domain |
| 2.33 | NM_004541 | NDUFA1 | NADH dehydrogenase (ubiquinone) 1 alpha subcomplex, 1, 7.5 kDa |
| 2.33 | BE567130 | KLRK1 | Killer cell lectin-like receptor subfamily K, member 1 |
| 2.31 | NM_017460 | CYP3A4 | cytochrome P450, family 3, subfamily A, polypeptide 4 |
| 2.31 | AI339536 | DSC1 | Desmocollin 1 |
| 2.31 | NM_001783 | CD79A | CD79A antigen (immunoglobulin-associated alpha); CD79A antigen (immunoglobulin-associated alpha) |
| 2.30 | AA333161 | VTI1A | vesicle transport through interaction with t-SNAREs homolog 1A (yeast) |
| 2.30 | AW134823 | CD6 | CD6 antigen; CD6 antigen |
| 2.30 | AL137537 | ATP8B2 | ATPase, Class I, type 8B, member 2 |
| 2.29 | AI671983 | SLC2A9 | solute carrier family 2 (facilitated glucose transporter), member 9 |
| 2.29 | AA018187 | C22orf3 | chromosome 22 open reading frame 3 |
| 2.29 | AL117415 | ADAM33 | ADAM metallopeptidase domain 33 |
| 2.29 | NM_002588 | PCDHGC3; PCDHGB4; PCDHGA8; PCDHGA12; PCDHGC5; PCDHGC4; PCDHGB7; PCDHGB6; PCDHGB5; PCDHGB3; PCDHGB2; PCDHGB1; PCDHGA11; PCDHGA10; PCDHGA9; PCDHGA7; PCDHGA6; PCDHGA5; PCDHGA4; PCDHGA3; PCDHGA2; PCDHGA1 | protocadherin gamma subfamily C, 3; protocadherin gamma subfamily B, 4; protocadherin gamma subfamily A, 8; protocadherin gamma subfamily A, 12; protocadherin gamma subfamily C, 5; protocadherin gamma subfamily C, 4; protocadherin gamma subfamily B, 7; protocadherin gamma subfamily B, 6; protocadherin gamma subfamily B, 5; protocadherin gamma subfamily B, 3; protocadherin gamma subfamily B, 2; protocadherin gamma subfamily B, 1; protocadherin gamma subfamily A, 11; protocadherin gamma subfamily A, 10; protocadherin gamma subfamily A, 9; protocadherin gamma subfamily A, 7; protocadherin gamma subfamily A, 6; protocadherin gamma subfamily A, 5; protocadherin gamma subfamily A, 4; protocadherin gamma subfamily A, 3; protocadherin gamma subfamily A, 2; protocadherin gamma subfamily A, 1 |
| 2.29 | NM_020960 | GPR107 | G protein-coupled receptor 107 |
| 2.29 | AK074635 | GENX-3414 | Genethonin 1 |
| 2.29 | BE138575 | ITGB5 | Integrin, beta 5 |
| 2.28 | NM_003830 | SIGLEC5 | sialic acid binding Ig-like lectin 5; sialic acid binding Ig-like lectin 5 |
| 2.28 | NM013319 | UBIAD1 | UbiA prenyltransferase domain containing 1 |
| 2.28 | M63889 | FGFR1 | fibroblast growth factor receptor 1 (fms-related tyrosine kinase 2, Pfeiffer syndrome) |
| 2.27 | H67156 | MSCP | Solute carrier family 25, member 37 |
| 2.27 | BC006215 | SMEK2 | KIAA1387 protein; KIAA1387 protein |
| 2.27 | AL109653 | SLITRK2 | SLIT and NTRK-like family, member 2 |
| 2.27 | NM_007011 | ABHD2 | abhydrolase domain containing 2 |
| 2.26 | AI767210 | MGC11332 | Hypothetical protein MGC11332 |
| 2.26 | BF723605 | NRCAM | Neuronal cell adhesion molecule |
| 2.26 | R08129 | CDA08 | T-cell immunomodulatory protein |
| 2.26 | AF052059 | SEL1L | sel-1 suppressor of lin-12-like (*C. elegans*) |
| 2.26 | NM_005729 | PPIF | peptidylprolyl isomerase F (cyclophilin F) |
| 2.25 | BE858032 | ARL2L1 | ADP-ribosylation factor-like 2-like 1 |
| 2.25 | AI950390 | C14orf118 | Chromosome 14 open reading frame 118 |
| 2.24 | NM_017767 | SLC39A4 | solute carrier family 39 (zinc transporter), member 4 |
| 2.24 | AL110273 | SPTAN1 | Spectrin, alpha, non-erythrocytic 1 (alpha-fodrin) |
| 2.24 | AI077660 | CDA08 | T-cell immunomodulatory protein |
| 2.23 | AA488687 | SLC7A11 | solute carrier family 7, (cationic amino acid transporter, y+ system) member 11 |
| 2.23 | NM_000634 | IL8RA | interleukin 8 receptor, alpha |
| 2.22 | AL390177 | MGC34032 | Solute carrier family 44, member 5 |

TABLE 3-continued

| Fold Change | Genbank | Gene Symbol | Description |
|---|---|---|---|
| 2.21 | NM_001531 | MR1 | major histocompatibility complex, class I-related |
| 2.21 | NM_003183 | ADAM17 | ADAM metallopeptidase domain 17 (tumor necrosis factor, alpha, converting enzyme) |
| 2.20 | AC003999 | SCAP2 | src family associated phosphoprotein 2 |
| 2.20 | BC014416 | SLC33A1 | solute carrier family 33 (acetyl-CoA transporter), member 1 |
| 2.20 | AF226731 | ADORA3 | adenosine A3 receptor |
| 2.19 | AI608725 | ICAM1 | intercellular adhesion molecule 1 (CD54), human rhinovirus receptor |
| 2.19 | U41163 | SLC6A8; FLJ43855 | solute carrier family 6 (neurotransmitter transporter, creatine), member 8; similar to sodium- and chloride-dependent creatine transporter |
| 2.19 | AU147799 | LRRC15 | leucine rich repeat containing 15 |
| 2.18 | AW337166 | LOC255104 | Transmembrane and coiled-coil domains 4 |
| 2.18 | NM_006505 | PVR | poliovirus receptor |
| 2.18 | AI638420 | CLIC4 | chloride intracellular channel 4 |
| 2.18 | AI167482 | SCUBE3 | Signal peptide, CUB domain, EGF-like 3 |
| 2.18 | AI739514 | HAS3 | hyaluronan synthase 3 |
| 2.18 | NM_005971 | FXYD3 | FXYD domain containing ion transport regulator 3 |
| 2.17 | AL022398 | TRAF3IP3 | TRAF3 interacting protein 3 |
| 2.17 | U90940 | FCGR2C | Fc fragment of IgG, low affinity IIc, receptor for (CD32) |
| 2.16 | BC023540 | SORCS1 | Sortilin-related VPS10 domain containing receptor 1 |
| 2.16 | AV713913 | OSTM1 | osteopetrosis associated transmembrane protein 1 |
| 2.15 | NM_024505 | NOX5 | NADPH oxidase, EF-hand calcium binding domain 5 |
| 2.15 | BC006178 | SEC22L3 | SEC22 vesicle trafficking protein-like 3 (*S. cerevisiae*); SEC22 vesicle trafficking protein-like 3 (*S. cerevisiae*) |
| 2.15 | BG151527 | GRIK5 | glutamate receptor, ionotropic, kainate 5 |
| 2.14 | AW001754 | NEGR1 | neuronal growth regulator 1 |
| 2.14 | NM_013979 | BNIP1 | BCL2/adenovirus E1B 19 kDa interacting protein 1 |
| 2.14 | NM_018643 | TREM1 | triggering receptor expressed on myeloid cells 1 |
| 2.12 | NM_005284 | GPR6 | G protein-coupled receptor 6 |
| 2.11 | AA454190 | ZDHHC20 | zinc finger, DHHC-type containing 20 |
| 2.11 | AB048796 | TMPRSS13 | transmembrane protease, serine 13 |
| 2.11 | AL044520 | NYD-SP21 | testes development-related NYD-SP21 |
| 2.11 | BE463930 | TMAP1 | Matrix-remodelling associated 7 |
| 2.10 | NM_152264 | SLC39A13 | solute carrier family 39 (zinc transporter), member 13 |
| 2.08 | AL530874 | EPHB2 | EPH receptor B2 |
| 2.07 | NM_018668 | VPS33B | vacuolar protein sorting 33B (yeast) |
| 2.07 | NM_024531 | GPR172A | G protein-coupled receptor 172A |
| 2.07 | NM_023038 | ADAM19 | ADAM metallopeptidase domain 19 (meltrin beta) |
| 2.07 | BC001281 | TNFRSF10B | tumor necrosis factor receptor superfamily, member 10b |
| 2.07 | AF217749 | PCDHB9 | protocadherin beta 9 |
| 2.06 | AB030077 | FGFR2 | fibroblast growth factor receptor 2 (bacteria-expressed kinase, keratinocyte growth factor receptor, craniofacial dysostosis 1, Crouzon syndrome, Pfeiffer syndrome, Jackson-Weiss syndrome) |
| 2.06 | AL137432 | SUSD1 | sushi domain containing 1 |
| 2.05 | NM_004518 | KCNQ2 | potassium voltage-gated channel, KQT-like subfamily, member 2 |
| 2.04 | AI672363 | VPS33B | vacuolar protein sorting 33B (yeast) |
| 2.04 | NM_006671 | SLC1A7 | solute carrier family 1 (glutamate transporter), member 7 |
| 2.03 | AA215519 | DLGAP1 | Discs, large (*Drosophila*) homolog-associated protein 1 |
| 2.02 | NM_004648 | PTPNS1 | protein tyrosine phosphatase, non-receptor type substrate 1 |
| 2.02 | NM_002564 | P2RY2 | purinergic receptor P2Y, G-protein coupled, 2 |
| 2.01 | BF511678 | SCUBE3 | Signal peptide, CUB domain, EGF-like 3 |
| 2.01 | BC013385 | CLEC7A | C-type lectin domain family 7, member A |

CD47 Facilitates Engraftment, Inhibits Phagocytosis, and is More Highly Expressed on AML LSC. It has long been recognized that the innate immune system, through natural killer (NK) effector cells, functions in the elimination of non-self and aberrant cells. NK cells eliminate target cells recognized by a variety of NK cell-activating receptors that bind ligands present on many normal cells; however, expression of self major histocompatibility complex (MHC) class I molecules can protect a cell by binding to NK inhibitory receptors.

These inhibitory receptors often contain immunoreceptor tyrosine-based inhibitory (ITIM) motifs that recruit and activate the SHP-1 and SHP-2 tyrosine phosphatases, which in turn inhibit signal transduction from the activating receptors. Accumulating evidence indicates that monocyte-derived effector cells, such as macrophages and dendritic cells, are also involved in the elimination of non-self and aberrant cells, mediated by a number of activating receptors. These effector cells also express the inhibitory receptor, signal regulatory protein alpha (SIRPα), which contains an ITIM motif able to recruit and activate the SHP-1 and SHP-2 phosphatases resulting in inhibition of phagocytosis. Several studies have identified CD47 as the ligand for SIRPα. CD47 is a widely expressed transmembrane protein, originally identified as integrin associated protein (IAP) due to its physical association with several integrins.

CD47 has been implicated in a number of processes including platelet activation, cell motility and adhesion, and leukocyte adhesion, migration, and phagocytosis. The CD47-SIRPα interaction has been implicated in the inhibition of phagocytosis from a number of studies. First, CD47-deficient, but not wild type, mouse red blood cells (RBCs) were rapidly cleared from the bloodstream by splenic macrophages when transfused into wild type mice, and this effect was dependent on the CD47-SIRPα interaction. CD47-deficient, but not wild type, lymphocytes and bone marrow cells were also rapidly cleared upon transplantation into congenic wild type recipients through macrophage and dendritic cell-mediated phagocytosis. Additional evidence suggested that the CD47-SIRPα interaction can inhibit phagocytosis stimulated by the recognition of IgG or complement opsonized cells. Thus, CD47 functions as a critical regulator of macrophage and dendritic cell phagocytosis by binding to SIRPα and delivering a dominant inhibitory signal.

We determined expression of CD47 on human AML LSC and normal HSC by flow cytometry. HSC (Lin–CD34+CD38–CD90+) from three samples of normal human mobilized peripheral blood and AML LSC (Lin+CD34+CD38–CD90–) from seven samples of human AML were analyzed for surface expression of CD47 (FIG. 2). CD47 was expressed at low levels on the surface of normal HSC; however, on average, it was approximately 5-fold more highly expressed on AML LSC, as well as bulk leukemic blasts.

Anti-Human CD47 Monoclonal Antibody Stimulates Phagocytosis and Inhibits Engraftment of AML LSC. In order to test the model that CD47 overexpression on AML LSC prevents phagocytosis of these cells through its interaction with SIRPα on effector cells, we have utilized a monoclonal antibody directed against CD47 known to disrupt the CD47-SIRPα interaction. The hybridoma producing a mouse-anti-human CD47 monoclonal antibody, termed B6H12, was obtained from ATCC and used to produce purified antibody. First, we conducted in vitro phagocytosis assays. Primary human AML LSC were purified by FACS from two samples of human AML, and then loaded with the fluorescent dye CFSE. These cells were incubated with mouse bone marrow-derived macrophages and monitored using immunofluorescence microscopy (FIG. 2) and flow cytometry (FIG. 3) to identify phagocytosed cells. In both cases, no phagocytosis was observed in the presence of an isotype control antibody; however, significant phagocytosis was detected with the addition of the anti-CD47 antibody. Thus, blockage of human CD47 with a monoclonal antibody is capable of stimulating the phagocytosis of these cells by mouse macrophages.

Figure 5:
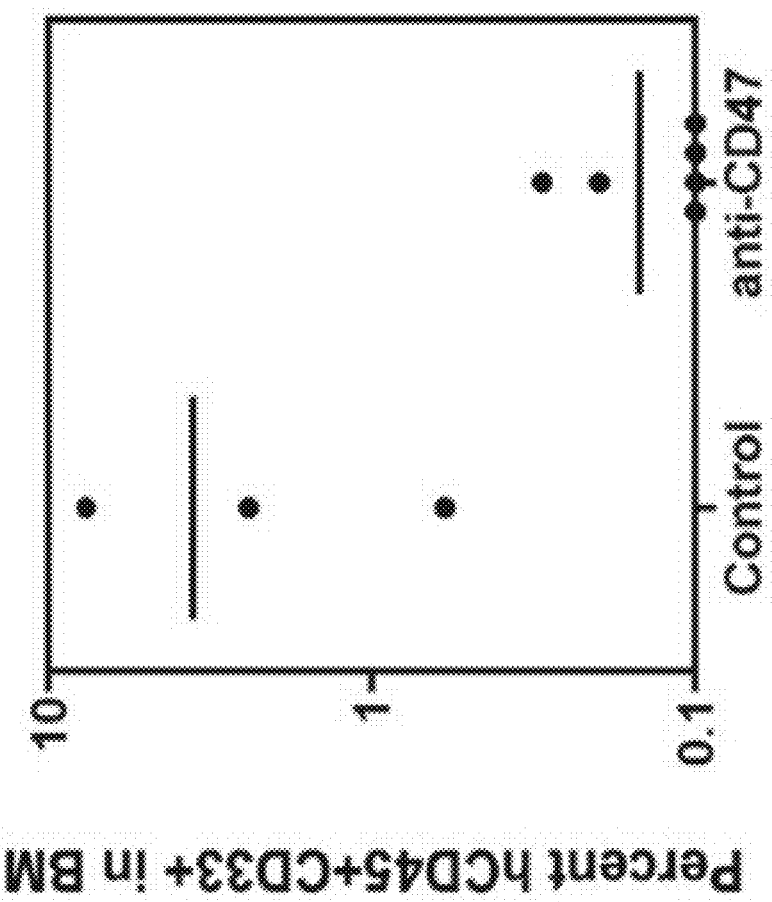
FIG. 5: Anti-CD47 antibody inhibits in vivo engraftment of primary human AML. Two primary human AML samples were untreated (control, n=3) or coated with anti-human CD47 antibody (anti-CD47, n=6) prior to transplantation into newborn NOG mice. 13 weeks later, mice were sacrificed and the bone marrow was analyzed for the presence of human CD45+CD33+ myeloid leukemia cells by flow cytometry.

We next investigated the ability of the anti-CD47 antibody to inhibit AML LSC engraftment in vivo. Two primary human AML samples were either untreated or coated with the anti-CD47 antibody prior to transplantation into NOG newborn mice. 13 weeks later, the mice were sacrificed and analyzed for human leukemia bone marrow engraftment by flow cytometry (FIG. 5). The control mice demonstrated leukemic engraftment while mice transplanted with the anti-CD47-coated cells showed little to no engraftment. These data indicate that blockade of human CD47 with a monoclonal antibody is able to inhibit AML LSC engraftment.

CD96 is a Human Acute Myeloid Leukemia Stem Cell-Specific Cell Surface Molecule. CD96, originally termed Tactile, was first identified as a T cell surface molecule that is highly upregulated upon T cell activation. CD96 is expressed at low levels on resting T and NK cells and is strongly upregulated upon stimulation in both cell types. It is not expressed on other hematopoietic cells, and examination of its expression pattern showed that it is only otherwise present on some intestinal epithelia. The cytoplasmic domain of CD96 contains a putative ITIM motif, but it is not know if this functions in signal transduction. CD96 promotes adhesion of NK cells to target cells expressing CD155, resulting in stimulation of cytotoxicity of activated NK cells.

Preferential Cell Surface Expression of Molecules Identified from Gene Expression Analysis. Beyond CD47 and CD96, several of the molecules listed in FIG. 2B are known to be expressed on AML LSC, including: CD123, CD44, and CD33. The remaining molecules have not been previously reported or identified as preferentially expressed on human AML LSC compared to their normal counterparts. We have examined cell surface expression of two of these molecules by flow cytometry to determine if there is preferential expression on AML LSC compared to normal HSC.

In order to evaluate the other candidate genes in FIG. 1B, we screened this list for those molecules not likely to be expressed on normal HSC based on raw array expression values. Next, using published reports, we investigated the tissue expression pattern of these genes, in order to identify those with very restricted patterns of expression for which monoclonal antibodies would have few targets besides the leukemia cells. Based on these methods, two promising genes were identified: Parathyroid Hormone Receptor 2 and Hepatitis A Virus Cellular Receptor 2 (also known as TIM-3: T cell immunoglobulin mucin 3). Parathyroid Hormone Receptor 2 (PTHR2) is normally expressed in the pancreas and in some areas of the central nervous system. Its primary ligand is a peptide termed tuberoinfundibular peptide 39 (TIP39). Hepatitis A Virus Cellular Receptor 2 (HAVCR2) is normally expressed on a subset of T lymphocytes. Its primary ligand is a molecule named Galectin-9.

Validation of additional sequences utilize specific antibodies and testing by flow cytometry, with comparison to normal multipotent progenitor cells.

EXAMPLE 2

Figures 6A, 6B:
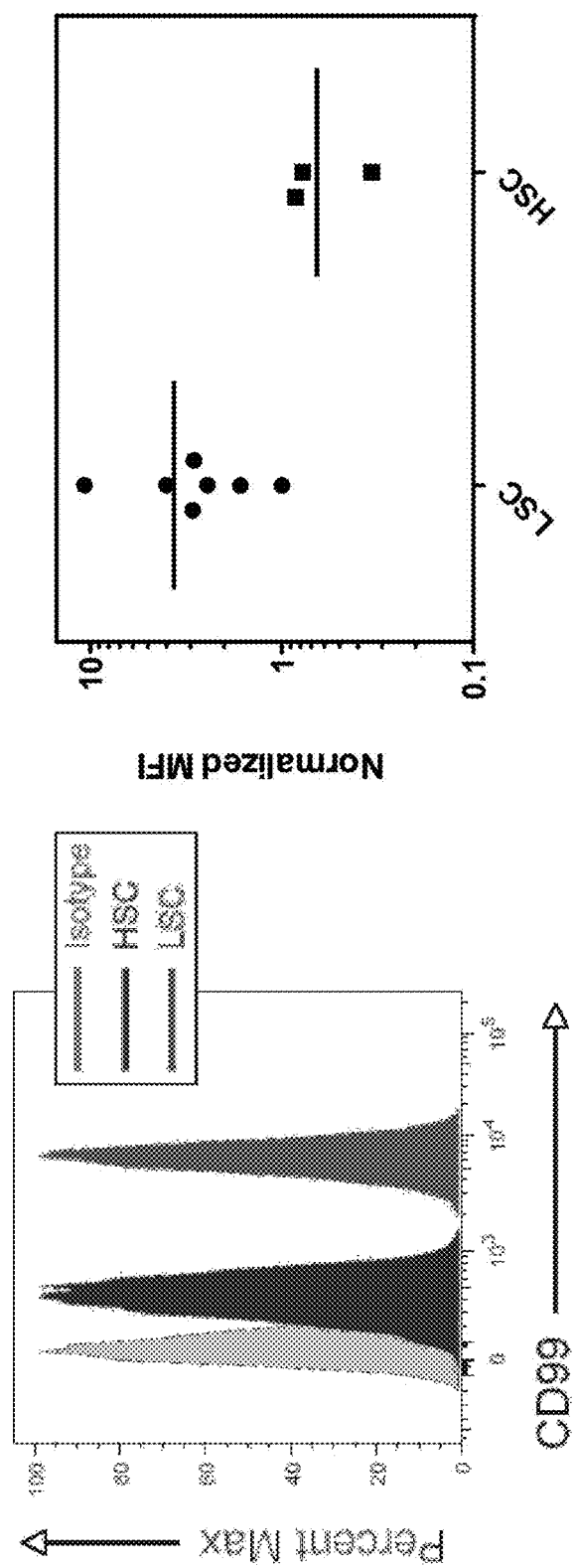
FIG. 6A-6B: CD99 Expression on AML LSC Compared to Normal HSC. CD99 expression was examined on several samples of normal human bone marrow HSC (n=3) and de novo human AML LSC (n=7). Representative histograms of CD99 expression on HSC and LSC (FIG. 6A) and summary of normalized mean fluorescence intensity (MFI) of all specimens (FIG. 6B) are shown. Mean CD99 expression was increased 5.6 fold in AML LSC compared to HSC (p=0.05).
Figure 7A:
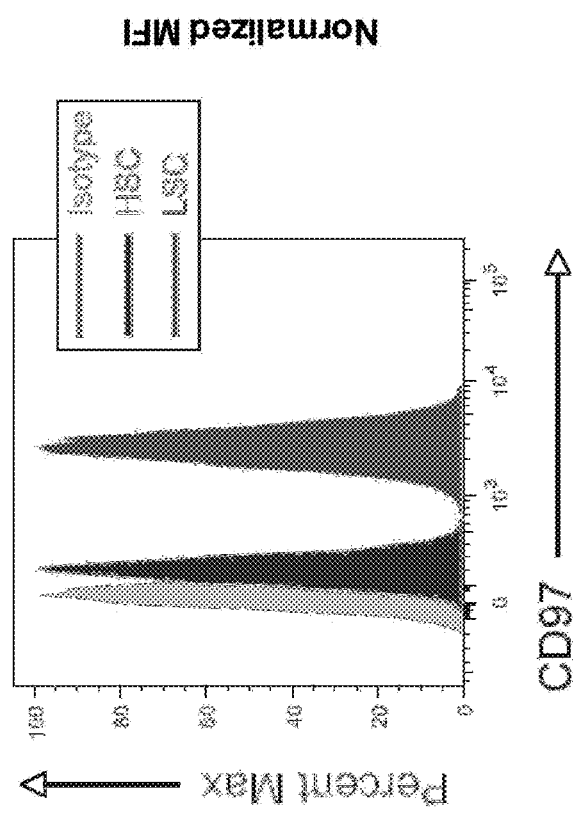
FIG. 7A-7B: CD97 Expression on AML LSC Compared to Normal HSC. CD97 expression was examined on several samples of normal human bone marrow HSC (n=3) and de novo human AML LSC (n=7). Representative histograms of CD97 expression on HSC and LSC (FIG. 7A) and summary of normalized mean fluorescence intensity (MFI) of all specimens (FIG. 7B) are shown. Mean CD97 expression was increased 7.9 fold in AML LSC compared to HSC (p=0.03).
Figure 7B:
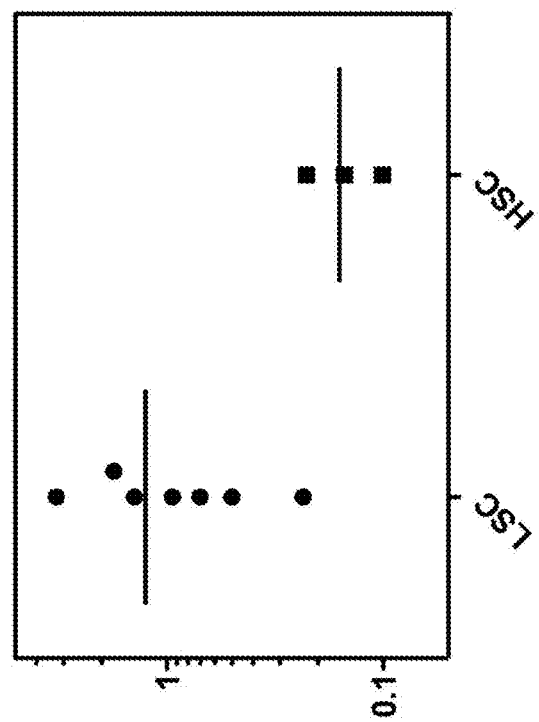

CD99 is a surface glycoprotein with highest expression on T cells where it may function in cellular adhesion. CD99 expression on HSC (Lin–CD34+CD38–CD90+) from three samples of normal human cord blood and AML LSC (Lin–CD34+CD38-CD90–) from seven samples of human AML was determined by flow cytometry (FIG. 6). CD99 was expressed at low levels on the surface of normal HSC; however, on average, it is approximately 5-fold more highly expressed on AML LSC. CD97 is normally expressed on most mature hematopoietic cells and is upregulated on activated lymphocytes where it may function in cellular migration and adhesion. Gene expression profiling indicates low to absent expression of CD97 in HSC and MPP, with approximately 10-fold higher expression in AML LSC. CD97 expression on normal cord blood HSC and AML LSC was examined by flow cytometry and found to be absent on HSC and high on 5 out of 7 AML LSC samples (FIG. 7).

Figures 8A, 8B:
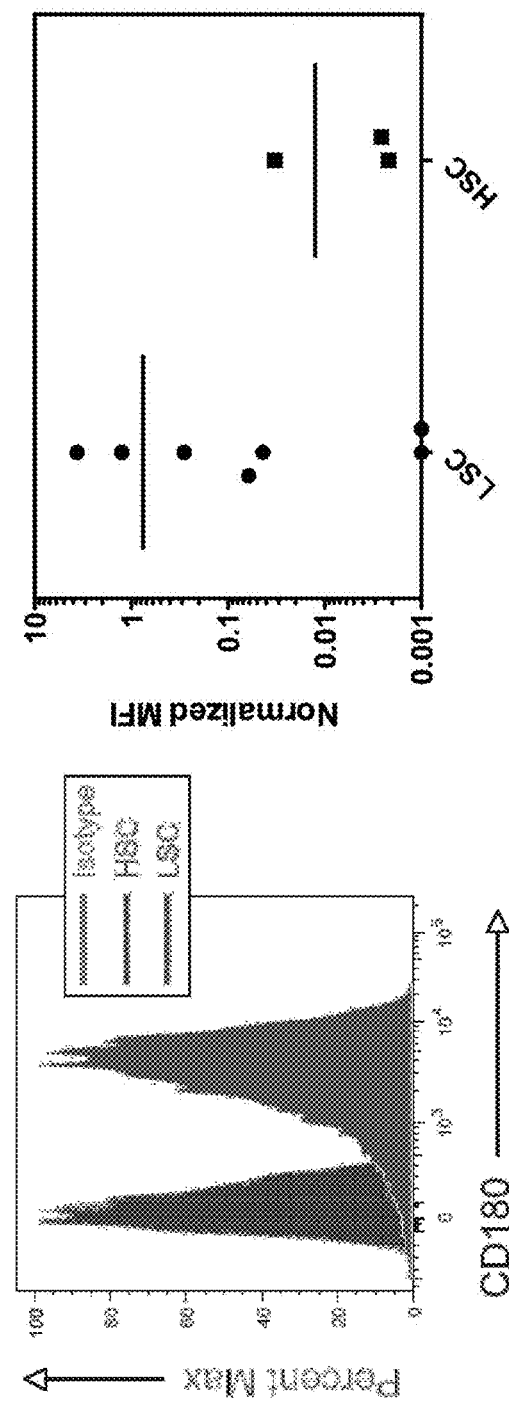
FIG. 8A-8B: CD180 Expression on AML LSC Compared to Normal HSC. CD180 expression was examined on several samples of normal human bone marrow HSC (n=3) and de novo human AML LSC (n=7). Representative histograms of CD180 expression on HSC and LSC (FIG. 8A) and summary of normalized mean fluorescence intensity (MFI) of all specimens (FIG. 8B) are shown. Mean CD180 expression was increased 60 fold in AML LSC compared to HSC (p=0.20).
Figure 9A:
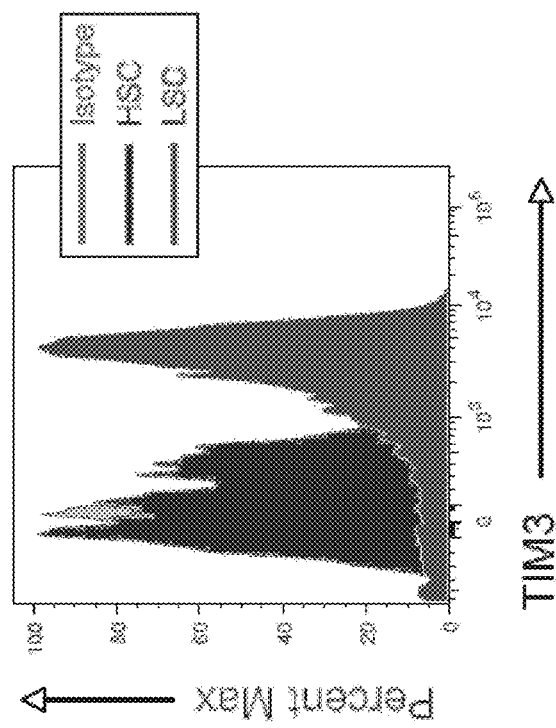
FIG. 9A-9B: TIM3 Expression on AML LSC Compared to Normal HSC. TIM3 expression was examined on several samples of normal human bone marrow HSC (n=3) and de novo human AML LSC (n=14). Representative histograms of TIM3 expression on HSC and LSC (FIG. 9A) and summary of normalized mean fluorescence intensity (MFI) of all specimens (FIG. 9B) are shown. Mean TIM3 expression was increased 9 fold in AML LSC compared to HSC (p=0.01).
Figure 9B:
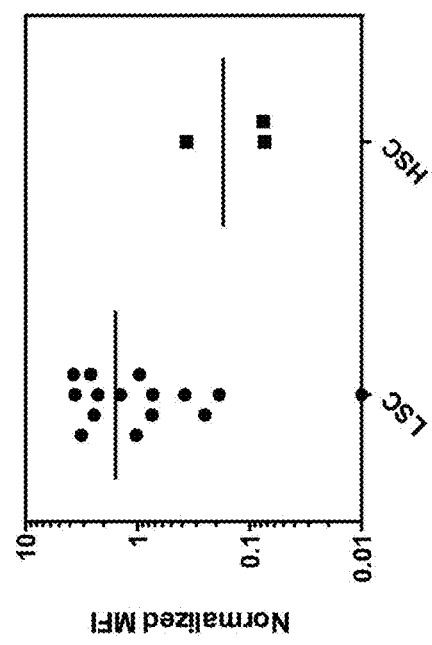
Figure 10:
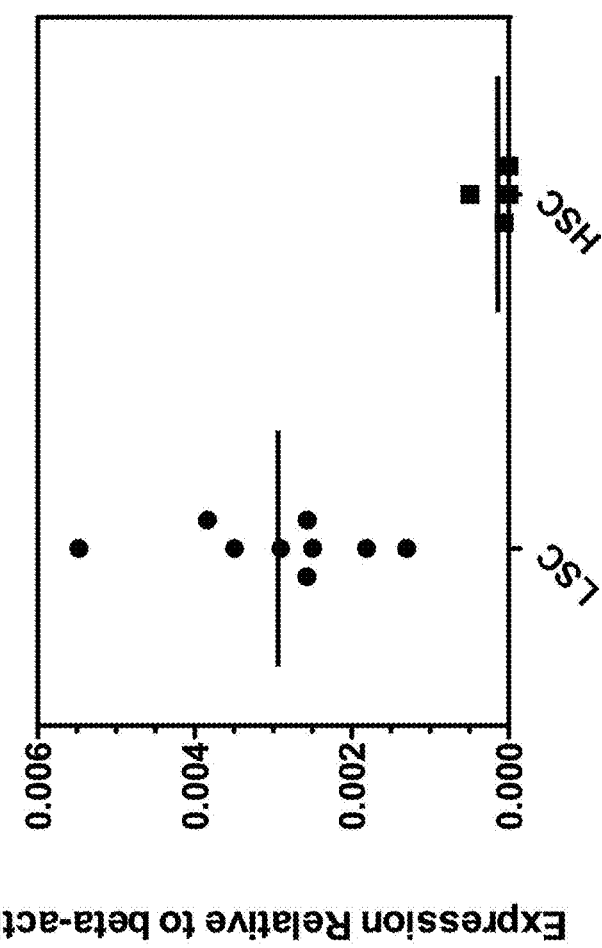
FIG. 10: PTH2R Expression in AML LSC Compared to Normal HSC. PTH2R expression was examined in several samples of normal human bone marrow HSC (n=3) and de novo human AML LSC (n=9). Expression was determined by qRT-PCR and is expressed relative to beta-actin as a control. Mean PTH2R expression was increased 21 fold in AML LSC compared to HSC (p<0.001).

We examined the surface expression of CD97, CD99, CD180, and TIM3 (HAVCR2) on several samples of HSC (from both normal bone marrow and cord blood) and multiple samples of de novo human AML, using flow cytometry. We found increased expression of each of these molecules on AML LSC with low to absent expression on HSC (FIGS. 8-10). We also investigated the expression of PTH2R in bone marrow HSC and AML LSC using quantitative real-time PCR, as no monoclonal antibody validated for flow cytometry is available for this antigen. We found no expression of PTHR2 in HSC with increased expression in AML LSC.

EXAMPLE 3

Prospective Separation of Normal and Leukemic Stem Cells Based on Differential Expression of TIM-3, a Novel Human AML Stem Cell Marker Hematopoietic tissues in acute myeloid leukemia (AML) patients contain both leukemia stem cells (LSC) and residual normal hematopoietic stem cells (HSC). The ability to prospectively separate residual HSC from LSC facilitates scientific and clinical investigation, including purging for autologous hematopoietic cell transplants. We report here the identification of TIM-3 as a novel AML stem cell surface marker that is highly expressed on multiple specimens of AML LSC, but not on normal bone marrow HSC. TIM-3 expression was detected in all cytogenetic subgroups of AML, but was significantly higher in AML-associated with core binding factor translocations or mutations in CEBPA. By assessing engraftment in NOD/SCID/IL2Rγ-null mice, we determined that normal bone marrow HSC do not express TIM-3, whereas LSC from multiple AML specimens express high levels of TIM-3. Finally, TIM-3 expression enabled the prospective separation of HSC from LSC in multiple primary human AML samples.

Cell surface proteins preferentially expressed on AML LSC compared to normal HSC, include CD123, CD44, CLL-1, CD96, and CD47. Such antigens have important clinical applications including: targeting with therapeutic monoclonal antibodies, monitoring of minimal residual disease by flow cytometry, and prospective separation of LSC and HSC. Monoclonal antibodies targeting several of these antigens have shown promise in pre-clinical models and are in active clinical developmen. Increased expression of CLL-1 within the Lin-CD34+CD38- compartment predicted relapse in two AML patients in remission, suggesting a role for LSC surface markers in monitoring minimal residual disease. Thus far, prospective separation of LSC from HSC has only been reported for a single patient on the basis of differential expression of CD47.

Here we report the identification of a novel AML stem cell surface marker, T-cell immunoglobulin mucin-3 (TIM-3). TIM-3 is normally expressed on Th1-T cells, dendritic cells, and monocytes. We found that TIM-3 is highly expressed on multiple specimens of AML LSC but not on normal bone marrow HSC. Significantly, differential expression of TIM-3 enabled the prospective separation of LSC from HSC in multiple primary human AML samples.

Results

TIM-3 Is More Highly Expressed on AML LSC Than on Normal Bone Marrow HSC.

Figure 11C:
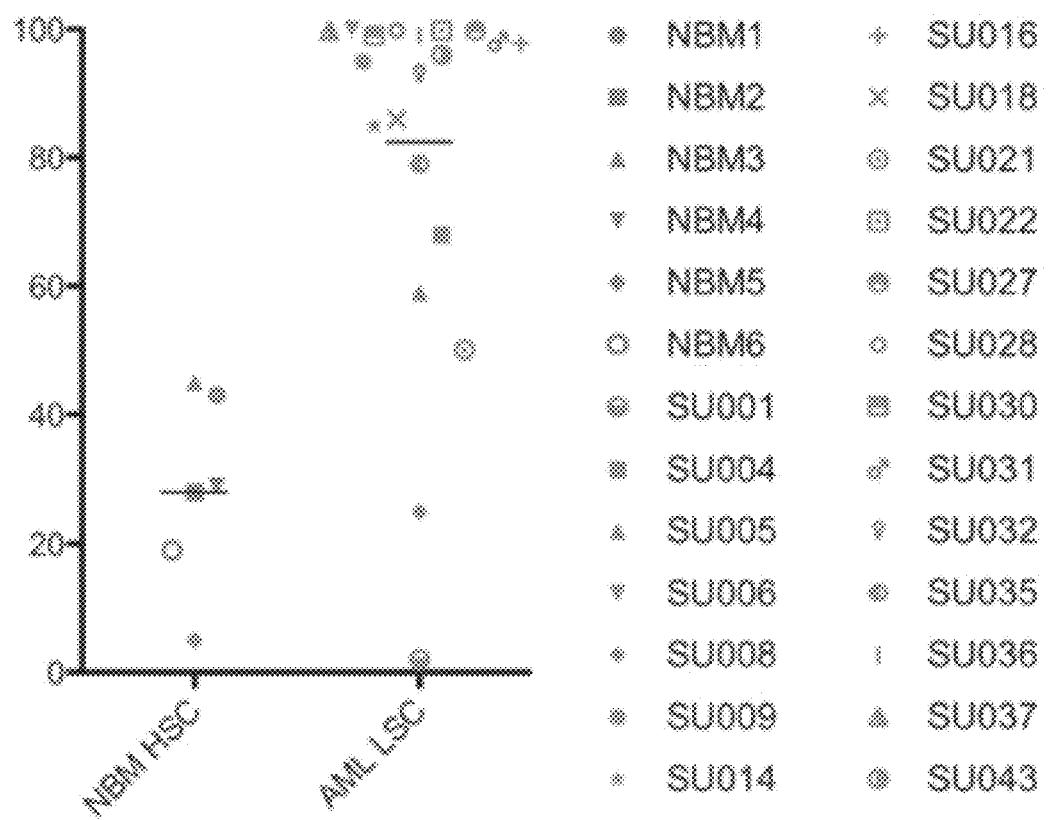
Figure 11D:
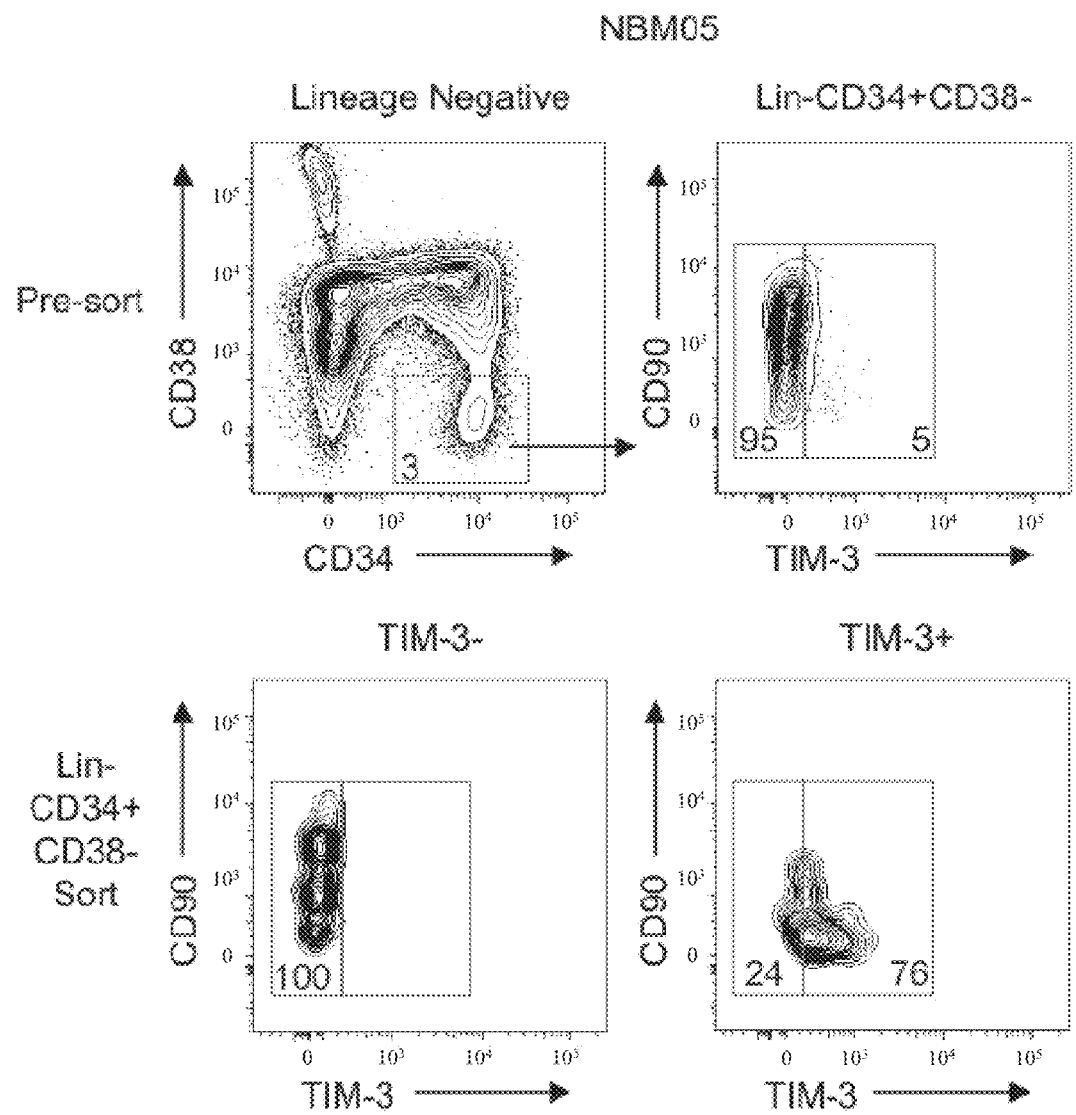

We identified increased expression of TIM-3 in primary human AML LSC compared to normal bone marrow HSC. On this basis, we investigated cell surface expression of TIM-3 protein in AML by flow cytometry. TIM-3 was more highly expressed on multiple specimens of Lin-CD34+CD38- AML LSC compared to normal bone marrow HSC; however, TIM-3 expression was not significantly different between bulk AML cells and the LSC-enriched fraction (FIG. 11A, B). Moreover, a greater percentage of Lin-CD34+CD38- cells expressed TIM-3 in multiple specimens of AML than in normal bone marrow (FIG. 11C). TIM-3 was expressed on 18 out of 20 patient specimens examined, which consisted of diverse clinical and molecular subtypes.

Because TIM-3 expression was similar on bulk AML cells and the LSC-enriched fraction, we used bulk AML gene expression data from a previously described cohort of 526 adult AML patients to examine TIM-3 expression across cytogenetic and molecularly-defined subgroups of AML. Across cytogenetic subgroups, TIM-3 was more highly expressed in AML associated with core binding factor translocations, t(8;21)(q22;q22) and idt(16), but was still detected in samples from other subtypes. In NKAML, no significant associations were identified between TIM-3 expression and either FLT3-ITD or NPM1c mutations; however, higher TIM-3 expression was detected in the presence of mutations in one or both copies of CEBPA.

Figure 11E:
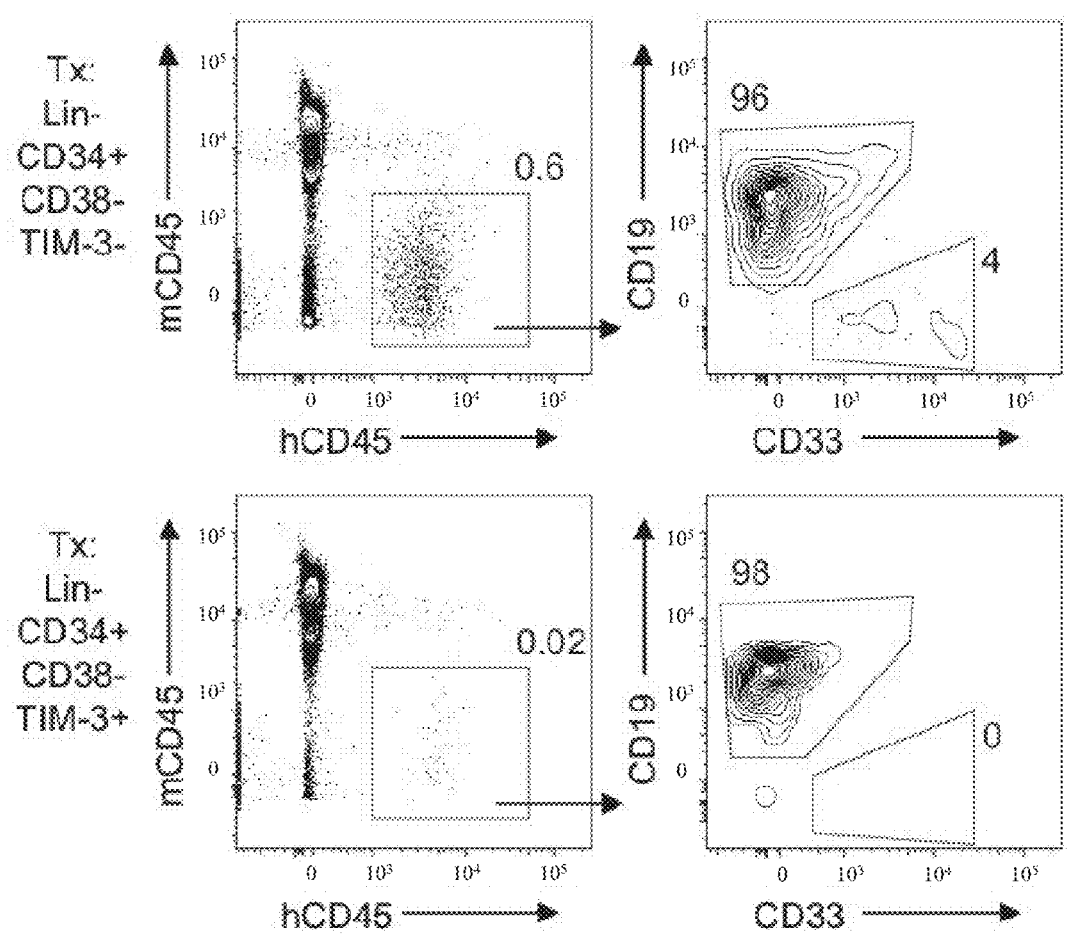
Figure 11F:
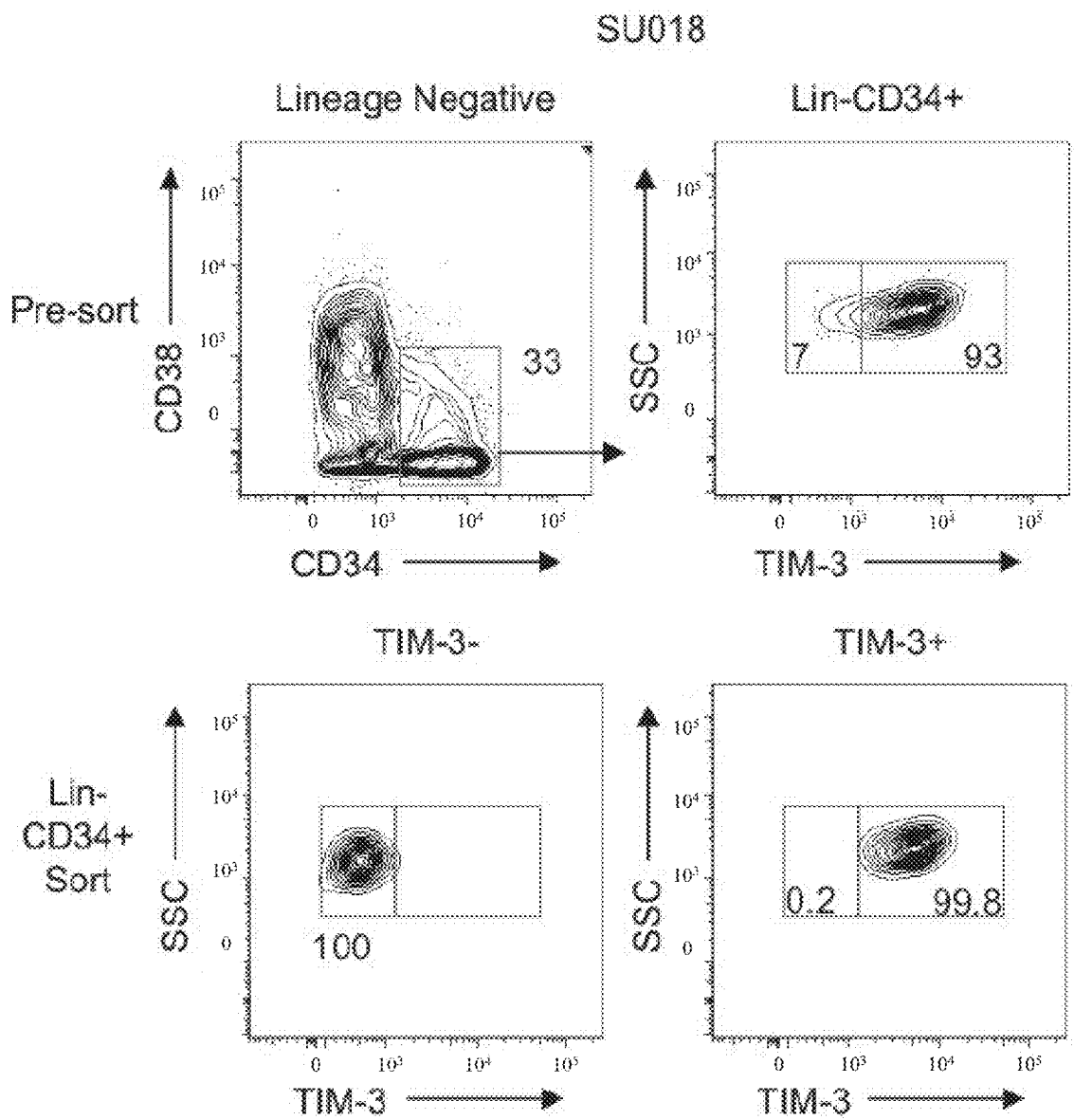
Figure 11G:
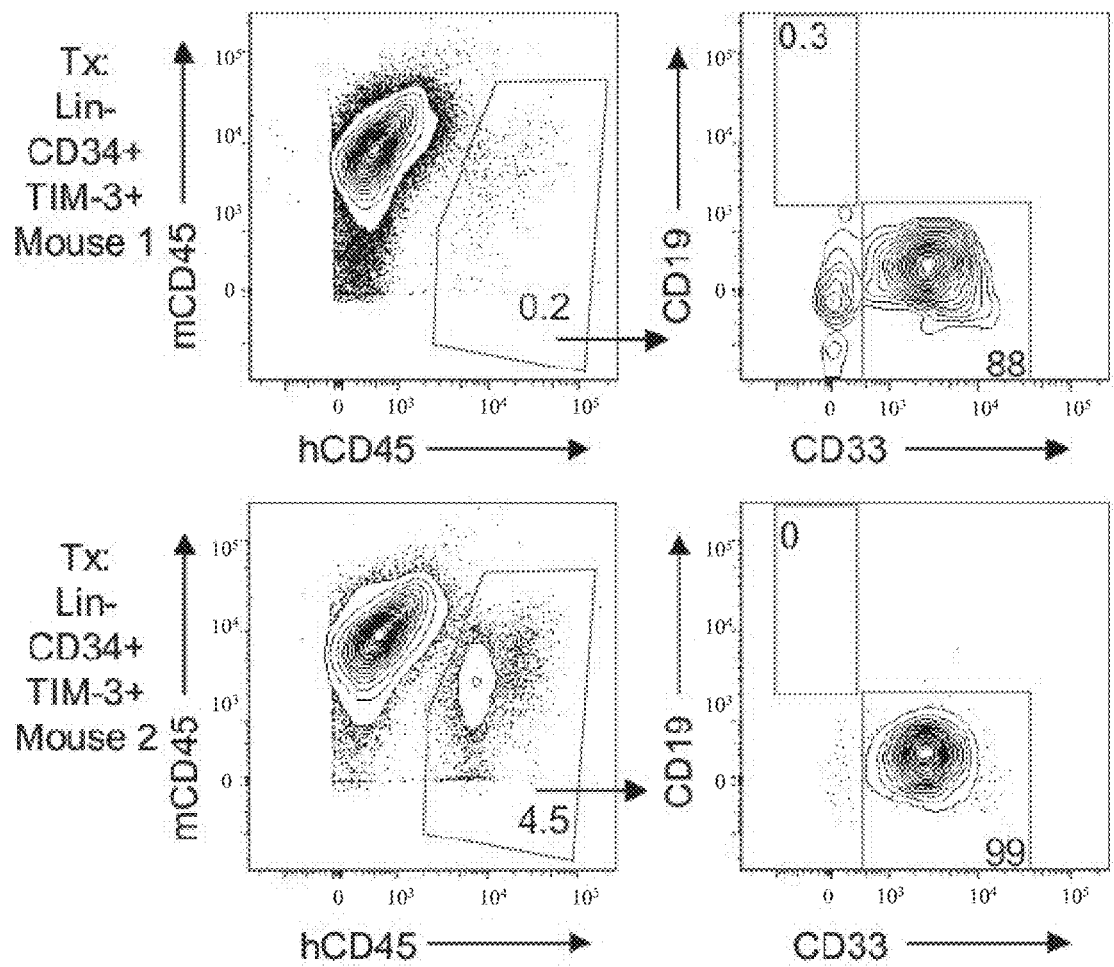

TIM-3 Is Not Expressed On Functional Normal Bone Marrow HSC. TIM-3 expression was detected on a minority of cells within the Lin-CD34+CD38- compartment of normal bone marrow by flow cytometry. To investigate the function of TIM-3 expressing cells in this HSC-enriched fraction, we used fluorescence-activated cell sorting (FACS) to purify Lin-CD34+CD38-TIM-3+ and Lin-CD34+CD38-TIM-3- subpopulations of normal bone marrow (FIG. 11 D) and assessed each subpopulation by transplantation into NOD/SCID/IL2Rγ$^{null}$ (NSG) mice. Consistent with HSC function, Lin-CD34+CD38-TIM-3- normal bone marrow cells engrafted long-term lympho-myeloid hematopoiesis, as indicated by the presence of human CD45+CD19+lymphoid cells and human CD45+CD33+myeloid cells in the bone marrow 12 weeks post-transplant (FIG. 11E). However, at an equal cell dose, Lin-CD34+CD38-TIM-3+ normal bone marrow cells did not engraft lympho-myeloid hematopoiesis, but did engraft one mouse with lymphoid-restricted human CD45+CD19+ cells (FIG. 11 E), suggesting that this population may contain a downstream multipotent or lymphoid-restricted progenitor. Similar results were obtained with a second normal bone marrow specimen. In total, 5 out of 7 mice transplanted with Lin-CD34+CD38-TIM3- cells exhibited HSC function compared to 0 out of 6 mice transplanted with Lin-CD34+CD38-TIM3+ cells (Table 4A). These results indicate that TIM-3 is not expressed on functional normal bone marrow HSC.

TABLE 4

Summary of in vivo engraftment in NSG mice from (A) normal human bone marrow and (B) primary human AML samples. Lin-CD34+CD38-TIM-3- cells were not detected in AML samples denoted with an (*). (C) Success of prospective isolation of TIM-3- normal HSC from 6 AML samples with residual normal hematopoietic engraftment detected in NSG mice and 1 AML sample with residual normal hematopoietic methylcellulose colony formation activity ($^Y$).

A.

| NBM Sample | Cell Population | Cell Dose | Lympho-Myeloid HSC Engraftment | Lymphoid-restricted Engraftment |
|---|---|---|---|---|
| NBM05 | Lin-CD34+CD38-TIM-3+ | 600 | 0/3 | 1/3 |
|  | Lin-CD34+CD38-TIM-3- | 600 | 2/3 | 1/3 |
| NBM06 | Lin-CD34+CD38-TIM-3+ | 1230 | 0/3 | 0/3 |
|  | Lin-CD34+CD38-TIM-3- | 5500 | 2/2 | 0/2 |
|  |  | 1230 | 1/2 | 1/2 |
| Summary | Lin-CD34+CD38-TIM-3+ |  | 0/6 | 1/6 |
|  | Lin-CD34+CD38-TIM-3- |  | 5/7 | 2/7 |

B.

| AML Sample | Cell Population | Cell Dose | Leukemic Engraftment | Secondary Engraftment |
|---|---|---|---|---|
| SU001* | Lin-CD34+CD38-TIM-3+ | 344,000 | 3/3 |  |
| SU004* | Lin-CD34+CD38-TIM-3+ | 240,000 | 3/3 |  |
| SU018 | Lin-CD34+TIM-3+ | 350,000 | 2/2 |  |
|  |  | 12,000 | 2/2 | 2/2 |
|  | Lin-CD34+TIM-3- | 12,000 | 0/2 |  |
| SU028* | Lin-CD34+CD38-TIM-3+ | 350,000 | 2/2 |  |
|  |  | 22,000 | 4/4 | 4/4 |
| SU030 | Lin-CD34+CD38-TIM-3+ | 200,000 | 2/2 |  |
|  |  | 20,000 | 2/2 |  |
|  | Lin-CD34+CD38-TIM-3- | 400 | 0/4 |  |
| Summary | Lin-CD34+(CD38-)TIM-3+ |  | 20/20 | 6/6 |
|  | Lin-CD34+(CD38-)TIM-3- |  | 0/6 |  |

C.

| AML Sample | Residual Normal HSC | Prospective Separation of TIM-3- HSC |
|---|---|---|
| SU008 | Yes | No |
| SU014 | Yes | No |
| SU030 | Yes | Yes |
| SU031 | Yes | Yes |
| SU035 | Yes | No |
| SU036 | Yes | No |
| SU043 | Yes$^Y$ | Yes |

Figure 13A:
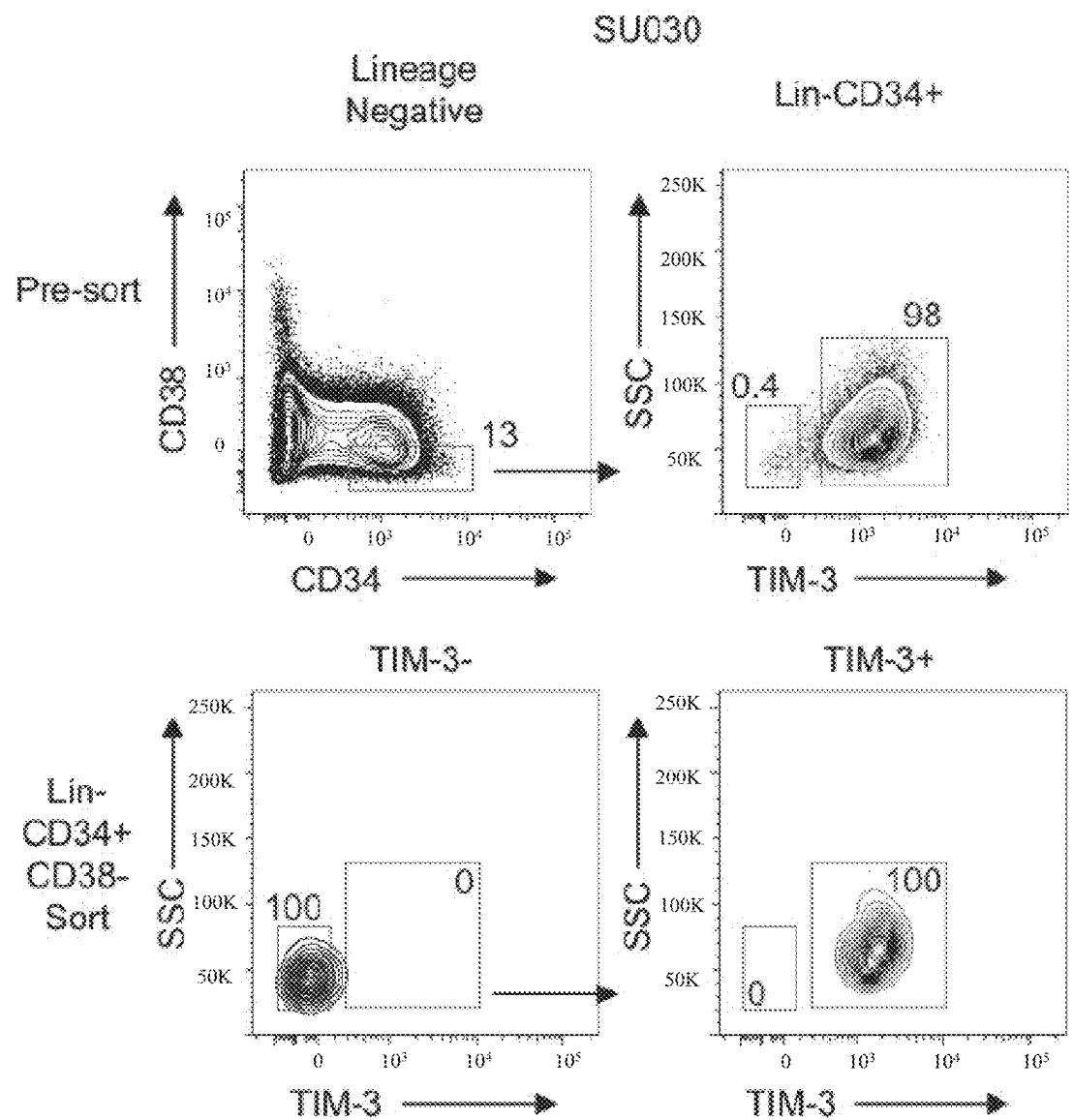
Figure 13B:
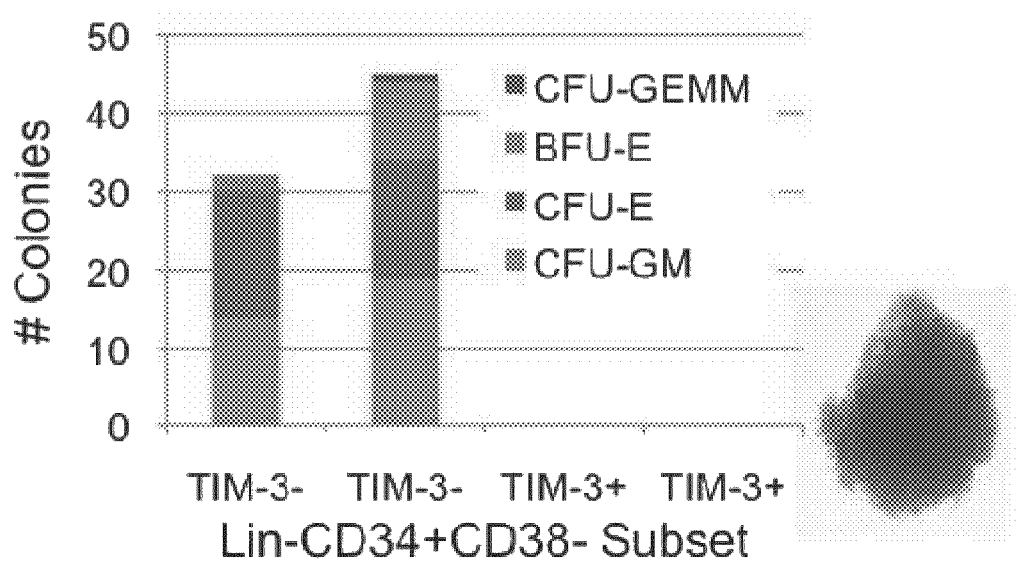
Figure 13D:
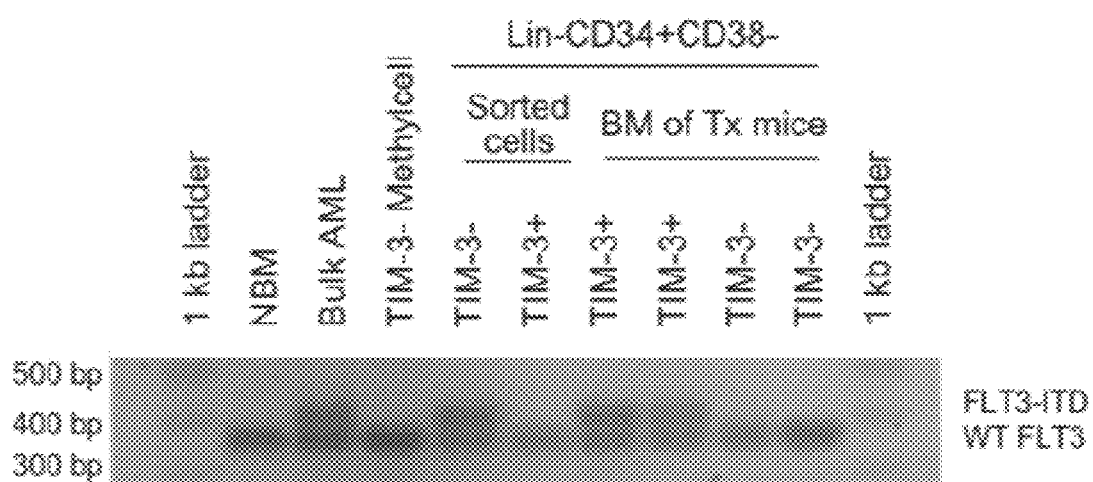

TIM-3 Is Highly Expressed On Functional AML Stem Cells. We next investigated whether TIM-3 was expressed on functional AML stem cells from five patient samples, as defined by the capacity to transplant long-term leukemic engraftment in NSG mice. In three of these five cases, all Lin-CD34+CD38- cells were TIM-3+, and each Lin-CD34+CD34-TIM-3+ cell population engrafted NSG mice with leukemia (Table 4B). In one AML sample with heterogeneous TIM-3 expression, FACS-purified Lin-CD34+TIM-3+ cells were able to transplant the disease into primary and secondary NSG recipients, whereas an equal dose of Lin-CD34+TIM-3- cells failed to transplant the disease (FIG. 11 F,G). Similarly, functional LSC were contained within the Lin-CD34+CD38-TIM-3+ fraction but absent from the the Lin-CD34+CD38-TIM-3- fraction of a second sample (FIG. 13). In summary, LSC were restricted to the TIM-3+ fraction of the Lin-CD34+ or Lin-CD34+CD38- compartment in all five engrafting AML samples tested (Table 4B). These results indicate that TIM-3 is highly expressed on functional AML LSC from multiple patients.

Prospective Separation of Normal HSC From LSC in a Series of AML Patients. We identified seven primary AML specimens with a high percentage of leukemia cells (mean and median blast counts of 80% and 86% respectively) which exhibited evidence of residual normal hematopoietic stem/progenitor function, as assessed by engraftment of lympho-myeloid hematopoiesis in NSG mice and/or normal erythro-myeloid colony-forming activity in complete methylcellulose (Table 4C). Because we detected TIM-3 expression on functional AML LSC, but not normal bone marrow HSC, we investigated the ability of differential expression to discriminate residual normal HSC from LSC in the same patient sample, and permit the prospective separation of these critical stem cell populations.

Figure 12A:
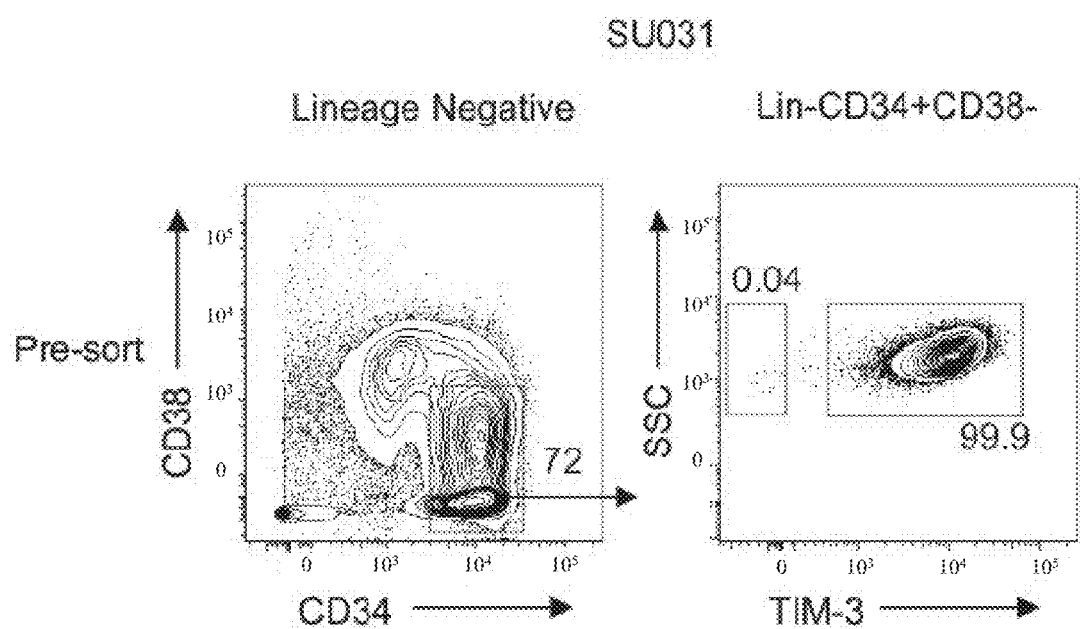
Figure 12D:
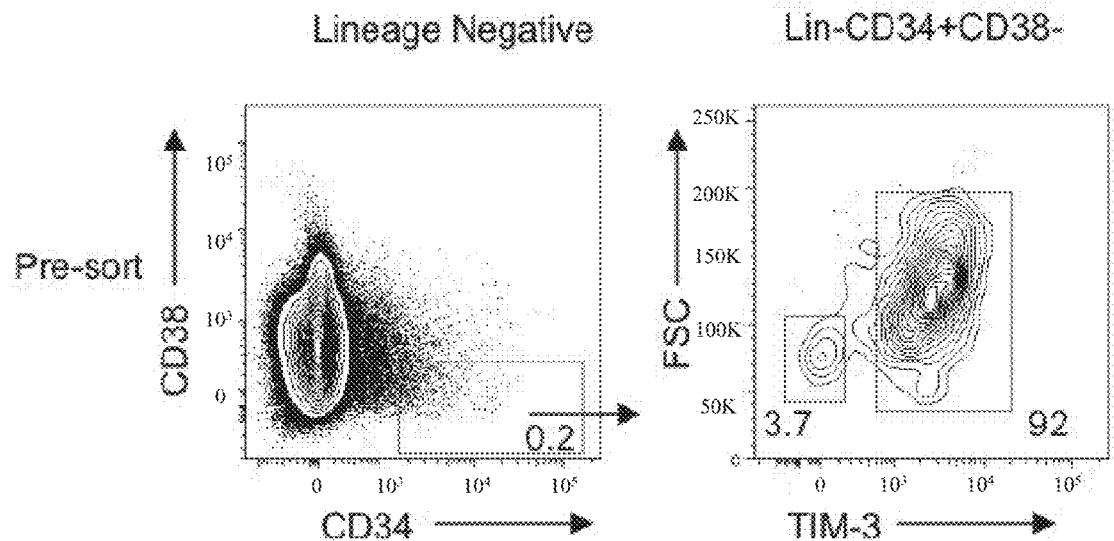
Figure 12E:
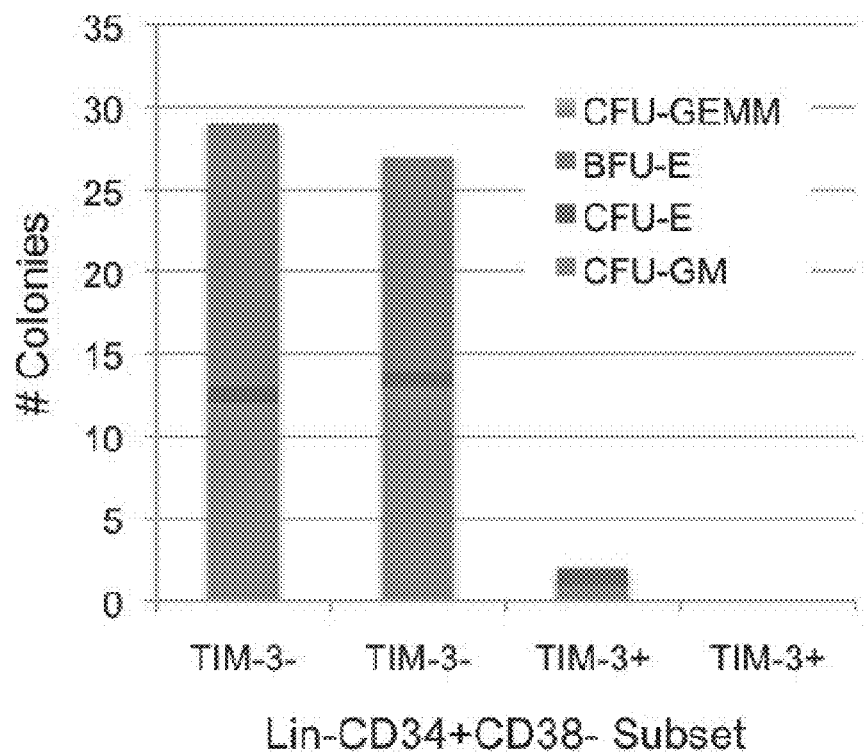
Figure 12F:
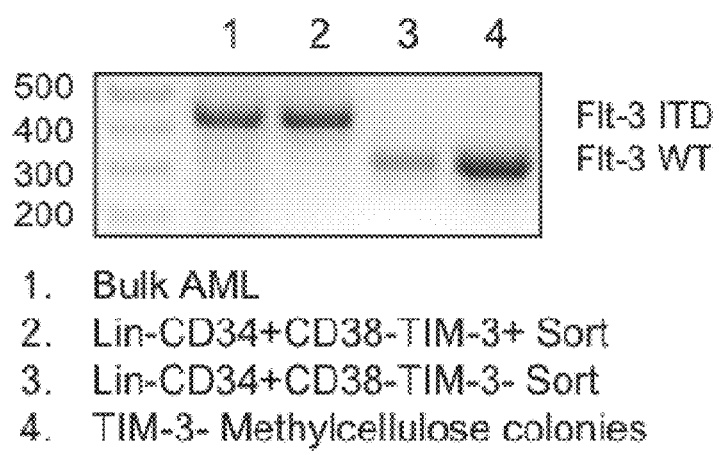

Three of these seven samples had rare TIM-3- populations which constituted between 0.04% and 3.7% of the Lin-CD34+CD38- compartment (FIGS. 12A,D and 13A). In each case, Lin-CD34+CD38-TIM3- and Lin-CD34+CD38-TIM3+ cells were isolated by FACS and functionally assayed by transplantation in NSG mice and/or colony formation in complete methylcellulose. Each rare TIM3- population exhibited normal HSC function with long-term lympho-myeloid engraftment in vivo (FIGS. 12B and 13C) and/or normal methylcellulose colony formation in vitro (FIGS. 12E and 13B). To further investigate the relationship between these residual functionally normal HSC and the leukemic clone, Lin−CD34+CD38−TIM3− FACS-purified cells, methylcellulose colonies derived from this population, and bone marrow cells from NSG mice engrafted with this population were assessed for the presence of known molecular mutations present in the leukemia (FLT3-ITD or inv (16)). In each case, the molecular mutation was detected in the TIM3+ cells but not in the rare TIM−3− cells (FIGS. 12C,F and 13D).

In vivo leukemic engraftment was not observed with two of these samples (SU031 and SU043) despite transplantation of greater than $10^5$ cells in NSG mice (Table 4B), consistent with the previously reported inability of some primary human AML specimens to engraft in immunodeficient mice. In contrast, the third sample (SU030) exhibited both normal hematopoietic and leukemic engraftment in NSG mice in vivo. In this case, Lin−CD34+CD38−TIM3− cells engrafted FLT3-ITD-negative long-term lympho-myeloid hematopoiesis, whereas Lin−CD34+CD38−TIM3+ cells engrafted FL T3-ITD-positive long-term myeloid-restricted leukemia (FIG. 13C,D). Thus, differential TIM−3 expression discriminates residual normal HSC from LSC in these three AML patient samples (Table 4C), permitting the prospective separation of these critical stem cell populations.

We report here the identification of TIM−3 as a novel AML stem cell surface marker that is highly expressed on multiple specimens of AML LSC, but not on normal bone marrow HSC. TIM−3 expression was detected in all cytogenetic subgroups of AML, but was significantly higher in AML-associated with core binding factor translocations or mutations in CEBPA. By assessing engraftment in NSG mice, we determined that normal bone marrow HSC do not express TIM−3, whereas LSC from multiple AML specimens express high levels of TIM−3. Finally, TIM−3 expression enabled the prospective separation of HSC from LSC in three out of seven AML samples with residual normal HSC function.

TIM−3 is normally expressed on Th1−T cells, dendritic cells, and monocytes, where downstream signal transduction is induced by cross-linking with its ligand Galectin-9 (GAL-9). The GAL-9/TIM−3 axis is a potent regulator of adaptive and innate immune responses. TIM−3 is expressed at low levels on naïve T cells, but is increased upon T cell activation and differentiation into Th1 cells. GAL-9 binding to TIM−3 on Th1 cells results in activation of NFkB and eventually apoptotic cell death, and in this way TIM−3 serves to dampen Th1 immune responses. In dendritic cells, TIM−3 signal transduction also stimulates NFkB activity, which leads to dendritic cell activation rather than apoptosis. Currently, the signal transduction pathways downstream of TIM−3 are unknown, but GAL-9 binding to TIM−3 can result in tyrosine phosphorylation of TIM−3.

Elevated TIM−3 expression may directly contribute to AML pathogenesis through either a cell-intrinsic mechanism or by disrupting anti-AML leukocyte activity. One potential cell-intrinsic mechanism involves stimulation of NFkB activity downstream of TIM−3 signal transduction in LSC. NFkB is active in AML LSC, and several pharmacologic inhibitors have been shown to have efficacy against primary LSC. Alternatively, TIM−3 may contribute to leukemogenesis by decreasing the concentration of unbound GAL-9 in the leukemic microenvironment. Attenuating GAL-9/TIM−3 signaling in infiltrating immune cells may result in decreased macrophage and dendritic cell pro-inflammatory signaling and activation. We recently demonstrated that phagocytic cells of the innate immune system, including macrophages and dendritic cells, play a key role in leukemic pathogenesis, and that most AML LSC have increased expression of CD47 to avoid phagocytosis. Thus, attenuation of GAL-9/TIM−3 signaling may be an additional mechanism to inhibit the innate immune response to AML.

In addition to a potential role in leukemic pathogenesis, TIM−3 is an excellent candidate for AML LSC-targeted therapeutic monoclonal antibodies. The absence of TIM−3 expression on functional normal bone marrow HSC and residual HSC in AML samples, in contrast to high expression on multiple samples of AML LSC, provides the rationale for developing such antibodies. Recently, we demonstrated that a blocking monoclonal antibody directed against CD47, a protein overexpressed on LSC, eliminated AML LSC by stimulating phagocytosis through Fc receptor-independent mechanisms. In this context, anti-TIM−3 antibodies able to bind and activate Fc receptors synergize with anti-CD47 antibodies to induce more effective phagocytic elimination of AML LSC.

A major result from the current study is the prospective separation of residual HSC from AML LSC based on differential expression of TIM−3. Such prospective separation has several clinical applications. Autologous hematopoietic cell transplantation (AHCT) has been utilized in the treatment of AML, including investigation of protocols employing ex vivo chemotherapy to eradicate residual leukemic cells in the autograft. AHCT has fallen out of mainstream clinical practice due to equivalence to conventional chemotherapy. However, purification of LSC-depleted functionally normal HSC may improve AHCT outcomes and broaden the use of AHCT to patients who do not achieve complete remission. Second, the ability to differentiate HSC and LSC by flow cytometry enables evaluation of LSC-targeted therapeutics and prediction of relapse based upon minimal residual disease monitoring at the level of the LSC. This possibility is supported by the demonstration that increased expression of the LSC marker CLL-1 in the CD34+CD38− bone marrow fraction from two AML patients in remission correlated with relapse.

Lastly, prospective separation of residual functionally normal HSC from LSC based on TIM−3 expression further provides an opportunity to map the accumulation of mutations leading to AML. Because leukemogenesis involves the multistep accumulation of rare mutations, pre-leukemic mutations likely accumulate in self-renewing HSC. Ultimately, the novel ability to prospectively isolate functionally normal HSC from AML patients could enable the direct identification of pre-leukemic mutations and may serve as an entry point into observing the accumulation of leukemogenic events in pre-leukemic HSC.

Materials and Methods

Human Samples. Normal human bone marrow mononuclear cells were purchased from AllCells Inc. (Emeryville, Calif., USA). Human AML samples were obtained from patients at the Stanford Medical Center with informed consent, according to IRB-approved protocols (Stanford IRB #76935 and 6453).

Animal Care. All mouse experiments were conducted according to an IACUC-approved protocol and in adherence to the NIH Guide for the Care and Use of Laboratory Animals.

Flow Cytometry Analysis and Cell Sorting. A panel of antibodies was used for analysis and sorting of AML LSC (Lin−CD34+CD38−) and HSC (Lin−CD34+CD38−CD90+)

as previously described. For AML samples, the lineage consisted of CD3, CD19, and CD20. TIM-3 antibody clone 344823 (R&D Systems, Minneapolis, Minn., USA) was used. Human CD34-positive cells were enriched from normal bone marrow by magnetic selection (StemCell Technologies, Vancouver, BC, Canada).

Methylcellulose Colony Assay. Erythro-myeloid colony formation was assayed by culturing hematopoietic cells in complete methylcellulose (Methocult GF+ H4435, Stem Cell Technologies). Colony formation was assayed after 14 days in culture by microscopy. Colony types scored were: CFU-GEMM, colony forming unit—granulocyte, erythrocyte, monocyte, megakaryocyte, BFU-E, blast forming unit—erythrocyte, CFU-E, colony forming unit—erythrocyte, and CFU-GM—colony forming unit—granulocyte, monocyte.

NSG Xenotransplantation Assay. FACS-purified cell populations were transplanted into newborn NOD/SCID/IL2Rγ-null (NSG) mice conditioned with 100 rads of irradiation. After twelve weeks, mice were sacrificed and peripheral blood and bone marrow were analyzed for human myeloid engraftment (hCD45+CD33+) and human lymphoid engraftment (hCD45+CD19+). For secondary transplantation, whole mouse bone marrow cells from primary mice containing 10,000 human leukemic cells were transplanted into irradiated newborn NSG mice and analyzed for engraftment 12 weeks later by flow cytometry.

Microarray Analysis of TIM-3 Expression. Raw Affymetrix CEL files (n=526) were downloaded from NCBI GEO (GSE14468) and normalized using MAS5 in Bioconductor. Arrays were scaled to median intensity of 500 and transformed to log 2 values. We used a custom CDF (Chip Definition File) to map array 22-mers to Refseq mRNA accessions (44). TIM3/HAVCR2 was represented by the probe summarization corresponding to Refseq accession NM_032782. NKAML samples (n=219) were identified as having "Normal" karyotype and non-M3 (acute promyelocytic leukemia) FAB subtype. Boxplots of TIM3 expression were generated in R across all karyotypes (n=526), and across FLT3-ITD, NPM1, and CEBPA mutation groups for NKAML (n=219). Association of TIM3 to karyotypic groups and mutational status was evaluated by ANOVA.

PCR analysis for inv(16) and FLT3-ITD. Total RNA was isolated by Rneasy Micro Kit (Qiagen). cDNA was reverse transcribed with SuperScript III First-Strand Synthesis Kit (Invitrogen). Inv(16) was detected by PCR with the following primers: CBFB-C (F) SEQ ID NO:1 5'-GGGCTGTCTGGAGTTTGATG-3' and MYH11-B2 (R) SEQ ID NO:2 5'-TCCTCTTCTCCTCATTCTGCTC-3'. Genomic DNA was isolated by Gentra Puregene Cell Kit (Qiagen). FLT3-ITD was detected by PCR with the following primers: FLT3 11 F (F) SEQ ID NO:3 5'-GCAATT-TAGGTATGAAAGCCAGC-3' and FLT3 12R (R) SEQ ID NO:4 5'-CTTTCAGCATTTTGACGGCAACC-3'.

What is claimed is:

1. A method of treating a human subject for a pre-leukemic condition, the method comprising:
   administering to a human subject in need thereof an antibody that specifically binds TIM3 at a dose that achieves a depletion in pre-leukemic cells.

2. The method of claim 1, wherein the preleukemic condition is myelodysplastic syndrome.

3. The method of claim 1, wherein the pre-leukemic condition is selected from chronic myelogenous leukemia, polycythemia vera, essential thrombocytosis, agnogenic myelofibrosis and myeloid metaplasia.

4. The method of claim 1, wherein the human subject is treated with a chemotherapeutic drug.

5. The method of claim 1, wherein the antibody is conjugated to a cytotoxic agent.

6. The method of claim 5, wherein the cytotoxic agent is selected from the group consisting of a radioactive isotope, a chemotherapeutic agent and a toxin.

7. The method of claim 1, further comprising administration of an antibody that disrupts the binding of CD47 with SIRPα, at a dose that achieves a depletion in pre-leukemic cells by increasing phagocytosis of pre-leukemic cells.

8. The method of claim 7, wherein the antibody that disrupts the binding of CD47 with SIRPα specifically binds to CD47.

9. The method of claim 8, wherein the antibody that specifically binds to CD47 is a humanized or chimeric monoclonal antibody.

10. A method of treating a human subject for acute myeloid leukemia (AML), the method comprising:
    administering to a human subject in need thereof an antibody that specifically binds TIM3 at a dose that achieves a depletion in AML cells.

11. The method of claim 10, wherein the human subject is treated with a chemotherapeutic drug.

12. The method of claim 10, wherein the antibody is conjugated to a cytotoxic agent.

13. The method of claim 12, wherein the cytotoxic agent is selected from the group consisting of a radioactive isotope, a chemotherapeutic agent and a toxin.

14. The method of claim 10, further comprising administration of an antibody that disrupts the binding of CD47 with SIRPα, at a dose that achieves a depletion in pre-leukemic cells by increasing phagocytosis of pre-leukemic cells.

15. The method of claim 14, wherein the antibody that disrupts the binding of CD47 with SIRPα specifically binds to CD47.

16. The method of claim 15, wherein the antibody that specifically binds to CD47 is a humanized or chimeric monoclonal antibody.

\* \* \* \* \*